(12) United States Patent
Lee et al.

(10) Patent No.: US 11,214,816 B2
(45) Date of Patent: Jan. 4, 2022

(54) RECOMBINANT MICROORGANISM HAVING HETEROLOGOUS GENES INTRODUCED THERETO AND METHOD FOR PRODUCING USEFUL MATERIAL FROM FORMIC ACID AND CARBON DIOXIDE USING SAME MICROORGANISM

(71) Applicant: KOREA ADVANCED INSTITUTE OF SCIENCE AND TECHNOLOGY, Daejeon (KR)

(72) Inventors: Sang Yup Lee, Daejeon (KR); Junho Bang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/472,876

(22) PCT Filed: Nov. 20, 2017

(86) PCT No.: PCT/KR2017/013171
§ 371 (c)(1),
(2) Date: Jun. 23, 2019

(87) PCT Pub. No.: WO2018/124475
PCT Pub. Date: Jul. 5, 2018

(65) Prior Publication Data
US 2019/0338316 A1 Nov. 7, 2019

(30) Foreign Application Priority Data

Dec. 27, 2016 (KR) .................. 10-2016-0180223
Nov. 14, 2017 (KR) .................. 10-2017-0151642

(51) Int. Cl.
| | | |
|---|---|---|
| C12P 1/04 | (2006.01) | |
| C12N 15/70 | (2006.01) | |
| C12P 13/04 | (2006.01) | |
| C12P 5/02 | (2006.01) | |
| C12P 7/04 | (2006.01) | |
| C12P 7/24 | (2006.01) | |

(52) U.S. Cl.
CPC .............. *C12P 1/04* (2013.01); *C12N 15/70* (2013.01); *C12P 5/02* (2013.01); *C12P 7/04* (2013.01); *C12P 7/24* (2013.01); *C12P 13/04* (2013.01); *C12Y 101/01081* (2013.01); *C12Y 105/01005* (2013.01); *C12Y 206/01045* (2013.01); *C12Y 208/03015* (2013.01); *C12Y 305/04009* (2013.01); *C12Y 401/03024* (2013.01); *C12Y 602/01009* (2013.01); *C12Y 603/04003* (2013.01)

(58) Field of Classification Search
CPC .... C12Y 101/01081; C12Y 208/03015; C12Y 603/04003; C12Y 105/01005; C12Y 206/01045; C12Y 305/04009; C12Y 401/03024; C12Y 602/01009; C12P 13/04; C12P 5/02; C12P 7/625; C12P 7/24; C12P 13/001; C12P 1/04; C12P 7/04; C12P 7/649; C12N 15/70; Y02E 50/10
See application file for complete search history.

(56) References Cited

U.S. PATENT DOCUMENTS

| | | |
|---|---|---|
| 2003/0124687 A1 | 7/2003 | Gunji et al. |
| 2013/0196359 A1 | 8/2013 | Siegel et al. |
| 2015/0218528 A1* | 8/2015 | Bar-Even ............... C12N 13/00 435/173.1 |

FOREIGN PATENT DOCUMENTS

| | | |
|---|---|---|
| DE | 102007048625 A1 | 4/2009 |
| JP | 2014-155455 A | 8/2014 |
| KR | 100679638 B | 1/2007 |
| KR | 1020090117739 A | 11/2009 |
| WO | 2008101857 A2 | 8/2008 |
| WO | 2009062190 A2 | 5/2009 |
| WO | 2014020599 A1 | 2/2014 |
| WO | 2015058188 A1 | 4/2015 |

OTHER PUBLICATIONS

G. Heil et al. "Glycine binds the transcriptional accessory protein GcvR to disrupt a GcvA/GcvR interaction and allow GcvA-mediated activation of the *Escherichia coli* gcvTHP", Microbiology 148: 2203-2214 (Year: 2002).*
GenBank Accession No. CP001298 Region 2230986-2232572. (Year: 2013).*

(Continued)

*Primary Examiner* — Ganapathirama Raghu
(74) *Attorney, Agent, or Firm* — Hultquist, PLLC; Steven J. Hultquist

(57) ABSTRACT

The present invention relates to a recombinant microorganism having heterologous genes introduced thereto and a method for producing a useful material from formic acid and carbon dioxide using the microorganism. The present invention provides a novel microorganism having a cyclic metabolic pathway introduced thereto through which C3 or higher carbon organic compounds can be synthesized from formic acid and carbon dioxide, whereby carbon dioxide rich in nature and formic acid that is of low toxicity and suitable for anabolic reaction in view of reaction kinetics and which can be easily and rapidly synthesized from carbon dioxide can be used to effectively synthesize the C3 organic compound pyruvic acid from which various high-value added compound can be synthesized.

16 Claims, 15 Drawing Sheets
(15 of 15 Drawing Sheet(s) Filed in Color)
Specification includes a Sequence Listing.

(56) References Cited

OTHER PUBLICATIONS

B.K. Pomper et al. "A methenyl tetrahydromethanopterin cyclohydrolase and a methenyl tetrahydrofolate cyclohydrolase in Methylobacterium extorquens AM1", Eur. J. Biochem. 261: 475-480 (Year: 1999).*
Christoserdova et al. "Genetics of the Serine Cycle in Methylobacterium extorquens AM1: cloning, sequence, mutation, and physiological effect of glyA, the gene for serine hydroxymethyltransferase", J. Bacteriology 176(23)7398-7404 (Year: 1994).*
GenBank Accession No. AP009048 Region 3044824-3049323. (Year: 2016).*
GenBank CP002987 Region 1082745-1084347. (Year: 2015).*
Bar-Even, A., "Formate assimilation: The metabolic architecture of natural and synthetic pathways", "Biochemistry", 2016, pp. 3851-3863, vol. 55, No. 28, Publisher: American Chemical Society.
Crowther, G., et al., "Formate as the Main Branch Point for Methylotropic Metabolism in Methylobacterium extorquens AM1", "Journal of Bacteriology", May 2008, pp. 5057-5062, vol. 190, No. 14, Publisher: Journals.ASM.org.
Datsenko, K., et al., "One-step inactivation of chromosomal genes in Escherichia coli K-12 using PCR products", "PNAS", 2000, pp. 6640-6645, vol. 97, No. 12.
Federsel, C., et al., "A Well-Defined Iron Catalyst for the Reduction of Bicarbonates and Carbon Dioxide to Formates, Alkyl Formates, and Formamides", "Angew. Chem. Int. Ed.", 2010, pp. 9777-9780, vol. 49, Publisher: Wiley-bch Verleg GmbH & Co.
Gibson, D., et al., "Enzymatic assembly of DNA molecules up to several hundred kilobases", "Nature Methods", 2009, pp. 343-345, vol. 6, No. 5, Publisher: 2009 Nature America, Inc. (npg).
Kumar, B., et al., "Renewable and metal-free carbon nanofibre catalysts for carbon dioxide reduction", "Nature Communications: www.nature.com/naturecommunications", 2013, p. 2819, vol. 4, No. DOI: 10.1038, Publisher: Macmillan Publishers Limited.
"Escherichia coli str. K-12 substr. MG1655, complete genome", "NCBI information: NC_000913.3", 2018.
Neumann, E., et al., "Gene transfer into mouse lyoma cells by electroporation in high electric fields", "The EMBO Journal", 1982, pp. 841-845, vol. 1, No. 7, Publisher: IRL Press Limited.
Schwander, T., et al., "A synthetic pathway for the fixation of carbon dioxide in vitro", "Science", 2016, pp. 900-904, vol. 354, No. 6314, Publisher: sciencemag.org.
Studt, F., et al., "Discovery of a Ni—Ga catalyst for carbon dioxide reduction to methanol", "Nature Chemistry", Mar. 2, 2014, pp. 320-324, vol. 6, No. DOI: 10.1038/NCHEM.1, Publisher: Macmillan Publishers Limited.
Zamboni, N., et al., "13 C-based metabolic flux analysis", "Nature Protocols", 2009, pp. 878-892, vol. 4, No. 6.
Zelcbuch, L., et al., "Pyruvate formate-lyase enables efficient growth of Escherichia coli on acetate and formate", "Biochemistry", 2016, pp. 2423-2426, vol. 55, No. 17, Publisher: ACS Publications.
Bar-Even, A., et al., "Design and analysis of metabolic pathways supporting formatotrophic growth for electricity-dependent cultivation of microbes", "Biochimica et Biophysica Acta", 2013, pp. 1039-1047, vol. 1827, Publisher: Elsevier.

* cited by examiner

A

B

Labeled Alanine

SEQUENCE LISTING

<160> NUMBER OF SEQ ID NOS: 69

<210> SEQ ID NO 1
<211> LENGTH: 40
<212> TYPE: DNA
<213> ORGANISM: Artificial Sequence
<220> FEATURE:
<223> OTHER INFORMATION: Forward primer for constructing a recombinant plasmid

<400> SEQUENCE: 1

```
actgataagc ctttcggtaa ggtacccggg gatcctctag                          40
```

<210> SEQ ID NO 2
<211> LENGTH: 40
<212> TYPE: DNA
<213> ORGANISM: Artificial Sequence
<220> FEATURE:
<223> OTHER INFORMATION: Reverse primer for constructing a recombinant plasmid

<400> SEQUENCE: 2

```
tcgtgtaagt gtctcaacaa gagctcgaat tcgctagcac                          40
```

<210> SEQ ID NO 3
<211> LENGTH: 1173
<212> TYPE: DNA
<213> ORGANISM: Methylobacterium extorquens

<400> SEQUENCE: 3

```
atggacgttc acgagtacca agccaaggag ctgctcgcga gcttcggggt cgccgtcccg     60
aagggcgccg tggctttcag cccggatcaa gcggtctacg cggcgaccga gctcggcggc    120
tcgttctggg cggtgaaggc tcagatccat gccggcgcgc gcggcaaggc gggcgggatc    180
aagctctgcc gcacctacaa cgaagtgcgc gacgccgccc gcgacctact gggaaaacgc    240
ctcgtgacgc ttcagaccgg ccccgagggc aagccggtgc agcgcgtcta cgtcgagacc    300
gccgacccgt tcgagcgtga actctatctc ggctacgtcc tcgatcgaaa ggccgagcgc    360
gtccgtgtca tcgcctccca gcgcggcggc atggatatcg aagagatcgc cgccaaggag    420
cccgaggcgc tgatccaggt cgtggtcgag cggcggtgg gcctgcagca gttccaggcc    480
cgcgagatcg cgttccagct cggcctcaac atcaagcagg tctcggccgc ggtgaagacc    540
atcatgaacg cctaccggc gttccgcgac tgcgacggca ccatgctgga tcaacccg      600
ctcgtcgtca ccaaggacga ccgggttctg gcactcgacg ccaagatgtc cttcgacgac    660
aacgccctgt tccgccgccg caacatcgcg gacatgcacg acccgtcgca gggcgatccc    720
cgcgaggccc aggctgccga gcacaatctc agctatatcg gcctcgaggg cgaaatcggc    780
tgcatcgtca acggcgcggg tctggccatg gcgaccatgg acatgatcaa gcatgcgggc    840
ggcgagccgg caaacttcct ggatgtgggc ggcggcgcca gcccggatcg cgtcgccacg    900
gcgttccgcc tcgttctgtc ggaccgcaac gtgaaggcga tcctcgtcaa catcttcgct    960
ggcatcaacc gctgcgactg gtcgcgcgag ggcgtggtca aggctgcgcg cgaggtgaag   1020
atcgacgtgc cgctgatcgt gcggctcgcc ggcacgaacg tcgatgaagg caagaagatc   1080
ctcgccgaaa gcgggctcga cctcatcacc gccgacaccc ttacggaagc cgcgcgcaag   1140
gctgtcgaag cctgccacgg cgccaagcac tga                                1173
```

<210> SEQ ID NO 4
<211> LENGTH: 891

```
<212> TYPE: DNA
<213> ORGANISM: Methylobacterium extorquens

<400> SEQUENCE: 4
atgagcattc tcatcgacga gaagaccccg atcctggtcc agggcatcac gggcgacaag      60
ggaaccttcc acgccaagga gatgatcgcc tacggctcca acgtcgtcgg cggcgtcacc     120
ccgggcaagg gcggcaagac ccattgcggc gtgccggtgt tcaacaccgt caaggaggcc     180
gtagaggcga ccggcgccac cacctcgatc accttcgtgg cgcctcccctt cgcggcggac    240
gcgatcatgg aggcggccga tgctggcctc aagcttgtct gctcgatcac cgacggcatc    300
cccgctcagg acatgatgcg ggtgaaacgc tacctccggc gctatccgaa ggagaagcgc    360
acgatggtgg tgggcccgaa ctgcgcgggc atcatctcgc ccggcaagtc gatgctcggc    420
atcatgcccg tcacatctca cctcccgggc aaggtcggcg tcatctcccg ctccggaacc    480
ctcggctacg aggccgcggc gcagatgaag gagctcggca tcggcatctc gacctccgtc    540
ggcatcggcg gcgatccgat caacggctcc tccttcctcg accacctcgc tctgttcgag    600
caggatcccg agacggaagc cgtgttgatg atcggcgaga tcggcggtcc gcaggaggcc    660
gaggcctcgg cctggatcaa ggagaacttt tccaagcccg tgattggctt cgtggcgggc    720
ctcaccgccc ccaagggccg ccgcatgggg catgccggcg cgatcatctc ggcgaccggc    780
gacagcgccg cggagaaggc cgagatcatg cgctcctacg gcctgaccgt ggcgcccgat    840
ccgggctcct tcggcagcac cgtagccgac gtgctcgccc gcgcggcgtg a              891

<210> SEQ ID NO 5
<211> LENGTH: 975
<212> TYPE: DNA
<213> ORGANISM: Methylobacterium extorquens

<400> SEQUENCE: 5
atgagcttca ccctgatcca gcaggccacc ccgcgcctgc accgctcgga actcgcggtt      60
cccggctcca acccgaccct catggagaag tcggccgcct cgaaggccga cgtgatcttc     120
ctcgacctcg aggacgcggt tgcgcccgac gacaaggagc aggcccgcaa gaacatcatc     180
caggccctca atgacctgga ttggggcaac aagaccatga tgatccgcat caacggtctc     240
gacacccact acatgtaccg cgacgtggtg gacatcgtgg aggcctgccc gcgcctcgac     300
atgatcctga tccccaaggt cggcgtgccg gccgacgtct acgccatcga cgtgctgacg     360
acgcagatcg agcaggccaa gaagcgcgag aaaaagatcg gcttcgaagt gctgatcgag     420
accgcgctcg gcatggccaa tgtcgaggcg atcgcgacct cgtctaagcg ccttgaggcg     480
atgtccttcg gtgtcgccga ctacgccgcc tccacccgcg cccgctccac cgtgatcggc     540
ggcgtcaatg ccgattacag cgtgctcacc gacaaggacg aggccggcaa ccgccagact     600
cactggcagg atccgtggct gttcgcccag aaccggatgc tggtcgcctg ccgcgcctac     660
ggcctgcgcc cgatcgacgg tcccttcggc gacttctccg atccggacgg ctacacctcg     720
gccgctcgcc gctgcgccgc gctcggcttc gagggcaagt gggcgatcca cccctcgcag     780
atcgatctgg ccaacgaggt cttcaccccc tccgaggccg aggtcaccaa ggcccgccgc     840
atcctggaag ccatggaaga ggccgccaag gccggccgcg cgccgtctc gctcgacggc     900
cgcctcatcg acatcgcctc gatccgcatg gccgaggcgc tgatccagaa ggccgacgcg     960
atgggcggaa agtaa                                                     975

<210> SEQ ID NO 6
```

```
<211> LENGTH: 1209
<212> TYPE: DNA
<213> ORGANISM: Methylobacterium extorquens

<400> SEQUENCE: 6
atggcggcaa cgagacgtcc gggacgcaac cacctgttcg ttcccggccc gaccaacatc      60
ccggaccggg tgatgcgcgc catgatggtg cagtccgagg atcaccgctc ggtcgatttc     120
ccgtcgctga cgaagccgct gttcgaggac accaagaagg tgttcggctc gaccgaaggc     180
acgatcttcc tgttcccggc ctccggcacg ggcatctggg aatcggcgct gtccaacacg     240
ctcgcccgcg cgacaaggt ggtggccgcc cgcttcggcc agttcagcca tctctggatc      300
gacatggccc agcgcctcgg cctggacgtc gtcgtccagg aggaggagtg gggcaccggc     360
gccaagcccg agaagatcga ggaggccctg cgcgccgaca gaaccatga gatcaaggcc      420 gtcatggtgg tccataacga gaccgcgacc ggcgtgacct ccaacatcgg cgccgtgcgc     480
aaggcgatcg acgccgccgg ccaccccggcc ctgctgttcg tcgacggcgt gtcctccatc    540
ggctcgctgc ccttcaaggc cgacgagtgg aaggtcgact cgccatcgc cggctcccag      600 aagggcctga tgctgcccgc cggcctcggc gtgatttgcg tcagccagaa ggcgctcaag     660
gccgccgagg ccagtccgg ccgcaacgac cggctcgccc gcgtctactt cgactgggaa      720
gaccagaaga gcagaaccc gaccggctac ttccctaca ccccgccgct gccgctgctc       780
tacggcctgc gcgaggcgct cgcctgcctg ttcgaggaag gctggagaa cgtctaccac      840 cgccacgccg tgctcggtga ggcgacccgt caggccgtcg cggcctgggg cctgaagacc     900
tgcgccaagt cgccggagtg gaactccgac accgtcaccg ccatcctggc gcccgagggt     960
gtggacgcgg ccaagatcat caagcacgcc tatgtgcgct acaacctcgc gctcggcgcc    1020
ggcctgtccc cagtcgcggg caaggtgttc cgcatcggtc acgtcggcga cctgaacgaa    1080
ctctcgctgc tcggcgccat cgccggtgcc gagatgtcgc tcatcgacaa cggcgtgaag    1140 gtgaccccg gttcgggtgt tgccgccgcc tccagctacc tgcgcgagaa cccgctcgcc    1200
aaggcttga                                                            1209

<210> SEQ ID NO 7
<211> LENGTH: 1674
<212> TYPE: DNA
<213> ORGANISM: Methylobacterium extorquens

<400> SEQUENCE: 7
atgccctcag atatcgagat cgcccgcgcg gcgaccctga agccgatcgc ccaggtcgcc      60
gaaaagctcg gcatcccgga cgaggcgctt cacaattacg gcaagcacat cgccaagatc     120
gaccacgact tcatcgcctc gctcgagggt aagcccgagg gcaagctggt gctcgtcacc     180
gcgatctcgc cgacgcctgc gggcgagggc aagaccacca cgactgtggg gctcggcgac     240
gcgctcaacc gcatcggcaa gcgggcggtg atgtgcctgc gcgagccctc gctcggcccc     300
tgcttcggca tgaagggcgg cgcggccggt ggcggcaagg cgcaggtcgt gccgatggag     360
cagatcaacc tgcacttcac cggcgacttc cacgccatca cctcggcgca ctcgctcgcc     420
gccgctctga tcgacaacca catctactgg gccaacgagc tcaacatcga cgtgcgccgc     480
atccactggc gccgcgtggt cgacatgaac gaccgagcgc tgcgcgcgat caaccagtcg     540
ctcggcggcg tcgccaacgg ctttccgcgt gaggacggct tcgacatcac cgtcgcctcc     600
gaggtgatgc gggtgttctg cctcgccaag aatctggctg acctcgaaga gcggctcggc     660
cgcatcgtca tcgccgagac ccgcgaccgc aagccggtga cgctggccga cgtgaaggcg     720
```

```
accggtgcga tgaccgttct cctcaaggac gcgcttcagc cgaacctcgt gcagacgctg      780
gagggcaacc cggccctgat ccatggcggc ccgttcgcca acatcgccca cggctgcaac      840
tcggtgatcg ccacccgcac cggcctgcgg ctggccgact acaccgtcac cgaggccggc      900
ttcggcgcgg atctcggcgc ggagaagttc atcgacatca agtgccgcca gaccggcctc      960
aagccctcgt cggtggtgat cgtcgccacg atccgcgccc tcaagatgca tggcggcgtc     1020
aacaagaagg atctccaggc tgagaacctc gacgcgctgg agaagggctt cgccaacctc     1080
gagcgccacg tgaataacgt ccggagcttc ggcctgccgg tggtggtggg tgtgaaccac     1140
ttcttccagg acaccgacgc cgagcatgcc cggttgaagg agctgtgccg cgaccggctc     1200
caggtcgagg cgatcacctg caagcactgg gcggagggcg gcgcgggcgc cgaggcgctg     1260
gcgcaggccg tggtgaagct cgccgagggc gagcagaagc gctgaccctt cgcctacgag     1320
accgagacga agatcaccga caagatcaag gcgatcgcga ccaagctcta cggcgcggcc     1380
gacatccaga tcgagtcgaa ggccgccacc aagctcgccg gcttcgagaa agacggctac     1440
ggcaaattgc cggtctgcat ggccaagacg cagtactcgt tctcgaccga cccgaccctg     1500
atgggcgcgc cctcgggcca cctcgtctcg gtgcgcgacg tgcgcctctc ggcgggcgcc     1560
ggcttcgtcg tggtgatctg cggtgagatc atgaccatgc cgggtctgcc aaaagtgccg     1620
gcggcggaca ccatccgcct ggacgccaac ggtcagatcg acgggctgtt ctag           1674

<210> SEQ ID NO 8
<211> LENGTH: 627
<212> TYPE: DNA
<213> ORGANISM: Methylobacterium extorquens

<400> SEQUENCE: 8
atggccggca acgagacgat cgaaacattc ctcgacggcc tggcgagctc ggccccgacc       60
cccggcggcg gcggtgccgc cgcgatctcc ggcgccatgg gcgcggcgct ggtgtcgatg      120
gtgtgcaacc tcaccatcgg caagaagaag tatgtcgagg tcgaggccga cctgaagcag      180
gtgctggaga gtcggaagg cctgcgccgc acgctcaccg gcatgatcgc cgacgacgtc       240
gaggctttcg acgcggtgat gggcgcctac ggctgccga agaacaccga cgaagagaag        300
gccgcccgcg ccgccaagat tcaagaggcg ctcaaaaccg gaccgacgt gccgctcgcc      360 tgctgccgcg tctgccgcga ggtgatcgac ctggccgaga tcgtcgccga agggcaat       420 ctcaacgtca tctcggatgc cggcgtcgcc gtgctctcgg cctatgccgg cctgcgctcg      480
gcggccctta acgtctacgt caacgccaag ggcctcgacg accgcgcctt cgccgaggag      540
cggctgaagg agctggaggg cctactggcc gaggcgggcg cgctcaacga gcggatctac      600
gagaccgtga agtccaaggt aaactga                                          627

<210> SEQ ID NO 9
<211> LENGTH: 867
<212> TYPE: DNA
<213> ORGANISM: Methylobacterium extorquens

<400> SEQUENCE: 9
atgtccaaga agctgctctt ccagttcgac accgatgcca cgccgagcgt cttcgacgtc       60
gtcgtcggct acgacggcgg tgccgaccac atcaccggct acggcaacgt cacgcccgac      120
aacgtcggcg cctatgtcga cggcacgatc tacacccgcg gcggcaagga gaagcagtcg      180
acggcgatct tcgtcggcgg cggcgacatg gcggccggcg agcgggtgtt cgaggcggtg      240
```

| | |
|---|---|
| aagaagcgct tcttcggccc gttccgcgtg tcctgcatgc tggattcgaa cggctccaac | 300 |
| acgaccgctg cggcgggcgt ggcgctcgtc gtcaaggcgg cgggcggctc ggtcaagggc | 360 |
| aagaaggccg tcgtgctcgc gggcaccggc ccggtcggca tgcgctcggc ggcgctgctt | 420 |
| gccggcgagg gcgccgaggt cgtgctgtgc gggcgcaagc tcgacaaggc gcaggccgcg | 480 |
| gccgattccg tgaacaagcg cttcaaggtg aacgtcaccg cggccgagac cgcggacgac | 540 |
| gcttcgcgtg ccgaggccgt gaagggcgcc catttcgtct tcaccgccgg tgcgatcggc | 600 |
| cttgaactgc tgccgcaggc agcctggcag aacgagagtt cgatcgagat cgtggccgac | 660 |
| tacaacgccc agccgccgct cggcatcggc gggatcgatg cgaccgacaa aggcaaggaa | 720 |
| tacggcggaa agcgcgcctt cggtgcgctc ggcatcggcg gcttgaagct caagctgcac | 780 |
| cgcgcctgca tcgccaagct gttcgagtcg agcgaaggcg tcttcgacgc cgaggagatc | 840 |
| tacaagctgg ccaaggaaat ggcctga | 867 |

<210> SEQ ID NO 10
<211> LENGTH: 945
<212> TYPE: DNA
<213> ORGANISM: Methylobacterium extorquens

<400> SEQUENCE: 10

| | |
|---|---|
| atgacaaaga aagtcgtctt cctcgatcgc gagtcgctcg acgcgaccgt gcgcgaattc | 60 |
| aacttcccgc acgagtacaa ggaatacgag tcgacctgga cgccgaggga gatcgtcgag | 120 |
| cgccttcagg gcgccgagat cgcgatgatc aacaaggtgc cgatgcgcgc cgacacgctg | 180 |
| aagcagcttc ccgacctgaa gctgatcgcg gtggctgcca cgggcacgga cgtcgtcgat | 240 |
| aaggctgcgg ccaaggcgca gggcatcacg gtcgtcaaca tccgcaacta cgccttcaac | 300 |
| accgtgcccg agcacgtggt cggcttgatg ttcgccctgc gccgggcgat cgtgccttac | 360 |
| gccaactcgg tgcgccgggg cgattggaac aagtcgaagc agttctgcta cttcgattac | 420 |
| ccgatctacg acatcgccgg ctcgacgctc ggcatcatcg gctacggcgc gctcggcaag | 480 |
| tcgatcgcca agcgggccga ggccctcggc atgaaggtgc tcgccttcga cgtgttcccg | 540 |
| caggacgggc tagtggatct cgatacgatc ctgacccagt ccgacgtcat cacgctgcac | 600 |
| gtgccgctga cgcccgacac caagaacatg atcggggccg agcagctcaa gaagatgaag | 660 |
| cggtccgcga tcctcatcaa caccgcccgc ggcgggctgg tggacgaggc ggccttgctc | 720 |
| caggcgctca aggacggcac catcggcggc gccggcttcg acgtcgtggc ccaggagccc | 780 |
| ccgaaggacg gcaacatcct ctgcgacgcc gacctgccga acctgatcgt caccccgcac | 840 |
| gtggcctggg cgagcaagga ggcgatgcag atcctcgccg accagctcgt ggacaacgtc | 900 |
| gaggccttcg tcgcgggcaa gccgcagaac gtcgtcgagg cgtaa | 945 |

<210> SEQ ID NO 11
<211> LENGTH: 2084
<212> TYPE: DNA
<213> ORGANISM: Roseobacter denitrificans

<400> SEQUENCE: 11

| | |
|---|---|
| atggatatcc acgagtacca agcgaaagaa gttcttgcta atttcggggt cgctgtgccg | 60 |
| gatggcgctt tggcgtacag cccggaacag gcatcctacc gcgcacgcga gctcggcggt | 120 |
| gaaagatggg ttgttaaggc ccagatacac gccggcgggc gcggcaaggc gggcggcgta | 180 |
| aaagtctgtg aaagcgacgt cgaaatccag aaagcatccg aagagatgtt tggcaaaaag | 240 |
| atgatcacgc atcagaccgg accagaaggc aaaggcatct accgcgtcta tgtcgaggct | 300 |

```
gcggtgccga tagatcgcga gatttatctg ggctttgttc ttgatcgtac gacgcaacgg      360
gtcatgatcg ttgcaagtgc cgaaggcggt atggagattg aagaaatctc tgaaaaacgc      420
cccgaaagca tcgttcgggc gattgtggag cctgccgttg gtctgcgcga atttcagtgc      480
cgccagattg cattcaaatt gggcgtcgat gcgggtctga cacagcagat ggtgcgtacc      540
ttgcaaggct gttatcgggc ttttaccgag ctggacgcga ccatggtgga gatcaaccct      600 tggtcatta ccgcagacaa tcgcgtgatt gcgctggatg ccaagatgac ttttgacgac      660
aatgcgttgt ccgccaccc acagatcagc gaattgcgcg acaaatcgca agaggatccg      720
cgcgaaagcc gggctgccga tcgcggtctg tcctatgtcg gtctggacgg caatatcggc      780
tgcatcgtga acggggctgg ccttgccatg gcgacgatgg acacgatcaa actggccggt      840
ggggagcctg cgaatttcct cgatatcggc ggtgggggcca cgcccgaacg tgtgccaag      900 gctttccggc tggtgctgtc ggacaagagc gtgcaggcga tcttggtcaa tatctttgca      960
gggatcaacc gctgtgactg ggtggccgaa ggcgtcgtgc aggccctcag ggaagtgcag     1020
gtcgatgtgc ccgtgatcgt gcgactggcc ggcaccaatg tggaggaagg cagaagatt      1080 ctcgcccaat ccggcctgcc gatcatccgc gcaaccactc tgatggaagc cgccgagcgc     1140
gcggtcggtg cgtggcagaa tgacctgtcg cagggtacaa gaatgagggc cgtatcatga     1200
gcatacttct tgatagcgac accaaagtca ttgtgcaggg catcaccggc aagatggccc     1260
gcttccacac caaggatatg ctcgaatacg gcactaacgt cgtcggtggc gtggtccctg     1320
gcaagggcgg cgaaacggtc gaaggcgtgc ctgtctttga caccgttgaa gaggcggtcg     1380
cgcaaaccgg ggcggaggcg tcgctggttt tcgtcccgcc gcctttcgcg gctgatagca     1440
ttatggaagc cgcagatgcg ggaattcagt actgcgtctg catcacggac ggtatccccg     1500
cacaggacat gatccgtgtg aaacgctaca tgtaccgcta tccgaaagag cgccgcatgg     1560
tgctcaccgg accaaactgt gccggcacga tcagcccggg caaggcgctg ctgggcatca     1620
tgccggggca tatctacctg caaggccacg tgggtatcgt gggacgttca ggcacgctgg     1680
gctatgaggc ggccgcacaa ctcaaggaac gcggcatcgg tgtttccact tcggtgggga     1740
ttggcggcga cccgatcaat ggttcatcgt tcaaagacat tctgcagcgt tttgaagaag     1800
acgaagacac ccatgtgatt gcgatgatcg gagagatcgg cggaccgcaa gaagcggaag     1860
cagccgaata catccgcgcg catgtgacca aaccggttgt ggcctatgtc gcgggcctga     1920
ccgctcctaa ggggcgcacc atgggccatg cgggcgcgat catctcggcc tttggcgaaa     1980
gtgcgagcga aaaggtcgaa atcctgtcgg cggcaggcgt cacggttgcc gaaaacccgg     2040
ctgtcatcgg tgagacaatc gccaaagtga tggaggccgc gtga                    2084
```

<210> SEQ ID NO 12
<211> LENGTH: 2090
<212> TYPE: DNA
<213> ORGANISM: Roseobacter denitrificans

<400> SEQUENCE: 12

```
atggatatcc acgaatacca agcaaaggaa attctcgcca gtttcggcgt agatgttccg       60
cccggtgcgt tggcctacag ccctgaacaa gcggcatatc gggcgcgcga acttggcggg      120
gaccgctggg tcgtcaaggc gcaggtgcac gcaggtggcc gcggcaaggc gggcggcgtg      180
aaggtgtgcg acagcgacgt cgagattcac aagacctgcg agggcctgtt tggccgcaag      240
ctggtgacgc atcagaccgg accggagggc aagggcattt accgcgtcta tgtcgaaggt      300
```

```
gccgtgccga tcgaacgcga gatttacctc gggttcgttc tggaccgcac gtcgcagcgt      360
gtcatgatcg tcgcctctgc cgaagggggc atggagatcg aggatatctc ggccgacaag      420
cccgacagca ttgtgcgcga caccgtggaa ccggcggttg gtctgcagga tttccaatgc      480
cgccagatcg cgttcaagct gggcattgat ccggccttga cgcagcgcat ggtgcgcacg      540
ttgcagggct gctaccgggc atttcgcgaa tatgacgcca cgatggtcga ggtcaatccg      600
ctcgttgtga ccggtgacaa tcgtattctg cgcctggatg ccaagatgac ctttgacgac      660
aacgcgttgt tccgccaccc acagatcagc gaattgcgcg acaaatcgca agaggacccg      720
cgcgaaagcc gggctgccga tcgcggtctg tcctatgttg gcctggacgg caatatcggc      780
tgcatcgtga acgggctggc cttgccatg gcgacgatgg acacgatcaa actggccggt       840
ggggagcctg cgaacttcct cgatatcggt ggtgggcca cgcccgaacg tgtggccaag        900
gctttccggc tggtgctgtc ggacaagagc gtgcaggcga tcctcgtcaa tatctttgcg      960
gggatcaacc gctgtgactg ggtggccgaa ggcgtcgtgc aggccctcag ggaggtgcag     1020
gtcgatgtgc ccgtaatcgt gcgactggcc ggcaccaacg tggaggaagg cagaagatc      1080
ctcgcccaat ccggcctgcc gatcatccgt gcaaccacat tgatggaagc cgccgagcgc     1140
gcggtcggtg cgtggcagaa tgaccttttcc caaaatacca aagtgaggct tgcgacatga    1200
gcatttttat tgatgcaaac acacccgtca tcgtgcaggg cattaccggc aagatggcgc     1260
gttttcacac ggctgacatg atcgcctatg gcaccaacgt cgtcggtggc gtggtccccg     1320
gcaagggcgg ccagacggtt gagggcgtgc cggttttcga tacagtcgag gacgcggtta     1380
ccgccaccgg ggcggaggcg tcgctggttt tcgtcccgcc gccttttgcg gctgacagca     1440
ttatggaagc cgcagatgcg ggaattcagt actgcgtctg catcacggac ggtatccccg     1500
cacaggacat gatccgtgtg aaacgctata tgtaccgcta tccaaaagac cgccgcatgg     1560
tgctcaccgg accgaattgc gctggcacga tcagcccggg caaggcgctg ctgggcatca     1620
tgccggggca tatctatctg cccggtcatg tgggcatcat cggacgctcc ggcacgttgg     1680
gctatgaggc cgctgctcag ctcaaggaac atgggatcgg cgtttcaacc tccgtcggaa     1740
tcggcggtga tccgatcaac ggatcgtcct ccgggacat ccttgagcgc ttcgaggccg      1800
atgatgaaac ccatgtgatc tgcatgatcg agagatcgg cgggccgcag aagccgaag       1860
ccgccgccta cattcgcgat cacgtcacca agccggtgat tgcctatgtt gcaggcctga     1920
ctgcaccgaa agggcgcacc atgggccatg cgggcgcgat catctccgcc tttggagaaa     1980
gtgcgagcga aaaggtcgaa atcctgtcgg cggcaggcgt cacggttgcc gaaaacccgg     2040
ccgtcattgg cgataccatt gccggcgtcc tgaggaagga ggccgcatga                2090
```

<210> SEQ ID NO 13
<211> LENGTH: 1233
<212> TYPE: DNA
<213> ORGANISM: Roseobacter denitrificans

<400> SEQUENCE: 13

```
atgacccaaa aaagcaacct gtctgccggg cgggagtatc tcgcgattcc ggggccttcc       60
gtaattcctg atgcggtatt gcaggccatg caccgcgcag cgccgaacat ctatgccggt      120
gccttgcctg acatgatgcc gggccttgtc gccgacctgc gccgcgttgc gcgcacccgc      180
catcatgttg cgatttacat cggcaacggg catgcggcat gggaggcagc actggccaat      240
gtcattggcg cgggggatcg ggtgctggtc cctgccacgg gcagttttgg ccatgattgg      300
ggggatatgg ccgcggggct tggggcagag gttgaaacgc tcgattttgg caaggcgtcg     360
```

```
gccatggata tggcgcggat cggcgaggcg ctcaaggcgg atagatcaca tgccatcaag    420
gcggttctgg cggtgcatgt ggacacatca agctcggtgc gcaatgatat tgcagccctg    480
cgcgcggtga tggatgaggc cgggcatccc gcgttgttga tggtggattg cattgcgtca    540
ctgggctgcg acgtgttcga gatgacgac tggggcgtgg atgtgatggt cactgcctgt    600 caaaagggc tgatggtgcc accgggcatg gctttcgtct ttttcaacga caaggctggc    660
gaggttcgac ggcaaatgcc gagggtcagc cgctattggg attggacccc gcgcgccgca    720
cctgacctgt tttatcaata ctggaacggg acagcgccca cgcatcatgt ctacggtctg    780
cgggctgcct tggacatgat ccacgccgaa ggaatcgaag ctgtgtggcg cgtcacgaa     840 gtgctcgcac atgcgatctg gcggcttgc agcgcatggg gcgcaggtgg cagtctggcc    900
ttcaatgtgg ccgaaccgga tgcgcgcagc cgggctgtta cgtcactgaa acttgaaagc    960
ccgcaggcca ccgcgctgcg cgactggact gaaaaccagc ttggcttgac ccttggcatc   1020
ggacttggca tggcgacacg gggcgatccg gcatggcatg ggttttccg gttgggtcac    1080 atgggtcaca tcaacggcca catgatcatg gggatgctcg gcggcgtgga tgcgggtttg   1140
aaagcgctgg acattccgca cgggccgggc gcgcttgagg ctgcatccac cgtgattgcc   1200
accggtcagt tgtcggcggg ggcgtcggag tag                                 1233

<210> SEQ ID NO 14
<211> LENGTH: 858
<212> TYPE: DNA
<213> ORGANISM: Rhodobacter sphaeroides

<400> SEQUENCE: 14
atggcgcatc aggctcatcc cttccgctcc gtgctctaca ttcccggctc gaaggagcgg     60
gcgctggaga aggcgcaggg ccttgccgcc gatgcgatca tcttcgacct cgaggatgct    120
gtcgcccatg acgagaagat ccacgcgcgc gcgctcctga agaccacgct cgagaccgtc    180
gattacggcc atcgcttccg catcgtgagg gtgaacggga tggacaccga gtggggccgc    240
gcggatctcg aggccttcgc ggaggcaaag gcggacgcga tcctcattcc caaggtctcg    300
cgggcggcgg atctggaggc ggtggcggcc ctcgtgcccg acctgccgct ctgggccatg    360
atggagacgg cgcagggcat gctcaacgcc gccgagatcg cggcccaccc gcgcctcacc    420
ggcatggtga tgggcacgaa cgacctcgcc aaggagctcg gcagccgcta ccggcccgac    480
cgtctggcga tgcaggcggg gctcggcctc tgcctgctcg cggcccgcgc ccatgggctc    540
accatcgtcg acgcgtcta caatgccttc aaggacgagg agggcctgcg ggccgaatgc    600
gagcagggcc gcgacatggg cttcgacggc aagacgctga tccatcccgc ccagctcgag    660
atcgcgaacg cggtcttttc gccctcgccg gccgagatcg agctggccaa cgccagatc    720 gccgccttcg aggaggcaga acgccacggg cagggcgtgg ccgttgtgga tgcaagatc    780 gtcgagaacc tgcatatcgt gaccgcgcgg cagactctgg ccaaggccga ggcgattgcc    840
gcgttcaggg caagctga                                                   858

<210> SEQ ID NO 15
<211> LENGTH: 957
<212> TYPE: DNA
<213> ORGANISM: Rhodobacter sphaeroides

<400> SEQUENCE: 15
atgagcttcc gccttcagcc cgcgccgcct gcccgtccga accgctgcca gctgttcggc     60
```

```
cccggctccc ggcccgcgct gttcgagaag atggcggcct ccgcggcgga cgtgatcaac      120
ctcgacctcg aggattcggt ggcgcccgac gacaaggcgc aggcccgcgc gaacatcatc      180
gaggcgatca acgggctcga ctggggccgc aagtatctct cggtccgcat caacggtctg      240
gacacgccct tctggtatcg cgacgtcgtg gacctgctcg aacaggcggg cgaccggctc      300
gaccagatca tgatcccgaa ggtcggctgc gcggcggatg tttatgcggt cgatgctctg      360
gtcacggcca tcgagcgcgc caagggccgc accaagcccc tgagcttcga ggtcatcatc      420
gaatcggccg cgggcatcgc ccatgtcgag gaaatcgcgg cctcctcgcc gcgcctgcag      480
gccatgagcc tcgcgccgc cgatttcgca gcctcgatgg ggatgcagac gacaggtatc       540
ggtggcacgc aggaaaacta ctacatgttg catgacgggc agaagcactg gtcggacccg      600
tggcactggg cgcaggcggc catcgtggcg gcctgccgga cccacgggat cctgccggtg      660
gacggcccgt tcggcgattt ttccgacgat gagggcttcc gcgcgcaggc ccgccgctcg      720
gccactctgg ggatggtggg caaatgggcc atacatccca aacaggtggc cctcgcgaac      780
gaagttttca ccccttccga cggccgtg accgaagcgc gcgagatcct cgcggcgatg       840
gatgcggcca aggcgagggg cgagggcgcc acggtctaca agggaagact tgttgacatc      900
gcgtccatca aacaggcaga agtgatcgta aggcaggcag aaatgatctc ggcctga        957

<210> SEQ ID NO 16
<211> LENGTH: 1203
<212> TYPE: DNA
<213> ORGANISM: Rhodobacter sphaeroides

<400> SEQUENCE: 16
atgtcgcttg cgcacggccg tccctatctt gccattcccg gcccctccgc catgccggac       60
cgggtgctga cgccatgca ccgtgccgcg cccaacatct acgaaggcgc cctgcacgag       120
atggtggcca gcctctggcc ggatctgaag cgcattgccg gcaccgagca tcaggtggcg      180
ctctatatcg cgaacggcca cggcgcgtgg gaggcggcga acgccaacct cttcagccgc      240
ggcgaccggg cgctggtgct ggccaccggc cgcttcggtc acggctgggc cgagagcgcc      300
cgcgcgctcg gcgtcgatgt gcagctgatc gacttcggcc gggccgcgcc cgccgatccc      360
gcccggctgg aggaggcgct gcgggcggac cccgggcatc ggatcaaggc ggtgctggtg      420
acccatgtcg acacgccac ctcgatccgc aacgacgtgg ccgcgctccg cgccgccatc      480
gatgccgtgg gccatccggc gctgctcgcg gtcgattgca tcgcctcgct cgcctgcgac      540
gaatatcgca tggacgaatg ggggggccgac gtgaccgtcg gcgcgagcca gaagggggttg     600 atgaccccgc cggggctggg cttcgtctgg tattccgacc gcgcgctgga acggtgccgc      660
gcctcggatc tgcgcacgcc ctactgggac tggacgcccc gcagcttcgg caccgaattc      720
tggcagcatt tctgcggcac cgcgccgacg catcacctct acgggttgcg gcggcgctc       780 gacatgatcc tcgaggaggg actgcccgcg gtctgggcgc ccacgaggc gctggcgcgg       840 gcggtctgga cggccttcga ccgctggggc gcggcaatc ccgagatcgc gctcaacgtg       900
gccgatgccg cgtgccgcgg ccgctcggtg acggcggccc ggatgggcgc gccccatgcg      960
acgcggctgc gggaatggac cgagacgcgg cgggcgtga cgctcggcat cggcctcggc       1020
atggcgctgc cctcggagcc cgcctaccac gggttcctcc gcgtcgcgca catgggccat      1080
gtaaacgccc acatgacgct cggcgcgctc gcggtgatgg aggcgggcct cgcagcgctc      1140
gagatcccgc acggggaggg ggcgctggcc gctgccgccg ccagcctcgg cgcggcggcc      1200
tga                                                                    1203
```

<210> SEQ ID NO 17
<211> LENGTH: 1368
<212> TYPE: DNA
<213> ORGANISM: Chloroflexus aurantiacus

<400> SEQUENCE: 17

| | | | | | |
|---|---|---|---|---|---|
| atggcgaaag | cttcgcgcct | gacacgttcc | acaggtcagc | cgacggaagt | ttccgaagga | 60 |
| caggtgaccg | ggacctctga | aatgccacca | actggcgaag | agccctcagg | gcatgccgaa | 120 |
| tccaagcctc | ccgcatcaga | ccctatgtct | accccggaa | ccggtcagga | caacttcca | 180 |
| ctgtcgggca | ttcgcgtcat | tgacgttggg | aacttttgg | ctggacctta | cgcggcgtct | 240 |
| attttgggtg | agtttggagc | cgaagttctt | aaaattgaac | accctcttgg | gggcgacccc | 300 |
| atgcgccgct | tcggtacagc | cacagcccgc | catgacgcca | ccttggcctg | gctgtctgaa | 360 |
| gcccgcaacc | gcaagagcgt | gactattgac | ttgcgtcaac | aggaaggggt | tgcattgttc | 420 |
| ttaaagttgg | ttgcaaagag | cgatattctt | atcgagaact | tcgtcctgg | aacaatggaa | 480 |
| gagtggggat | taagttggcc | tgtgttgcaa | gcgaccaatc | cgggcttgat | tatgcttcgc | 540 |
| gtgtctggtt | acggccaaac | gggcccatat | cgccgtcgtt | cagggttcgc | tcatatcgct | 600 |
| catgctttct | ctgggctttc | ctatttagct | gggttccccg | gcgaaacacc | tgtgttacca | 660 |
| ggcaccgcac | cattaggtga | ttatattgca | tctttatttg | gggcaattgg | tatcttgatt | 720 |
| gcgttacgtc | acaaagagca | aactggccgt | ggccaattga | ttgacgtggg | catctatgaa | 780 |
| gccgtattcc | gtattttaga | tgaaattgcg | ccagcttatg | gcttgttcgg | taaaattcgt | 840 |
| gagcgtgagg | gtgcagggtc | ttttattgca | gtgcctcatg | gtcactttcg | cagcaaagac | 900 |
| ggtaagtggg | tggccattgc | atgcactact | gacaaaatgt | tgaacgtct | tgcagaagcc | 960 |
| atggaacgtc | cagagttagc | atcccctgaa | ttgtatggag | atcaacgcaa | acgtctggcc | 1020 |
| gcgcgcgaca | tcgtaaacca | aatcacaatt | gaatgggtag | ggagcctgac | acgtgatgaa | 1080 |
| gttatgcgcc | gctgcttgga | aaaagaggtg | ccggtgggac | cattaaactc | aattgctgac | 1140 |
| atgttcaatg | acgagcactt | tcttgcccgc | ggtaatttcg | cttgcattga | agcggaaggc | 1200 |
| atcggagaag | tagttgttcc | gaacgtcatc | ccacgtcttt | cggagacacc | gggtcgcgtt | 1260 |
| actaatttgg | gcccaccttt | gggaaatgcc | acgtatgagg | tactgcgtga | actgttagac | 1320 |
| atttccgcgg | aggagatcaa | gcgcttacgc | agccgtaaga | ttatctag | | 1368 |

<210> SEQ ID NO 18
<211> LENGTH: 1218
<212> TYPE: DNA
<213> ORGANISM: Chloroflexus aurantiacus

<400> SEQUENCE: 18

| | | | | | |
|---|---|---|---|---|---|
| atggacggga | ctactaccac | cttaccactg | gccggtatcc | gcgtcatcga | cgcggctaca | 60 |
| gttatcgccg | caccgttctg | cgctacgctt | tgggtgagt | ttggtgctga | cgtcttaaag | 120 |
| gtcgaacatc | ccatcggagg | ggatgccttg | cgccgttttg | gtacgccaac | cgcgcgtggc | 180 |
| gacacgctta | catggcttag | tgaatctcgt | aataaacgtt | ccgtgaccct | gaatcttcag | 240 |
| cacccggaag | gggctcgtgt | tttcaaagag | cttattgctc | atagcgatgt | tttgtgcgag | 300 |
| aacttccgtc | ccggaacatt | agaaaaatgg | ggtttgggtt | gggatgtcct | ttccaaaatc | 360 |
| aatccgcgcc | ttatcatgct | gcgcgtaact | ggatacggcc | agacgggacc | ataccgcgac | 420 |
| cgtccgggtt | tcgcccgcat | tgctcacgca | gtcggtggta | ttgcgtattt | ggctggcatg | 480 |

```
cccaaaggta cgccagtaac gcctgggtct acaacgttgg ccgattacat gacgggtttg      540
tatggttgca ttggcgttct gcttgctctg cgccaccgtg aacaaacggg gcgcggccaa      600
tacatcgacg ccgcattata cgaaagcgtc ttccgctgct cagacgagct ggtacctgcc      660
tacggaatgt accgtaaagt acgcgaacgt cacggttcac actacaacga attcgcttgt      720
cctcatggac atttccaaac gaaagatggt aaatgggtag caattagctg cgcgactgac      780
aagttattcg cgcgtctggc taatgccatg ggccgcccgg aacttgcctc ctcgagcgtc      840
tacggagacc agaaggtgcg tttggcccac gcgagcgatg ttaacgaaat cgtccgcgac      900
tggtgttcta gcctgacccg tgccgaggtc ctggaacgct gctacgctac ggccacgccc      960
gccgcgcctt tgaacgatat tgctgatttc ttcggtgacc gccatgtgca cgctcgccgt     1020
aacttagtag ctatcgatgc tgaagattta ggagaaacct tgattatgcc gaatgtagta     1080
cccaagttat ccgagacacc gggaagtatc cgcagtttag gacctaaatt aggagaacat     1140
accgaggagg tattaaagga aattttaggt atgtgtgatg aacaaatcaa tgacctgcgt     1200
tccaaacgtg tcatttag                                                    1218

<210> SEQ ID NO 19
<211> LENGTH: 906
<212> TYPE: DNA
<213> ORGANISM: Acetobacterium woodii

<400> SEQUENCE: 19
atggcagcaa aattattaag tggaaaagaa gttagcgagt caatgctcgc tgaagtacta       60
aaagatgcga atgaattaaa agcaaaaggc attaccgtaa aatggcaat catgcgcgtt      120 ggtgaagacc caggttccat ttcttatgaa aaaagtatta tcaccagaat gggaaaatca      180
aatatcgaag ttgaatcggt acaattccca attgatgtaa cagaagctga ttttattgcc      240
aaacttcaat caatcaacga agataaaaac attcattcag tattaatatt ccaacctctt      300
cccgatcaaa tcgacgctga aaaaataaaa tatctgttaa gtcctgaaaa agatccagat      360
gctcttaatc caacaaactt aggaaaacta atgattgctg atgaagagg atttttttcca      420 tgtaccgctg aaggcgttat ggaaatgttt aaattctata atattgatgt taagggcaaa      480
gacgttgttg ttattaacaa ctctaacgtg ttaggaaaac cactgacaat tatgttaaca      540
aacgaattcg caaccgtcac aatgtgtcat gtatttacaa aagatacggc ttcttacacc      600
aagaaagccg atattgttgt aaccgcatgt ggtatttacg gtttggttaa accagacatg      660
ttaagcgaag attgtatttt aattgacgtg gcaatggctc aaatgaaaga tgaaaacaaa      720
gaatttgttt taaatgaaga aggcaagaaa atcagaacgg gtgatgctca tgttgactgt      780
ttaaacaaag tcgcaatgat tacttctgct accccaggtt gtggcggtgg aaccggtcca      840
attaccacag ctttattagc taaacatgtg atcaaagcct gtaaaatgca aaacggctta      900
ttatag                                                                 906

<210> SEQ ID NO 20
<211> LENGTH: 1617
<212> TYPE: DNA
<213> ORGANISM: Mannheimia succiniciproducens

<400> SEQUENCE: 20
atgacagatc ttaatcaatt aactcaagaa cttggtgctt taggtattca tgatgtacaa       60
gaagttgtgt ataccccgag ctatgaactt ctttttgcgg aagaaaccaa accaggttta      120
gaaggttatg aaaaaggtac tgtgactaat caaggagcgg ttgctgtaaa taccggtatt      180
```

```
ttcaccggtc gttctccgaa agataaatat atcgttttag acgacaaaac taaagatacc    240
gtatggtgga ccagcgaaaa agttaaaaac gataacaaac caatgagcca agatacctgg    300
aacagtttga aaggtttagt tgccgatcaa ctttccggta aacgtttatt tgttgttgac    360
gcattctgcg gcgcgaataa agatacgcgt ttagctgttc gtgtggttac tgaagttgca    420
tggcaggcgc attttgtaac aaatatgttt atccgccctt cagcggaaga attaaaaggt    480
ttcaaacctg atttcgtggt aatgaacggt gcaaaatgta caaatcctaa ctggaaagaa    540
caagggttaa attccgaaaa cttcgttgcg ttcaacatta cagaaggcgt tcaattaatc    600
ggcggtactt ggtacggtgg tgaaatgaaa aaaggtatgt tctcaatgat gaactacttc    660
ttaccgcttc gtggtattgc atcaatgcac tgttccgcaa acgttggtaa agacggcgat    720
accgcaattt tcttcggttt gtcaggcaca ggtaaaacga cattatcaac agatcctaaa    780
cgtcaactaa tcggtgatga cgaacacggt tgggacgatg aaggcgtatt taacttcgaa    840
ggtggttgct acgcgaaaac cattaactta tccgctgaaa acgagccgga tatctatggc    900
gctatcaaac gtgacgcatt attggaaaac gtggttgttt tagataacgg tgacgttgac    960
tatgcagacg gttccaaaac agaaaataca cgtgtttctt atccgattta tcacattcaa   1020
aatatcgtta aacctgtttc taaagctggt ccggcaacta aagttatctt cttgtctgcc   1080
gatgcattcg gtgtattacc gccggtgtct aaattaactc cggaacaaac caaatactat   1140
ttcttatccg gtttcactgc gaaattagcg ggtacggaac gcggtattac agagcctaca   1200
ccaacattct ctgcatgttt tggtgcggct tttttaagct tgcatccgac acaatatgcc   1260
gaagtgttag taaaacgtat gcaagaatca ggtgcggaag cgtatcttgt taatacaggt   1320
tggaacggta ccggcaaacg tatctcaatt aaagataccc gtggtattat tgatgcaatt   1380
ttagacggct caattgataa agcggaaatg ggctcattac caatcttcga tttctcaatt   1440
cctaaagcat tacctggtgt taaccctgca atcttagatc cgcgcgatac ttatgcggat   1500
aaagcgcaat gggaagaaaa agctcaagat cttgcaggtc gctttgtgaa aaactttgaa   1560
aaatataccg gtacggcgga aggtcaggca ttagttgctg ccggtcctaa agcataa      1617
```

<210> SEQ ID NO 21
<211> LENGTH: 1206
<212> TYPE: DNA
<213> ORGANISM: Arabidopsis thaliana

<400> SEQUENCE: 21

```
atggactata tgtatggacc agggagacac catctgtttg taccaggacc agtgaacata     60
ccggaaccgg taatccgggc gatgaaccgg aacaacgagg attaccggtc accagccatt    120
ccggcgctta cgaaaacatt gttggaggat gttaagaaga tattcaagac cacatcaggg    180
acaccttttc tgtttcccac gaccgggact ggtgcttggg agagtgcctt gaccaacacg    240
ttatctcctg gagacaggat tgtttcgttt ctgattggac aatttagctt gctctggatt    300
gaccagcaga agaggcttaa tttcaatgtt gatgtggttg agagtgattg gggacaaggt    360
gctaatctcc aagtcttggc ctcaaagctc tcacaagacg agaatcatac catcaaagcc    420
atttgcattg tccacaacga gaccgcgacc ggagttacca atgacatctc tgctgtccgc    480
acactcctcg atcactacaa gcatccggct ttgctgctag tggacggtgt ttcgtccatc    540
tgcgcgcttg atttccgaat ggatgagtgg ggagtggacg tggccttgac tgggtctcag    600
aaagccttat ctcttccaac aggacttggt attgtctgcg ccagtcctaa agctttggaa    660
```

-continued

```
gctaccaaaa cttctaaatc tctcaaagta ttctttgact ggaatgacta ccttaagttt      720
tacaagctag gaacctattg gccatacaca ccttccattc aacttctcta cggtcttaga      780
gctgctcttg atcttatctt tgaggaagga cttgagaaca tcatcgcccg ccatgctcgt      840
ttgggaaagg ccaccaggct tgcggtggaa gcatggggc tgaaaaactg cacacagaag       900
gaggaatgga taagtaacac agtgacagca gttatggtgc ctccgcatat agacggttcg      960
gagattgtga aagggcatg gcagaggtac aacttaagtc ttggtcttgg tctcaacaaa      1020
gtggctggaa aggttttcag aattggacat ctaggaaatg tgaatgagtt gcaacttctc     1080
gggtgtcttg cggagtgga gatgatactg aaggatgttg atacccagt tgtaatggga      1140
agtggagttg cagctgcctc tacttatctt cagcaccaca ttcctctcat tccctctaga    1200
atctaa                                                                1206

<210> SEQ ID NO 22
<211> LENGTH: 2283
<212> TYPE: DNA
<213> ORGANISM: Escherichia coli

<400> SEQUENCE: 22
atgtccgagc ttaatgaaaa gttagccaca gcctgggaag ttttaccaa aggtgactgg       60
cagaatgaag taaacgtccg tgacttcatt cagaaaaact acactccgta cgagggtgac     120
gagtccttcc tggctggcgc tactgaagcg accaccaccc tgtgggacaa agtaatggaa     180
ggcgttaaac tggaaaaccg cactcacgcg ccagttgact ttgacaccgc tgttgcttcc     240
accatcacct ctcacgacgc tggctacatc aacaagcagc ttgagaaaat cgttggtctg     300
cagactgaag ctccgctgaa acgtgctctt atcccgttcg gtggtatcaa aatgatcgaa     360
ggttcctgca aagcgtacaa ccgcgaactg gatccgatga tcaaaaaaat cttcactgaa     420
taccgtaaaa ctcacaacca gggcgtgttc gacgtttaca ctccggacat cctgcgttgc     480
cgtaaatctg tgttctgac cggtctgcca gatgcatatg gccgtggccg tatcatcggt     540
gactaccgtc gcgttgcgct gtacggtatc gactacctga tgaaagacaa actggcacag     600
ttcacttctc tgcaggctga tctggaaaac ggcgtaaacc tggaacagac tatccgtctg     660
cgcgaagaaa tcgctgaaca gcaccgcgct ctgggtcaga tgaaagaaat ggctgcgaaa     720
tacggctacg acatctctgg tccggctacc aacgctcagg aagctatcca gtggacttac     780
ttcggctacc tggctgctgt taagtctcag aacggtgctg caatgtcctt cggtcgtacc     840
tccaccttcc tggatgtgta catcgaacgt gacctgaaag ctggcaagat caccgaacaa     900
gaagcgcagg aaatggttga ccacctggtc atgaaactgc gtatggttcg cttcctgcgt     960
actccggaat acgatgaact gttctctggc gacccgatct gggcaaccga atctatcggt    1020
ggtatgggcc tcgacggtcg taccctggtt accaaaaaca gcttccgttt cctgaacacc    1080
ctgtacacca tgggtccgtc tccggaaccg aacatgacca ttctgtggtc tgaaaaactg    1140
ccgctgaact tcaagaaatt cgccgctaaa gtgtccatcg acacctcttc tctgcagtat    1200
gagaacgatg acctgatgcg tccggacttc aacaacgatg actacgctat gcttgctgc    1260
gtaagcccga tgatcgttgg taaacaaatg cagttcttcg gtgcgcgtgc aaacctggcg    1320
aaaaccatgc tgtacgcaat caacggcggc gttgacgaaa aactgaaaat gcaggttggt    1380
ccgaagtctg aaccgatcaa aggcgatgtc ctgaactatg atgaagtgat ggagcgcatg    1440
gatcacttca tggactggct ggctaaacag tacatcactg cactgaacat catccactac    1500
atgcacgaca agtacagcta cgaagcctct ctgatggcgc tgcacgaccg tgacgttatc    1560
```

```
cgcaccatgg cgtgtggtat cgctggtctg tccgttgctg ctgactccct gtctgcaatc    1620
aaatatgcga aagttaaacc gattcgtgac gaagacggtc tggctatcga cttcgaaatc    1680
gaaggcgaat acccgcagtt tggtaacaat gatccgcgtg tagatgacct ggctgttgac    1740
ctggtagaac gtttcatgaa gaaaattcag aaactgcaca cctaccgtga cgctatcccg    1800
actcagtctg ttctgaccat cacttctaac gttgtgtatg gtaagaaaac gggtaacacc    1860
ccagacggtc gtcgtgctgg cgcgccgttc ggaccgggtg ctaacccgat gcacggtcgt    1920
gaccagaaag gtgcagtagc ctctctgact tccgttgcta aactgccgtt tgcttacgct    1980
aaagatggta tctcctacac cttctctatc gttccgaacg cactgggtaa agacgacgaa    2040
gttcgtaaga ccaacctggc tggtctgatg gatggttact ccaccacga agcatccatc    2100 gaaggtggtc agcacctgaa cgttaacgtg atgaaccgtg aaatgctgct cgacgcgatg    2160
gaaaacccgg aaaaatatcc gcagctgacc atccgtgtat ctggctacgc agtacgtttc    2220
aactcgctga ctaaagaaca gcagcaggac gttattactc gtaccttcac tcaatctatg    2280
taa                                                                  2283

<210> SEQ ID NO 23
<211> LENGTH: 53
<212> TYPE: DNA
<213> ORGANISM: Artificial Sequence
<220> FEATURE:
<223> OTHER INFORMATION: Forward primer for mtkA amplification

<400> SEQUENCE: 23
ttgttgagac acttacacga aggaggaatt catggacgtt cacgagtacc aag          53

<210> SEQ ID NO 24
<211> LENGTH: 20
<212> TYPE: DNA
<213> ORGANISM: Artificial Sequence
<220> FEATURE:
<223> OTHER INFORMATION: Reverse primer for mtkA amplification

<400> SEQUENCE: 24
tcagtgcttg gcgccgtggc                                                20

<210> SEQ ID NO 25
<211> LENGTH: 51
<212> TYPE: DNA
<213> ORGANISM: Artificial Sequence
<220> FEATURE:
<223> OTHER INFORMATION: Forward primer for mtkB amplification

<400> SEQUENCE: 25
tgccacggcg ccaagcactg aaggaggaat tcatgagcat tctcatcgac g             51

<210> SEQ ID NO 26
<211> LENGTH: 18
<212> TYPE: DNA
<213> ORGANISM: Artificial Sequence
<220> FEATURE:
<223> OTHER INFORMATION: Reverse primer for mtkB amplification

<400> SEQUENCE: 26
tcacgccgcg cgggcgag                                                  18

<210> SEQ ID NO 27
<211> LENGTH: 50
<212> TYPE: DNA
```

```
<213> ORGANISM: Artificial Sequence
<220> FEATURE:
<223> OTHER INFORMATION: Forward primer for mcl amplification

<400> SEQUENCE: 27
ctcgcccgcg cggcgtgaag gaggaattca tgagcttcac cctgatccag           50

<210> SEQ ID NO 28
<211> LENGTH: 19
<212> TYPE: DNA
<213> ORGANISM: Artificial Sequence
<220> FEATURE:
<223> OTHER INFORMATION: Reverse primer for mcl amplification

<400> SEQUENCE: 28
ttactttccg cccatcgcg                                             19

<210> SEQ ID NO 29
<211> LENGTH: 50
<212> TYPE: DNA
<213> ORGANISM: Artificial Sequence
<220> FEATURE:
<223> OTHER INFORMATION: Forward primer for sga amplification

<400> SEQUENCE: 29
cgcgatgggc ggaaagtaaa ggaggaattc atggcggcaa cgagacgtcc           50

<210> SEQ ID NO 30
<211> LENGTH: 19
<212> TYPE: DNA
<213> ORGANISM: Artificial Sequence
<220> FEATURE:
<223> OTHER INFORMATION: Reverse primer for sga amplification

<400> SEQUENCE: 30
tcaagccttg gcgagcggg                                             19

<210> SEQ ID NO 31
<211> LENGTH: 51
<212> TYPE: DNA
<213> ORGANISM: Artificial Sequence
<220> FEATURE:
<223> OTHER INFORMATION: Forward primer for ftfL amplification

<400> SEQUENCE: 31
cccgctcgcc aaggcttgaa ggaggaattc atgccctcag atatcgagat c         51

<210> SEQ ID NO 32
<211> LENGTH: 19
<212> TYPE: DNA
<213> ORGANISM: Artificial Sequence
<220> FEATURE:
<223> OTHER INFORMATION: Reverse primer for ftfL amplification

<400> SEQUENCE: 32
ctagaacagc ccgtcgatc                                             19

<210> SEQ ID NO 33
<211> LENGTH: 51
<212> TYPE: DNA
<213> ORGANISM: Artificial Sequence
<220> FEATURE:
<223> OTHER INFORMATION: Forward primer for fch amplification

<400> SEQUENCE: 33
gatcgacggg ctgttctaga ggaggaattc atggccggca acgagacgat c         51
```

<210> SEQ ID NO 34
<211> LENGTH: 21
<212> TYPE: DNA
<213> ORGANISM: Artificial Sequence
<220> FEATURE:
<223> OTHER INFORMATION: Reverse primer for fch amplification

<400> SEQUENCE: 34
tcagtttacc ttggacttca c                                          21

<210> SEQ ID NO 35
<211> LENGTH: 53
<212> TYPE: DNA
<213> ORGANISM: Artificial Sequence
<220> FEATURE:
<223> OTHER INFORMATION: Forward primer for mtdA amplification

<400> SEQUENCE: 35
gtgaagtcca aggtaaactg aaggaggaat tcatgtccaa gaagctgctc ttc        53

<210> SEQ ID NO 36
<211> LENGTH: 40
<212> TYPE: DNA
<213> ORGANISM: Artificial Sequence
<220> FEATURE:
<223> OTHER INFORMATION: Reverse primer for mtdA amplification

<400> SEQUENCE: 36
tcatccgcca aaacagccaa gtcaggccat ttccttggcc                       40

<210> SEQ ID NO 37
<211> LENGTH: 52
<212> TYPE: DNA
<213> ORGANISM: Artificial Sequence
<220> FEATURE:
<223> OTHER INFORMATION: Forward primer for hprA amplification

<400> SEQUENCE: 37
ttgttgagac acttacacga aggaggaatt catgacaaag aaagtcgtct tc         52

<210> SEQ ID NO 38
<211> LENGTH: 42
<212> TYPE: DNA
<213> ORGANISM: Artificial Sequence
<220> FEATURE:
<223> OTHER INFORMATION: Reverse primer for hprA amplification

<400> SEQUENCE: 38
tcatccgcca aaacagccaa gttacgcctc gacgacgttc tg                    42

<210> SEQ ID NO 39
<211> LENGTH: 53
<212> TYPE: DNA
<213> ORGANISM: Artificial Sequence
<220> FEATURE:
<223> OTHER INFORMATION: Forward primer for mtkAB1 amplification

<400> SEQUENCE: 39
ttgttgagac acttacacga aggaggaatt catggatatc cacgaatacc aag        53

<210> SEQ ID NO 40
<211> LENGTH: 21
<212> TYPE: DNA
<213> ORGANISM: Artificial Sequence
<220> FEATURE:

<223> OTHER INFORMATION: Reverse primer for mtkAB1 amplification

<400> SEQUENCE: 40
tcatgcggcc tccttcctca g                                          21

<210> SEQ ID NO 41
<211> LENGTH: 53
<212> TYPE: DNA
<213> ORGANISM: Artificial Sequence
<220> FEATURE:
<223> OTHER INFORMATION: Forward primer for mtkAB2 amplification

<400> SEQUENCE: 41
ttgttgagac acttacacga aggaggaatt catggatatc catgaatacc aag        53

<210> SEQ ID NO 42
<211> LENGTH: 22
<212> TYPE: DNA
<213> ORGANISM: Artificial Sequence
<220> FEATURE:
<223> OTHER INFORMATION: Reverse primer for mtkAB2 amplification

<400> SEQUENCE: 42
tcacgcggcc tccatcactt tg                                         22

<210> SEQ ID NO 43
<211> LENGTH: 52
<212> TYPE: DNA
<213> ORGANISM: Artificial Sequence
<220> FEATURE:
<223> OTHER INFORMATION: Forward primer for sga amplification

<400> SEQUENCE: 43
ttgttgagac acttacacga aggaggaatt catgacccaa aaaagcaacc tg         52

<210> SEQ ID NO 44
<211> LENGTH: 41
<212> TYPE: DNA
<213> ORGANISM: Artificial Sequence
<220> FEATURE:
<223> OTHER INFORMATION: Reverse primer for sga amplification

<400> SEQUENCE: 44
tcatccgcca aaacagccaa gctactccga cgcccccgcc g                    41

<210> SEQ ID NO 45
<211> LENGTH: 51
<212> TYPE: DNA
<213> ORGANISM: Artificial Sequence
<220> FEATURE:
<223> OTHER INFORMATION: Forward primer for mcl1 amplification

<400> SEQUENCE: 45
ttgttgagac acttacacga aggaggaatt catggcgcat caggctcatc c         51

<210> SEQ ID NO 46
<211> LENGTH: 20
<212> TYPE: DNA
<213> ORGANISM: Artificial Sequence
<220> FEATURE:
<223> OTHER INFORMATION: Reverse primer for mcl1 amplification

<400> SEQUENCE: 46
tcagcttgcc ctgaacgcgg                                            20

```
<210> SEQ ID NO 47
<211> LENGTH: 51
<212> TYPE: DNA
<213> ORGANISM: Artificial Sequence
<220> FEATURE:
<223> OTHER INFORMATION: Forward primer for mcl2 amplification

<400> SEQUENCE: 47
ccgcgttcag ggcaagctga aggaggaatt catgagcttc cgccttcagc c          51

<210> SEQ ID NO 48
<211> LENGTH: 20
<212> TYPE: DNA
<213> ORGANISM: Artificial Sequence
<220> FEATURE:
<223> OTHER INFORMATION: reverse primer for mcl2 amplification

<400> SEQUENCE: 48
tcaggccgag atcatttctg                                              20

<210> SEQ ID NO 49
<211> LENGTH: 51
<212> TYPE: DNA
<213> ORGANISM: Artificial Sequence
<220> FEATURE:
<223> OTHER INFORMATION: Forward primer for sga amplification

<400> SEQUENCE: 49
ttgttgagac acttacacga aggaggaatt catgtcgctt gcgcacggcc g           51

<210> SEQ ID NO 50
<211> LENGTH: 41
<212> TYPE: DNA
<213> ORGANISM: Artificial Sequence
<220> FEATURE:
<223> OTHER INFORMATION: Reverse primer for sga amplification

<400> SEQUENCE: 50
tcatccgcca aaacagccaa gtcaggccgc cgcgccgagg c                      41

<210> SEQ ID NO 51
<211> LENGTH: 20
<212> TYPE: DNA
<213> ORGANISM: Artificial Sequence
<220> FEATURE:
<223> OTHER INFORMATION: Forward primer for smtA amplification

<400> SEQUENCE: 51
ttgttgagac acttacacga                                              20

<210> SEQ ID NO 52
<211> LENGTH: 20
<212> TYPE: DNA
<213> ORGANISM: Artificial Sequence
<220> FEATURE:
<223> OTHER INFORMATION: Reverse primer for smtA amplification

<400> SEQUENCE: 52
ctagataatc ttacggctgc                                              20

<210> SEQ ID NO 53
<211> LENGTH: 20
<212> TYPE: DNA
<213> ORGANISM: Artificial Sequence
<220> FEATURE:
<223> OTHER INFORMATION: Forward primer for smtB amplification
```

<400> SEQUENCE: 53
gcagccgtaa gattatctag          20

<210> SEQ ID NO 54
<211> LENGTH: 20
<212> TYPE: DNA
<213> ORGANISM: Artificial Sequence
<220> FEATURE:
<223> OTHER INFORMATION: Reverse primer for smtB amplification

<400> SEQUENCE: 54
ctaaatgaca cgtttggaac          20

<210> SEQ ID NO 55
<211> LENGTH: 52
<212> TYPE: DNA
<213> ORGANISM: Artificial Sequence
<220> FEATURE:
<223> OTHER INFORMATION: Forward primer for folD amplification

<400> SEQUENCE: 55
gtgaagtcca aggtaaactg aaggaggaat tcatggcagc aaaattatta ag          52

<210> SEQ ID NO 56
<211> LENGTH: 40
<212> TYPE: DNA
<213> ORGANISM: Artificial Sequence
<220> FEATURE:
<223> OTHER INFORMATION: Reverse primer for folD amplification

<400> SEQUENCE: 56
tcatccgcca aaacagccaa gctataataa gccgttttgc          40

<210> SEQ ID NO 57
<211> LENGTH: 54
<212> TYPE: DNA
<213> ORGANISM: Artificial Sequence
<220> FEATURE:
<223> OTHER INFORMATION: Forward primer for pckA amplification

<400> SEQUENCE: 57
ttgttgagac acttacacga aggaggaatt catgacagat cttaatcaat taac          54

<210> SEQ ID NO 58
<211> LENGTH: 20
<212> TYPE: DNA
<213> ORGANISM: Artificial Sequence
<220> FEATURE:
<223> OTHER INFORMATION: Reverse primer for pckA amplification

<400> SEQUENCE: 58
ttatgcttta ggaccggcag          20

<210> SEQ ID NO 59
<211> LENGTH: 51
<212> TYPE: DNA
<213> ORGANISM: Artificial Sequence
<220> FEATURE:
<223> OTHER INFORMATION: Forward primer for sga amplification

<400> SEQUENCE: 59
ttgttgagac acttacacga aggaggaatt catggactat atgtatggac c          51

<210> SEQ ID NO 60
<211> LENGTH: 42

<212> TYPE: DNA
<213> ORGANISM: Artificial Sequence
<220> FEATURE:
<223> OTHER INFORMATION: Reverse primer for sga amplification

<400> SEQUENCE: 60
tcatccgcca aaacagccaa gttagattct agagggaatg ag         42

<210> SEQ ID NO 61
<211> LENGTH: 51
<212> TYPE: DNA
<213> ORGANISM: Artificial Sequence
<220> FEATURE:
<223> OTHER INFORMATION: Forward primer for pfl amplification

<400> SEQUENCE: 61
agaacgtcgt cgaggcgtaa aggaggaatt catgacgaat cgtatctctc g    51

<210> SEQ ID NO 62
<211> LENGTH: 20
<212> TYPE: DNA
<213> ORGANISM: Artificial Sequence
<220> FEATURE:
<223> OTHER INFORMATION: Reverse primer for pfl amplification

<400> SEQUENCE: 62
ttacagctga tgcgctgtcc                                  20

<210> SEQ ID NO 63
<211> LENGTH: 4500
<212> TYPE: DNA
<213> ORGANISM: Escherichia coli

<400> SEQUENCE: 63
atggcacaac agactccttt gtacgaacaa cacacgcttt gcggcgctcg catggtggat    60
ttccacggct ggatgatgcc gctgcattac ggttcgcaaa tcgacgaaca tcatgcggta   120
cgtaccgatg ccggaatgtt tgatgtgtca catatgacca tcgtcgatct tcgcggcagc   180
cgcacccggg agtttctgcg ttatctgctg cgaacgatg tggcgaagct caccaaaagc   240
ggcaaagccc tttactcggg gatgtttaat gcctctggcg gtgtgataga tgacctcatc   300
gtctactact ttactgaaga tttcttccgc ctcgttgtta actccgccac ccgcgaaaaa   360
gacctctcct ggattaccca acacgctgaa cctttcggca tcgaaattac cgttcgtgat   420
gacctttcca tgattgccgt gcaagggccg aatgcgcagg caaaagctgc cacactgttt   480
aatgacgccc agcgtcaggc ggtggaaggg atgaaaccgt tctttggcgt gcaggcgggc   540 gatctgtttta ttgccaccac tggttatacc ggtgaagcgg gctatgaaat tgcgctgccc   600
aatgaaaaag cggccgattt ctggcgtgcg ctggtggaag cgggtgttaa gccatgtggc   660
ttgggcgcgc gtgacacgct gcgtctggaa gcgggcatga atctttatgg tcaggagatg   720
gacgaaacca tctctccttt agccgccaac atggcctgga ccatcgcctg gaaccggca   780 gatcgtgact ttatcggtcg tgaagccctg gaagtgcagc gtgagcatgg tacagaaaaa   840
ctggttggtc tggtgatgac cgaaaaaggc gtgctgcgta atgaactgcc ggtacgcttt   900
accgatgcga agggcaacca gcatgaaggc attatcacca cgcggtactt ctcccccgacg   960 ctgggttaca gcattgcgct ggcgcgcgtg ccggaaggta ttggcgaaac ggcgattgtg  1020
caaattcgca accgtgaaat gccggttaaa gtgacaaaac tgttttttgt gcgtaacggc  1080
aaagccgtcg cgtgatttac ttttttggag attgattgat gagcaacgta ccagcagaac  1140

-continued

```
tgaaatacag caaagaacac gaatggctgc gtaaagaagc cgacggcact tacaccgttg    1200
gtattaccga acatgctcag gagctgttag gcgatatggt gtttgttgac ctgccggaag    1260
tgggcgcaac ggttagcgcg ggcgatgact gcgcggttgc cgaatcggta aaagcggcgt    1320
cagacattta tgcgccagta agcggtgaaa tcgtggcgt aaacgacgca ctgagcgatt     1380
ccccggaact ggtgaacagc gaaccgtatg caggcggctg gatctttaaa atcaaagcca    1440
gcgatgaaag cgaactggaa tcactgctgg atgcgaccgc atacgaagca ttgttagaag    1500
acgagtaacg gctttattcc tcttctgcgg gagaggatca gggtgaggaa aatttatgcc    1560
tcaccctcac tctcttcgta aggagagagg ttcacaattc actgcacgtt tcaggaacca    1620
tcgctcatga cacagacgtt aagccagctt gaaaacagcg gcgcttttat tgaacgccat    1680
atcggaccgg acgccgcgca acagcaagaa atgctgaatg ccgttggtgc acaatcgtta    1740
aacgcgctga ccggccagat tgtgccgaaa gatattcaac ttgcgacacc accgcaggtt    1800
ggcgcaccgg cgaccgaata cgccgcactg gcagaactca aggctattgc cagtcgcaat    1860
aaacgcttca cgtcttacat cggcatgggt tacaccgccg tgcagctacc gccggttatc    1920
ctgcgtaaca tgctggaaaa tccgggctgg tataccgcgt acactccgta tcaacctgaa    1980
gtctcccagg gccgccttga agcactgctc aacttccagc aggtaacgct ggatttgact    2040
ggactggata tggcctctgc ttctcttctg gacgaggcca ccgctgccgc cgaagcaatg    2100
gcgatggcga aacgcgtcag caaactgaaa atgccaacc gcttcttcgt ggcttccgat     2160
gtgcatccgc aaacgctgga tgtggtccgt actcgtgccg aaacctttgg ttttgaagtg    2220
attgtcgatg acgcgcaaaa agtgctcgac catcaggacg tcttcggcgt gctgttacag    2280
caggtaggca ctaccggtga aattcacgac tacactgcgc ttattagcga actgaaatca    2340
cgcaaaattg tggtcagcgt tgccgccgat attatgcgc tggtgctgtt aactgcgccg      2400
ggtaaacagg gcgcggatat tgttttggt tcggcgcaac gcttcggcgt gccgatgggc      2460
tacggtggcc cacacgcggc attctttgcg gcgaaagatg aatacaaacg ctcaatgccg    2520
ggccgtatta tcggtgtatc gaaagatgca gctggcaata ccgcgctgcg catggcgatg    2580
cagactcgcg agcaacatat ccgccgtgag aaagcgaact ccaacatttg tacttcccag    2640
gtactgctgg caaacatcgc cagcctgtat gccgtttatc acggcccggt tggcctgaaa    2700
cgtatcgcta accgcattca ccgtctgacc gatatcctgg cggcgggcct gcaacaaaaa    2760
ggtctgaaac tgcgccatgc gcactatttc gacaccttgt gtgtggaagt ggccgacaaa    2820
gcgggcgtac tgacgcgtgc cgaagcggct gaaatcaacc tgcgtagcga tattctgaac    2880
gcggttggga tcacccttga tgaaacaacc acgcgtgaaa acgtaatgca gcttttcaac    2940
gtgctgctgg cgataaccca cggcctggac atcgacacgc tggacaaaga cgtggctcac    3000
gacagccgct ctatccagcc tgcgatgctg cgcgacgacg aaatcctcac ccatccggtg    3060
tttaatcgct accacagcga aaccgaaatg atgcgctata tgcactcgct ggagcgtaaa    3120
gatctggcgc tgaatcaggc gatgatcccg ctgggttcct gcaccatgaa actgaacgcc    3180
gccgccgaga tgatcccaat cacctggccg gaatttgccg aactgcaccc gttctgcccg    3240
ccggagcagc ccgaaggtta tcagcagatg attgcgcagc tggctgactg gctggtgaaa    3300
ctgaccggtt acgacgccgt ttgtatgcag ccgaactctg gcgcacaggg cgaatacgcg    3360
ggcctgctgg cgattcgtca ttatcatgaa agccgcaacg aagggcatcg cgatatctgc    3420
ctgatcccgg cttctgcgca cggaactaac cccgcttctg cacatatggc aggaatgcag    3480
gtggtggttg tggcgtgtga taaaaacggc aacatcgatc tgactgatct gcgcgcgaaa    3540
```

```
gcggaacagg cgggcgataa cctctcctgt atcatggtga cttatccttc tacccacggc    3600
gtgtatgaag aaacgatccg tgaagtgtgt gaagtcgtgc atcagttcgg cggtcaggtt    3660
taccttgatg gcgcgaacat gaacgcccag gttggcatca cctcgccggg ctttattggt    3720
gcggacgttt cacaccttaa cctacataaa actttctgca ttccgcacgg cggtggtggt    3780
ccgggtatgg gaccgatcgg cgtgaaagcg catttggcac cgtttgtacc gggtcatagc    3840
gtggtgcaaa tcgaaggcat gttaacccgt cagggcgcgg tttctgcggc accgttcggt    3900
agcgcctcta tcctgccaat cagctggatg tacatccgca tgatgggcgc agaagggctg    3960
aaaaaagcaa gccaggtggc aatcctcaac gccaactata ttgccagccg cctgcaggat    4020
gccttcccgg tgctgtatac cggtcgcgac ggtcgcgtgg cgcacgaatg tattctcgat    4080
attcgcccgc tgaaagaaga aaccggcatc agcgagctgg atattgccaa gcgcctgatc    4140
gactacggtt ccacgcgcc gacgatgtcg ttccggtgg cgggtacgct gatggttgaa    4200
ccgactgaat ctgaaagcaa agtggaactg atcgcttta cgacgcgat gctggctatc    4260 cgcgcagaaa ttgaccaggt gaaagccggt gtctggccgc tggaagataa cccgctggtg    4320
aacgcgccgc acattcagag cgaactggtc gccgagtggg cgcatccgta cagccgtgaa    4380
gttgcggtat tcccggcagg tgtggcagac aaatactggc cgacagtgaa acgtctggat    4440
gatgtttacg cgaccgtaa cctgttctgc tcctgcgtac cgattagcga ataccagtaa    4500

<210> SEQ ID NO 64
<211> LENGTH: 52
<212> TYPE: DNA
<213> ORGANISM: Artificial Sequence
<220> FEATURE:
<223> OTHER INFORMATION: Forward Primer for GCV amplification

<400> SEQUENCE: 64
ttgttgagac acttacacga aggaggaatt catggcacaa cagactcctt tg              52

<210> SEQ ID NO 65
<211> LENGTH: 42
<212> TYPE: DNA
<213> ORGANISM: Artificial Sequence
<220> FEATURE:
<223> OTHER INFORMATION: Reverse Primer for GCV amplification

<400> SEQUENCE: 65
tcatccgcca aaacagccaa gttactggta ttcgctaatc gg                          42

<210> SEQ ID NO 66
<211> LENGTH: 573
<212> TYPE: DNA
<213> ORGANISM: Escherichia coli

<400> SEQUENCE: 66
ttgacactgt catcgcaaca ttatctggtg atcactgcgt tgggtgccga tcgccctgga      60
attgtgaaca ccatcacccg tcatgtcagt agttgcggct gtaatattga agacagtcgc     120
ctggcgatgc tggagaaga gttcacgttt attatgctgc tttccggttc atggaatgcc     180
attactctga ttgaatcaac gttaccgttg aaaggtgccg aactggatct tttaatcgtg     240
atgaagcgca cgacggcgcg tccgcgtccg ccaatgccag catctgtctg ggttcaggtc     300
gatgtggcag actccccgca tttaattgaa cgcttcacag cacttttcga cgcgcatcat     360
atgaacattg cggagctggt gtcgcgcacg caacctgctg aaaaatgaacg ggctgcgcag     420
```

| ttgcatattc agataaccgc ccacagcccc gcatctgcgg acgcagcaaa tattgagcaa | 480 |
| gcgttcaaag ccctatgtac agaactcaat gcacaaggca gtattaacgt cgtcaattat | 540 |
| tcccaacatg atgaacagga tggagttaag taa | 573 |

<210> SEQ ID NO 67
<211> LENGTH: 1543
<212> TYPE: DNA
<213> ORGANISM: Escherichia coli

<400> SEQUENCE: 67

| aaaatttctc ctctgttgtt tatttgatac ccatcacact ttcatctccc ggttttttcg | 60 |
| ccgggagatt ttcctcattt gaaataaact aatttcacct ccgttttcgc attatatttt | 120 |
| ctaatgccat tattttttga tttagtgttt tttgacattt ttttagctct taatattgtc | 180 |
| ttattcaaat tgactttctc atcacatcat ctttgtatag aaactggtgt attttttggt | 240 |
| tttttattct gtcgcgattt ttgcattttt taaccataag ctaatgtgat gatcaatttt | 300 |
| accttatggt taacagtctg tttcggtggt aagttcaggc aaaagagaac gattgcgttg | 360 |
| gggaccggga gtggctccga tgctgggttt cgtggtgata atttcaccat gaaaaagttg | 420 |
| tcagccccgc ttattcaatg aggacaagat ggcacaacag actcctttgt acgaacaaca | 480 |
| cacgctttgc ggcgctcgca tggtggattt ccacggctgg atgatgccgc tgcattacgg | 540 |
| ttcgcaaatc gacgaacatc atgcggtacg taccgatgcc ggaatgtttg atgtgtcaca | 600 |
| tatgaccatc gtcgatcttc gcggcagccg cacccgggag tttctgcgtt atctgctggc | 660 |
| gaacgatgtg gcgaagctca ccaaaagcgg caaagccctt tactcgggga tgttgaatgc | 720 |
| ctctggcggt gtgatagatg acctcatcgt ctactacttt actgaagatt tcttccgcct | 780 |
| cgttgttaac tccgccaccc gcgaaaaaga cctctcctgg attacccaac acgctgaacc | 840 |
| tttcggcatc gaaattaccg ttcgtgatga ccttcccatg attgccgtgc aagggccgaa | 900 |
| tgcgcaggca aaagctgcca cactgtttaa tgacgcccag cgtcaggcgg tggagggat | 960 |
| gaaccgttc tttggcgtgc aggcgggcga tctgtttatt gccaccactg gttataccgg | 1020 |
| tgaagcgggc tatgaaattg cgctgcccaa tgaaaaagcg gccgatttct ggcgtgcgct | 1080 |
| ggtggaagcg ggtgttaagc catgtggctt gggcgcgcgt gacacgctgc gtctggaagc | 1140 |
| gggcatgaat ctttatggtc aggagatgga cgaaaccatc tctccttttag ccgccaacat | 1200 |
| gggctggacc atcgcctggg aaccggcaga tcgtgacttt atcggtcgtg aagccctgga | 1260 |
| agtgcagcgt gagcatggta cagaaaaaact ggttggtctg gtgatgaccg aaaaaggcgt | 1320 |
| gctgcgtaat gaactgccgg tacgctttac cgatgcgcag ggcaaccagc atgaaggcat | 1380 |
| tatcaccagc ggtactttct ccccgacgct gggttacagc attgcgctgg cgcgcgtgcc | 1440 |
| ggaaggtatt ggcgaaacgg cgattgtgca aattcgcaac cgtgaaatgc cggttaaagt | 1500 |
| gacaaaacct gttttgtgc gtaacggcaa agccgtcgcg tga | 1543 |

<210> SEQ ID NO 68
<211> LENGTH: 1503
<212> TYPE: DNA
<213> ORGANISM: Artificial Sequence
<220> FEATURE:
<223> OTHER INFORMATION: Promoter substitution from SEQ ID NO. 67

<400> SEQUENCE: 68

| cccatcagat ccactagtgg cctatgcggc cgcggatctg ccggtctccc tatagtgaga | 60 |
| tctggcacga caggtttccc gactggaaag cgggcagtga gcgcaacgca attaatgtga | 120 |

```
gttagcgcga attgatctgg tttgacagct tatcatcgac tgcacggtgc accaatgctt    180
ctggcgtcag gcagccatcg gaagctgtgg tatggctgtg caggtcgtaa atcactgcat    240
aattcgtgtc gctcaaggcg cactcccgtt ctggataatg ttttttgcgc cgacatcata    300
acggttctgg caaatattct gaaatgagct gttgacaatt aatcatccgg ctcgtataat    360
gtgtggaatt gtgagcggat aacaatttca cacaggaaac agaccatgat ggcacaacag    420
actcctttgt acgaacaaca cacgcttgcg gcgctcgca tggtggattt ccacggctgg    480
atgatgccgc tgcattacgg ttcgcaaatc gacgaacatc atgcggtacg taccgatgcc    540
ggaatgtttg atgtgtcaca tatgaccatc gtcgatcttc gcggcagccg cacccgggag    600
tttctgcgtt atctgctggc gaacgatgtg gcgaagctca ccaaaagcgg caaagccctt    660
tactcgggga tgttgaatgc ctctggcggt gtgatagatg acctcatcgt ctactacttt    720
actgaagatt tcttccgcct cgttgttaac tccgccaccc gcgaaaaaga cctctcctgg    780
attacccaac acgctgaacc tttcggcatc gaaattaccg ttcgtgatga cctttccatg    840
attgccgtgc aagggccgaa tgcgcaggca aaagctgcca cactgtttaa tgacgcccag    900
cgtcaggcgg tggaagggat gaaaccgttc tttggcgtgc aggcgggcga tctgtttatt    960
gccaccactg gttataccgg tgaagcgggc tatgaaattg cgctgcccaa tgaaaaagcg   1020
gccgatttct ggcgtgcgct ggtggaagcg ggtgttaagc catgtggctt gggcgcgcgt   1080
gacacgctgc gtctggaagc gggcatgaat ctttatggtc aggagatgga cgaaaccatc   1140
tctccttta g ccgccaacat gggctggacc atcgcctggg aaccggcaga tcgtgacttt   1200
atcggtcgtg aagccctgga agtgcagcgt gagcatggta cagaaaaact ggttggtctg   1260
gtgatgaccg aaaaaggcgt gctgcgtaat gaactgccgg tacgctttac cgatgcgcag   1320
ggcaaccagc atgaaggcat tatcaccagc ggtactttct ccccgacgct gggttacagc   1380
attgcgctgg cgcgcgtgcc ggaaggtatt ggcgaaacgg cgattgtgca aattcgcaac   1440
cgtgaaatgc cggttaaagt gacaaaacct gttttttgtgc gtaacggcaa agccgtcgcg   1500
tga                                                                 1503

<210> SEQ ID NO 69
<211> LENGTH: 1365
<212> TYPE: DNA
<213> ORGANISM: Escherichia coli

<400> SEQUENCE: 69
atgattagtc tattcgacat gtttaaggtg gggattggtc cctcatcttc ccataccgta     60
gggcctatga aggcaggtaa acagttcgtc gatgatctgg tcgaaaaagg cttactggat    120
agcgttactc gcgttgccgt ggacgtttat ggttcactgt cgctgacggg taaaggccac    180
cacaccgata tcgccattat tatgggtctt gcaggtaacg aacctgccac cgtggatatc    240
gacagtattc ccggttttat tcgcgacgta aagagcgcg aacgtctgct gctggcacag    300
ggacggcatg aagtggattt cccgcgcgac aacgggatgc gttttcataa cggcaacctg    360
ccgctgcatg aaaacggtat gcaaatccac gcctataacg gcgatgaagt cgtctacagc    420
aaaacttatt attccatcgg cggcggtttt atcgtcgatg aagaacactt tggtcaggat    480
gctgccaacg aagtaagcgt gccgtatccg ttcaaatctg ccaccgaact gctcgcgtac    540
tgtaatgaaa ccggctattc gctgtctggt ctcgctatgc agaacgaact ggcgctgcac    600
agcaagaaag agatcgacga gtatttcgcg catgtctggc aaaccatgca ggcatgtatc    660
```

```
gatcgcggga tgaacaccga aggtgtactg ccaggcccgc tgcgcgtgcc acgtcgtgcg      720
tctgccctgc gccggatgct ggtttccagc gataaactgt ctaacgatcc gatgaatgtc      780
attgactggg taaacatgtt tgcgctggca gttaacgaag aaaacgccgc cggtggtcgt      840
gtggtaactg cgccaaccaa cggtgcctgc ggtatcgttc cggcagtgct ggcttactat      900
gaccacttta ttgaatcggt cagcccggac atctataccc gttactttat ggcagcgggc      960
gcgattggtg cattgtataa aatgaacgcc tctatttccg gtgcggaagt tggttgccag     1020
ggcgaagtgg gtgttgcctg ttcaatggct gctgcgggtc ttgcagaact gctgggcggt     1080
agcccggaac aggtttgcgt ggcggcggaa attggcatgg aacacaacct tggtttaacc     1140
tgcgacccgg ttgcagggca ggttcaggtg ccgtgcattg agcgtaatgc cattgcctct     1200
gtgaaggcga ttaacgccgc gcggatggct ctgcgccgca ccagtgcacc gcgcgtctcg     1260
ctggataagg tcatcgaaac gatgtacgaa accggtaagg acatgaacgc caaataccgc     1320
gaaacctcac gcggtggtct ggcaatcaaa gtccagtgtg actaa                     1365
```

RECOMBINANT MICROORGANISM HAVING HETEROLOGOUS GENES INTRODUCED THERETO AND METHOD FOR PRODUCING USEFUL MATERIAL FROM FORMIC ACID AND CARBON DIOXIDE USING SAME MICROORGANISM

CROSS-REFERENCE TO RELATED APPLICATIONS

This application is a U.S. national phase under the provisions of 35 U.S.C. § 371 of International Patent Application No. PCT/KR17/13171 filed Nov. 20, 2017, which in turn claims priority of Korean Patent Application No. 10-2016-0180223 filed Dec. 27, 2016 and Korean Patent Application No. 10-2017-0151642 filed Nov. 14, 2017. The disclosures of such international patent application and Korean priority patent applications are hereby incorporated herein by reference in their respective entireties, for all purposes.

TECHNICAL FIELD

The present invention relates to a recombinant microorganism introduced with heterologous genes and a method for producing a useful substance from formic acid and carbon dioxide using the microorganism. More specifically, the present invention relates to a recombinant microorganism, which is capable of efficiently synthesizing one molecule of pyruvate by introducing heterologous genes into the microorganism having a cyclic metabolic pathway and simultaneously assimilating two molecules of formic acid and one molecule of carbon dioxide, and a method for producing a useful substance from formic acid and carbon dioxide using the microorganism.

BACKGROUND ART

In order to develop carbon fixation technologies to mitigate climate change, researches are actively underway to convert a compound consisting of one carbon, such as carbon dioxide into an organic substance having a higher carbon number. Researches on the conversion of compounds consisting of one carbon (a C1 compound) can be roughly classified into chemical methods and biological methods. Among them, chemical methods are carried out using electrochemical reactions based on metal- and non-metal-catalysts. Through such reactions, carbon dioxide is converted into a non-gaseous carbon compound such as methanol and formic acid, and examples of related research include conversion using a carbon nanotube catalyst (Kumar et al., Nat. Comm. 2819, 2013), conversion using an iron catalyst (Christopher et al., Angew. Chem. Int. Ed. 49:50, 9777-9780, 2010) and conversion using an alloy catalyst (Studt et al., Nat. Chem., 6, 320-324, 2014) and the like. Conversion using these chemical methods has an advantage of a relatively highspeed, but has a limitation in that the products obtained through the C1 compound conversion process are single-carbon substances such as formic acid and methanol, rather than useful compounds containing multiple carbon atoms.

Regarding biological conversion methods, researches are underway with the goal of converting a gaseous C1 compound into a non-gaseous compound and converting a C1 compound into a useful compound consisting of several carbon atoms. In the former case, researches have been conducted on the use of metabolic pathways present in nature and the improvement thereof (PCT/US2008/083056), designs of new metabolic pathways (Schwander et al., Science, 354: 6314, 900-904, 2016) and the like. Examples of the latter case include the production of useful compounds using methanol-assimilating microorganisms (US 2003/0124687 A1), the production of compounds having three carbon atoms from formic acid (US 2013/0196359 A1) and the like. However, these researches have limitations in that it is difficult to identify the effects thereof under internal conditions of organisms due to the low efficiency thereof and in that whether they can function in a manner compatible with native metabolic pathways in living organisms has not been verified.

Therefore, research to overcome the limitations of the biological C1 compound conversion process described above and to thereby develop an efficient C1 compound conversion process is arising in the industry. In particular, among the C1 compounds, formic acid has benefits in that it is relatively less toxic to organisms than other C1 compounds and is advantageous for assimilation (anabolic) reaction compared to C1 compounds in terms of reaction kinetics, and can be synthesized easily and rapidly from carbon dioxide through chemical methods. However, the genetic information of the genus *Methylobacterium*, which is a representative formic acid-assimilating bacterium, was reported only in 2009, that is to say, basic research for application thereof was only conducted relatively recently, and research on the conversion of formic acid is still at an early stage. At present, research relating to assimilation (anabolism) of formic acid is still at the level of the presentation and designing of metabolic pathways using an enzyme information database (US 2015/0218528 A1; Arren Bar-Even., Biochemistry, 55:28, 3851-3863), and no case demonstrating the same has been reported yet.

Accordingly, the present inventors have designed a novel metabolic pathway for converting a C1 compound, formic acid, into a useful compound having a plurality of carbon atoms, and have attempted to demonstrate the metabolic pathway under in vivo conditions of organisms. As a result, the present inventors have developed a cyclic metabolic pathway which involves effectively assimilating formic acid and carbon dioxide at the same time, thereby producing a single molecule of acetyl-CoA as a product of the cyclic metabolic pathway, when introducing novel genes derived from the genus *Methylobacterium*, the genus *Rhodobacter*, the genus *Chloroflexus*, the genus *Acetobacterium*, the genus *Roseobacter* and the genus *Mannheimia*, and have identified that acetyl-CoA obtained as the product of the cyclic metabolic pathway binds to a single molecule of formic acid to produce pyruvate, as a C3 compound, when further introducing a reverse reaction of pyruvate formate lyase. Further, the present inventors have developed a metabolic pathway that is capable of producing glycine, serine and pyruvate by effectively assimilating formic acid and carbon dioxide using novel genes derived from the genus *Methylobacterium* microorganism and genes derived from the genus *Escherichia* microorganism and have identified that glycine, serine and pyruvate were produced from formic acid and carbon dioxide using the corresponding metabolic pathway. Based on these findings, the present invention has been completed.

DISCLOSURE

Technical Problem

Therefore, it is one object of the present invention to provide a recombinant microorganism for producing a useful substance including a C3 compound from formic acid and carbon dioxide.

It is another object of the present invention to provide a method for producing a useful substance including a C3 compound from formic acid and carbon dioxide using the recombinant microorganism.

Technical Solution

In accordance with one aspect of the present invention, provided is a recombinant microorganism obtained by introducing a gene encoding an enzyme involved in a formic acid assimilation pathway or a recombinant vector containing the gene into a host microorganism having a central carbon assimilation pathway.

In accordance with another aspect of the present invention, provided is a method for producing a useful compound having a C3 compound as an intermediate product including: (a) culturing the recombinant microorganism with formic acid and carbon dioxide as a carbon source to produce a useful substance having a C3 compound as an intermediate product; and (b) recovering the resulting useful substance.

DESCRIPTION OF DRAWINGS

The patent or application file contains at least one drawing executed in color. Copies of this patent or patent application publication with color drawing(s) will be provided by the Office upon request and payment of the necessary fee.

Reference will now be made in detail to the preferred embodiments of the present invention, examples of which are illustrated in the accompanying drawings. Wherever possible, the same reference numbers will be used throughout the drawings to refer to the same or like parts.

BEST MODE

Unless defined otherwise, all technical and scientific terms used herein have the same meanings as appreciated by those skilled in the field to which the present invention pertains. In general, the nomenclature used herein is well-known in the art and is ordinarily used.

The present inventors first experimentally identified a novel cyclic metabolic pathway capable of synthesizing compounds composed of three or more carbon atoms from formic acid and carbon dioxide. That is, the present inventors designed the cyclic metabolic pathways shown in FIGS. 6A-6E, and constructed a plasmid containing a synthetic operon for expression in the microorganism such that the metabolic pathway could be implemented in a subject (host) microorganism. As a result of transformation of the same into the subject (host) microorganism, the present inventors have identified that formic acid and carbon dioxide could be effectively assimilated inside the microorganism and converted into a C3 compound.

Figure 2A:
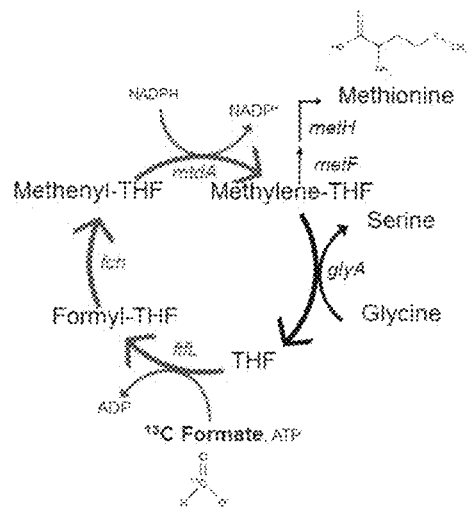
FIG. 2A shows the formic acid assimilation pathway developed in the present invention and FIG. 2B shows results of comparison in formic acid assimilation efficiency between a wild-type control group (DH5α WT) and an experimental recombinant microorganism group (DH5α THF), wherein, in FIG. 2B, "M+0" represents the original mass number of the corresponding amino acid, and "M+1 above" represents the mass number when the corresponding amino acid contains an isotope, and since there is a predetermined ratio of isotopes in a natural system, a predetermined ratio of M+1 above amino acid is present in a wild-type control group as well.
Figure 2B:
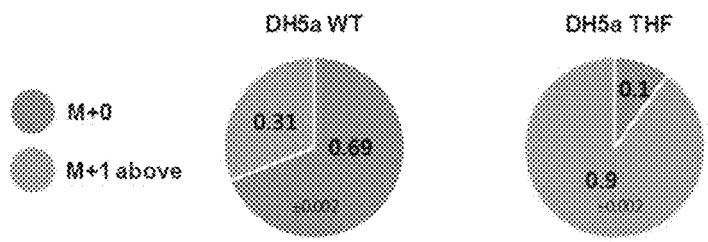

Specifically, the present inventors constructed a novel cyclic metabolic pathway for assimilating formic acid and have identified that formic acid was assimilated through the metabolic pathway when the metabolic pathway was introduced into the host microorganism. In addition, the present inventors have found that the assimilation efficiency of formic acid was significantly increased when using some enzymes involved in the metabolic pathway introduced from exotic microorganisms (FIGS. 2A and 2B).

Therefore, in one aspect, the present invention is directed to a recombinant microorganism obtained by introducing a gene encoding an enzyme involved in a formic acid assimilation pathway or a recombinant vector containing the gene into a host microorganism having a central carbon assimilation pathway.

Figure 1:
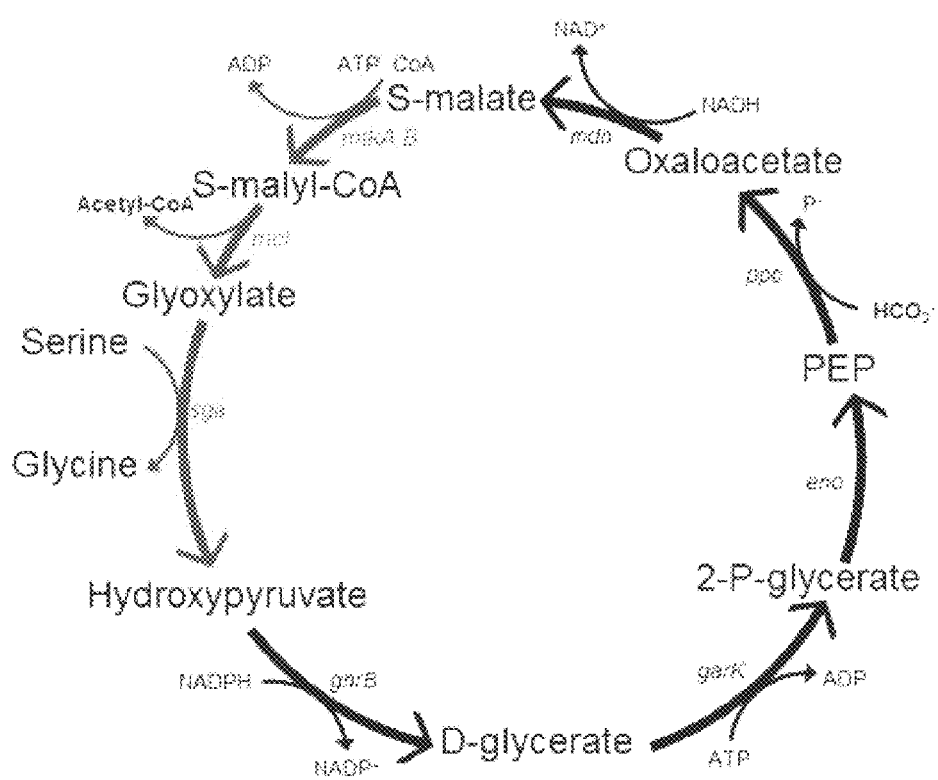
FIG. 1 shows genes, coenzymes and energy transfer substances involved in the central carbon assimilation pathway of E. coli.

In the present invention, the central carbon assimilation pathway is a cyclic pathway for fixing carbon dioxide in microorganisms. Genes, coenzymes and energy transfer substances involved in the central carbon assimilation pathway of *E. coli* are shown in FIG. 1.

In the present invention, the formic acid assimilation pathway can be combined with the central carbon assimilation pathway to synthesize a C3 or larger carbon compound. The host microorganism inherently possesses a central carbon assimilation pathway i); or has a central carbon assimilation pathway introduced externally ii).

The enzyme involved in the formic acid assimilation pathway in the present invention may be a gene of any one selected from the group consisting of formate-tetrahydrofolate ligase, methenyl tetrahydrofolate cyclohydrolase and methylene-tetrahydrofolate dehydrogenase, but is not limited thereto.

In the present invention, the genes may be derived from any one selected from the group consisting of *Methylobacterium, Roseobacter, Rhodobacter, Chloroflexus, Acetobacterium, Mannheimia, Escherichia* and *Arabidopsis*, but are not limited thereto.

In the present invention, the gene encoding formate-tetrahydrofolate ligase may be a nucleic acid molecule represented by SEQ ID NO: 7, the gene encoding methenyl tetrahydrofolate cyclohydrolase may be a nucleic acid molecule represented by SEQ ID NO: 8, and the gene encoding methylene-tetrahydrofolate dehydrogenase may be a nucleic acid represented by SEQ ID NO: 9 or SEQ ID NO: 19, but is not limited thereto.

Figure 4:
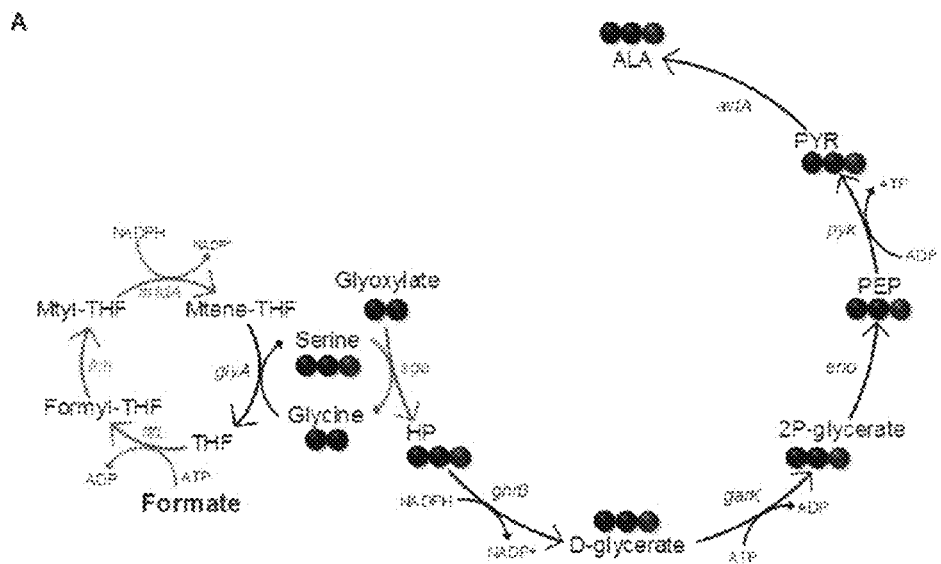
FIG. 4 shows the metabolic pathway in which the formic acid assimilation pathway developed in the present invention is connected to the central carbon assimilation pathway (A) and results of comparison in the extent of formic acid assimilation to the central carbon metabolism between the wild-type control (DH5α WT) and the experimental recombinant microorganisms (DH5α ST1 and DH5α ST2) (B)
Figure 4:
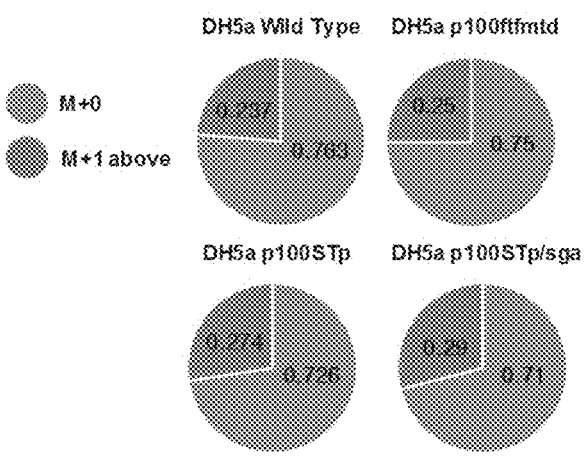
Figure 5:
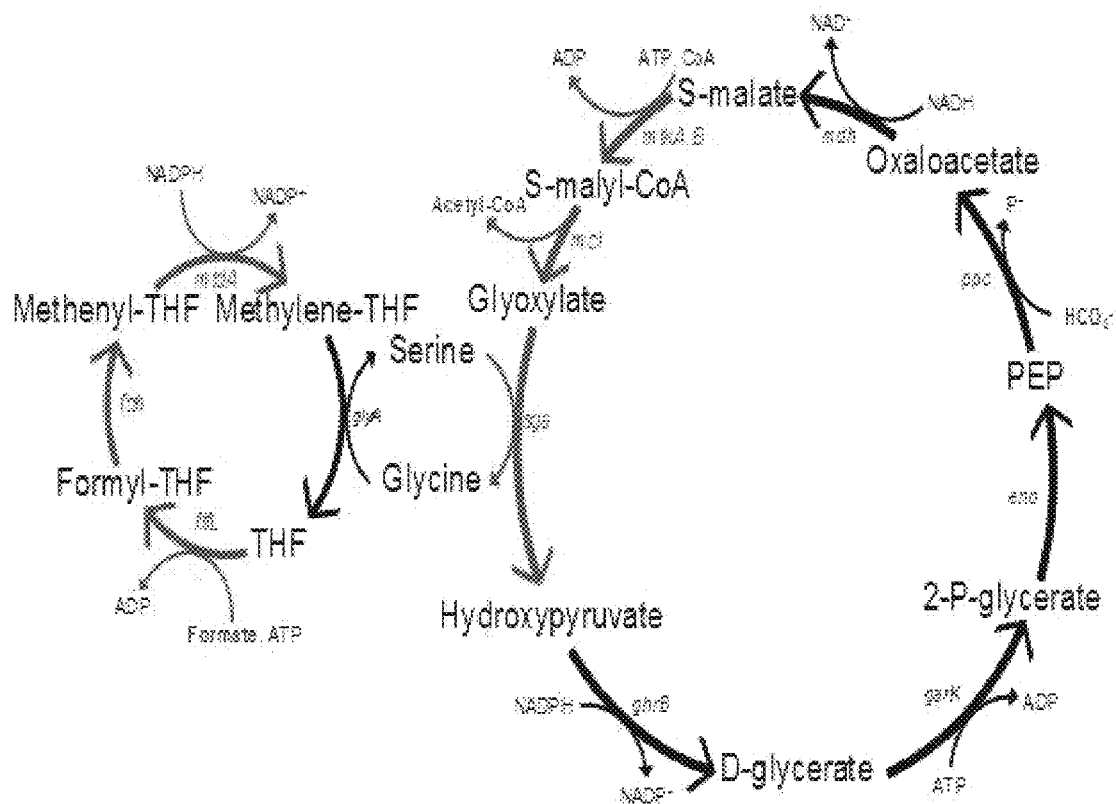
FIG. 5 shows a novel cyclic metabolic pathway developed in the present invention and genes, coenzymes, and energy-transferring substances involved in respective steps of the pathway.
Figure 6A:
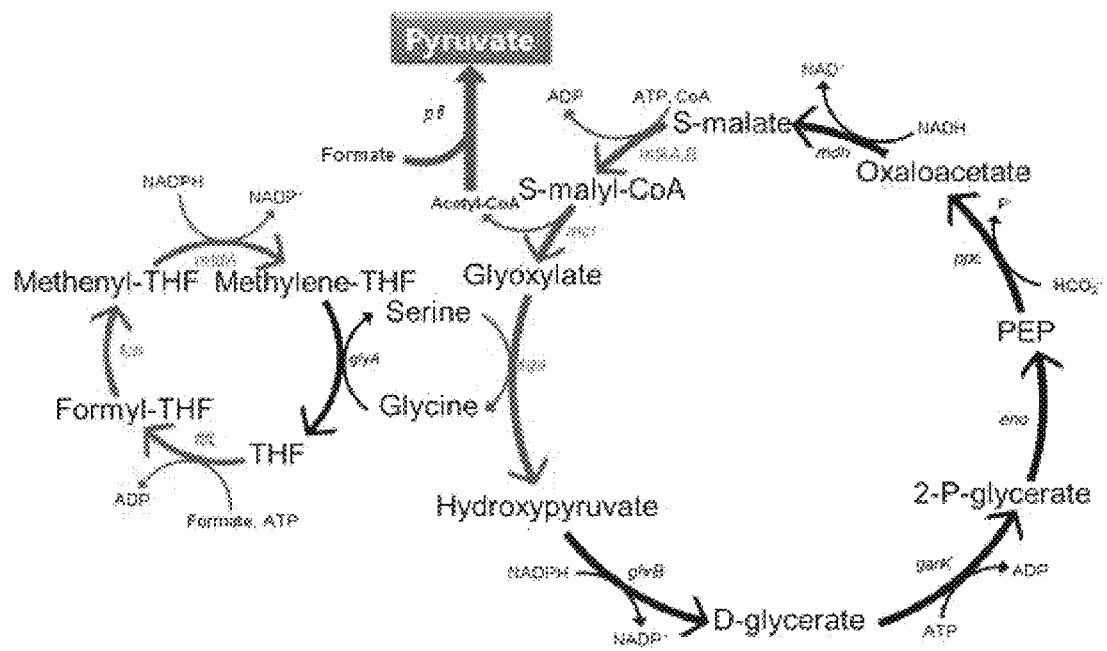
FIGS. 6A-6E show cyclic metabolic pathways of five embodiments for producing a C3 compound using formic acid and carbon dioxide developed in the present invention.
Figure 6B:
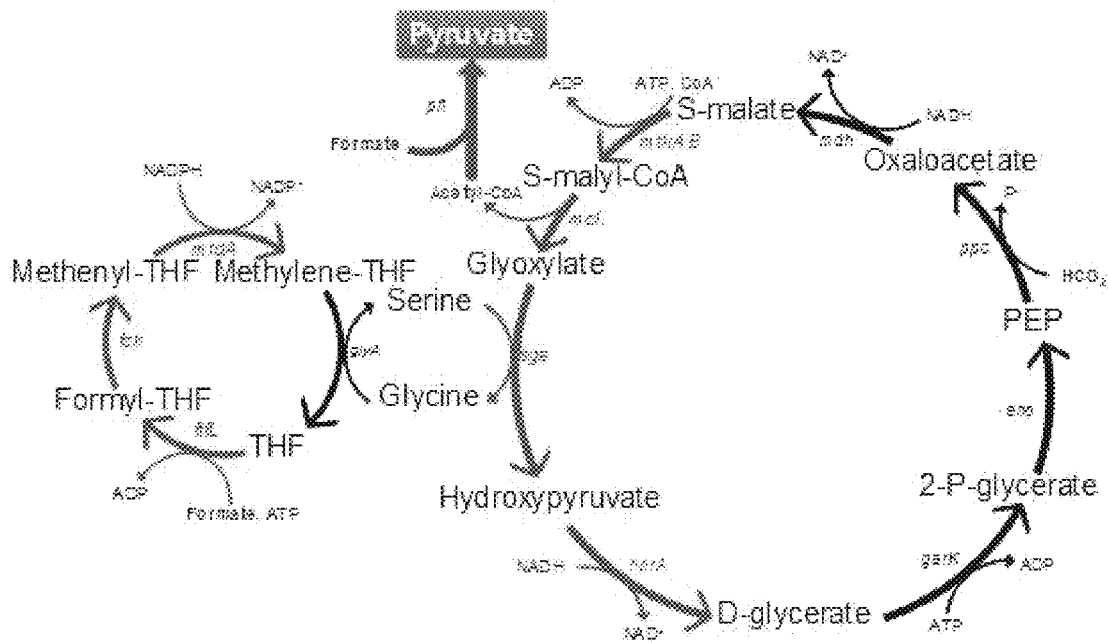
Figure 6C:
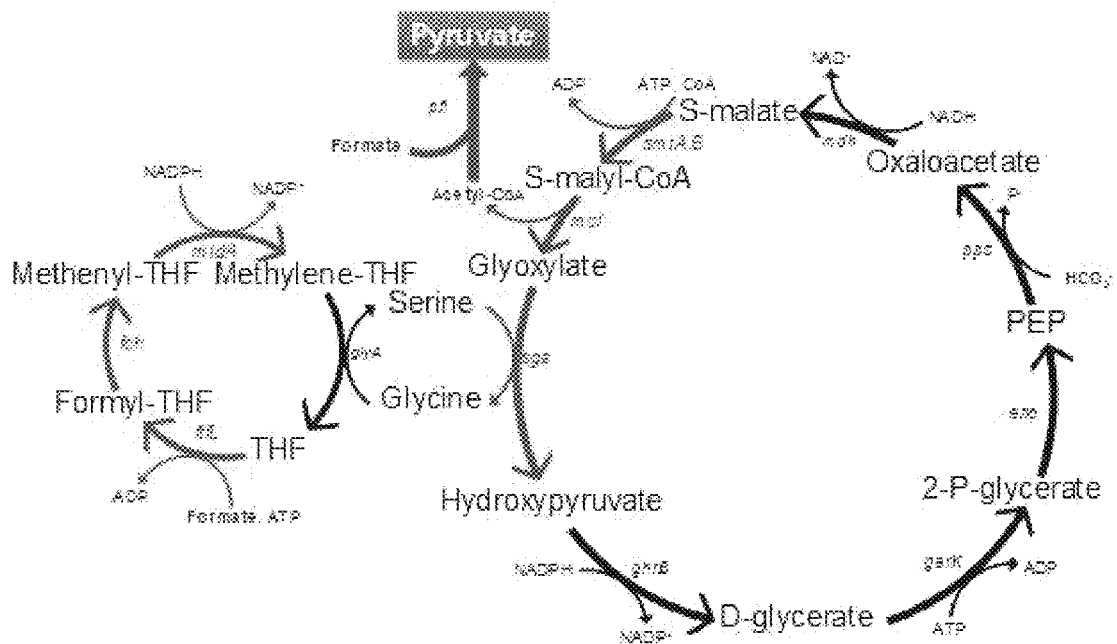
Figure 6D:
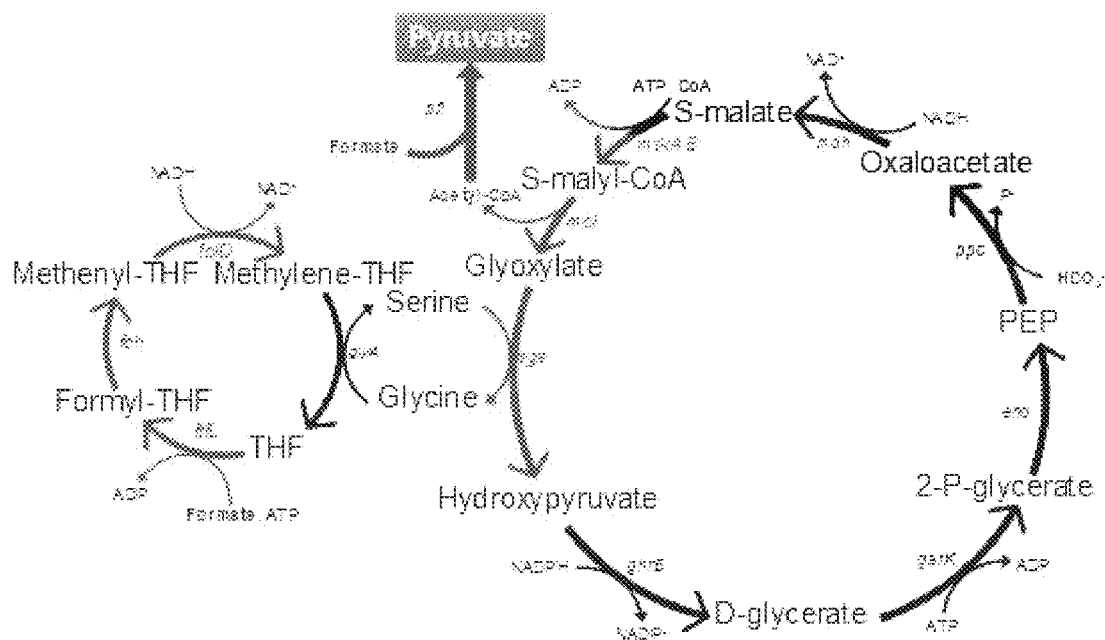
Figure 6E:
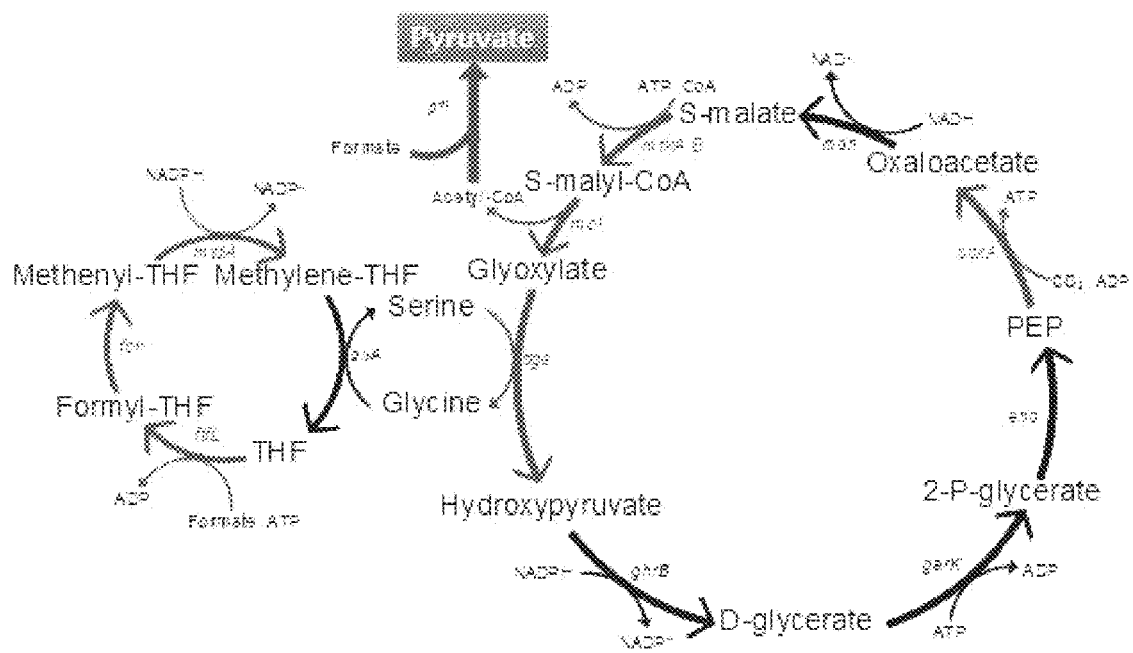

Meanwhile, the present inventors have verified whether or not formic acid assimilated by the formic acid assimilation pathway was assimilated into glycolysis, which is one of the central carbon metabolic processes of the host microorganism. Also the present inventors have found that assimilation efficiency was improved when substituting a part of genes involved in the main carbon metabolism with heterologous genes (FIGS. 4 and 5).

Accordingly, in another aspect, the present invention is directed to a recombinant microorganism that has an improvement in a central carbon assimilation pathway of a host microorganism.

In the present invention, at least one enzyme involved in the central carbon assimilation pathway and selected from the group consisting of serine-glyoxylate aminotransferase, malyl-CoA lyase, malate-CoA ligase, succinyl-CoA:(S)-malate CoA-transferase, phosphoenolpyruvate carboxykinase, and hydroxypyruvate reductase may be substituted, further introduced or amplified but is not limited thereto.

The substituted or further introduced enzymes may be enzymes derived from any one selected from the group consisting of *Methylobacterium, Roseobacter, Rhodobacter, Chloroflexus, Acetobacterium, Mannheimia, Escherichia* and *Arabidopsis*, but are not limited thereto.

In the present invention, the enzyme involved in the central carbon assimilation pathway may be substituted with one of the following:

i) a serine-glyoxylate transaminase encoded by a nucleic acid molecule selected from the group consisting of a nucleic acid molecule represented by SEQ ID NO: 6, a nucleic acid molecule represented by SEQ ID NO: 13, a nucleic acid molecule represented by SEQ ID NO: 16, and a nucleic acid molecule represented by SEQ ID NO: 21;

ii) malyl-CoA lyase encoded by a nucleic acid molecule selected from the group consisting of a nucleic acid molecule represented by SEQ ID NO: 5, a nucleic acid molecule represented by SEQ ID NO: 14, and a nucleic acid molecule represented by SEQ ID NO: 15;

iii) malate-CoA ligase encoded by a nucleic acid molecule selected from the group consisting of a nucleic acid molecule represented by SEQ ID NO: 3, a nucleic acid molecule represented by SEQ ID NO: 4, a nucleic acid molecule represented by SEQ ID NO: 11, and a nucleic acid molecule represented by SEQ ID NO: 12;

iv) succinyl-CoA:(S)-malate CoA-transferase encoded by a nucleic acid molecule represented by SEQ ID NO: 17 or a nucleic acid molecule represented by SEQ ID NO: 18;

v) phosphoenolpyruvate carboxykinase encoded by a nucleic acid molecule represented by SEQ ID NO: 20; and/or vi) hydroxypyruvate reductase encoded by a nucleic acid molecule of SEQ ID NO: 10, but is not limited thereto.

In one embodiment of the present invention, regarding the enzyme, the enzyme involved in the central carbon assimilation pathway of the *Escherichia* genus shown in FIG. 1 may be substituted with the enzyme shown in FIGS. 6(*a*) to 6(*e*).

Figure 7:
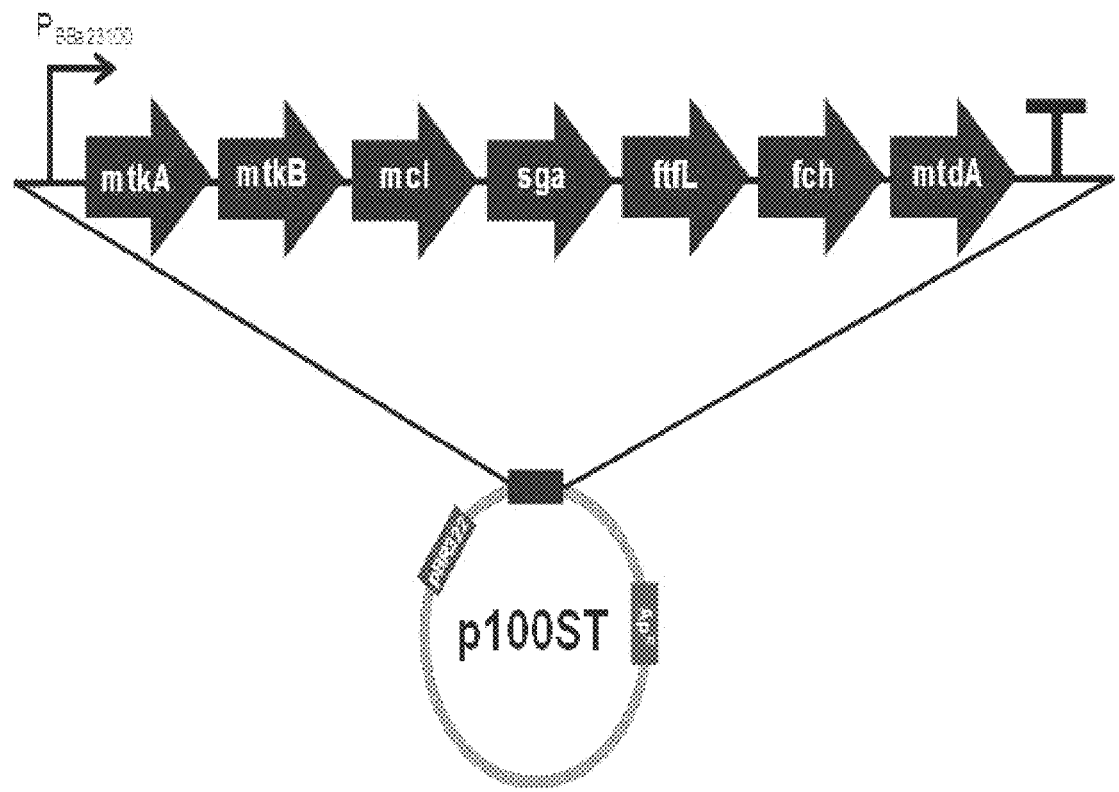
FIG. 7 shows a synthetic operon produced to introduce a novel cyclic metabolic pathway into microorganisms according to an embodiment of the present invention and a plasmid gene map including the same.

In the present invention, the genes may be transformed into a host microorganism in the form of a plasmid containing a synthetic operon (see FIG. 7), and the synthetic operon may include at least one selected from the group consisting of: formate-tetrahydrofolate ligase, methenyl tetrahydrofolate cyclohydrolase, methylene-tetrahydrofolate dehydrogenase, serine-glyoxylate transaminase, malyl-CoA lyase, malate-CoA ligase and hydroxypyruvate reductase of the genus *Methylobacterium* microorganism; malyl-CoA thioesterase and malyl-CoA lyase of the genus *Rhodobacter* microorganism; succinyl-CoA:(S)-malate CoA-transferase of the genus *Chloroflexus* microorganism; methenyl tetrahydrofolate cyclohydrolase of the genus *Acetobacterium* microorganism; malate-CoA ligase of the genus *Roseobacter* microorganism; and phosphoenolpyruvate carboxykinase of the genus *Mannheimia* microorganism, but is not limited thereto.

Meanwhile, when the formic acid assimilation pathway is combined with the central carbon assimilation pathway of the host microorganism, carbon dioxide and formic acid are converted into acetyl-CoA. The present inventors have found that formic acid could be further assimilated to produce a C3 compound by further introducing a metabolic pathway based on pyruvate formate lyase (FIGS. 6A-6E).

Thus, in another aspect, the present invention is directed to a recombinant microorganism having a C3 compound synthesis metabolic pathway, in which the formic acid assimilation pathway is combined with a central carbon assimilation pathway and a pyruvate formate lyase is further introduced thereto.

In the present invention, the recombinant microorganism may be further introduced with a gene encoding pyruvate formate lyase or a recombinant vector containing the gene.

In the present invention, the gene encoding pyruvate formate lyase may be a nucleic acid molecule represented by SEQ ID NO: 22, but is not limited thereto.

Figure 8:
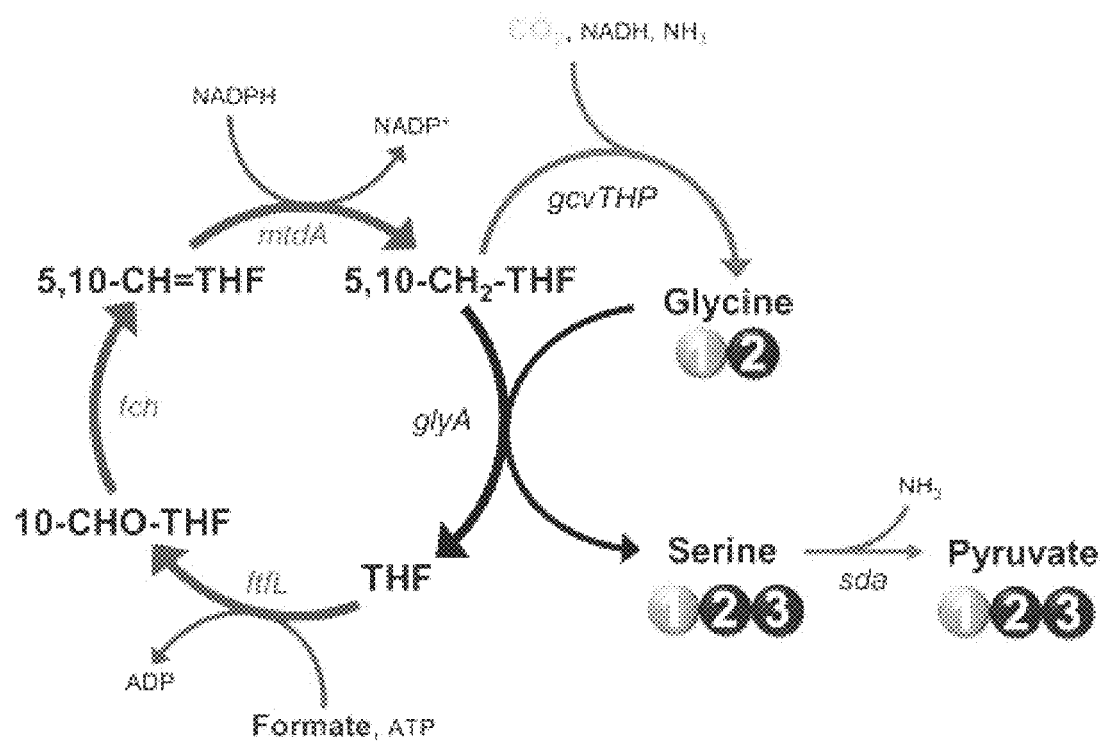
FIG. 8 shows a novel metabolic pathway for synthesizing glycine, serine and pyruvate using formic acid and carbon dioxide according to an embodiment of the present invention.

Another type of central carbon assimilation pathway developed in the present invention is a pathway for fixing formic acid and carbon dioxide in microorganisms, and FIG. 8 shows genes, coenzymes and energy transfer substances involved in the formic acid and carbon dioxide assimilation pathway.

In the present invention, the formic acid and carbon dioxide assimilation pathways synthesize one molecule of glycine from carbon dioxide and formic acid, and synthesizes one molecule of serine from glycine and one molecule of formic acid. The synthesized serine is converted into pyruvate through serine deaminase and a C3 or longer compound can be synthesized from pyruvate. The host microorganism has the carbon assimilation capability by externally introducing the formic acid and carbon dioxide assimilation pathways.

Figure 10:
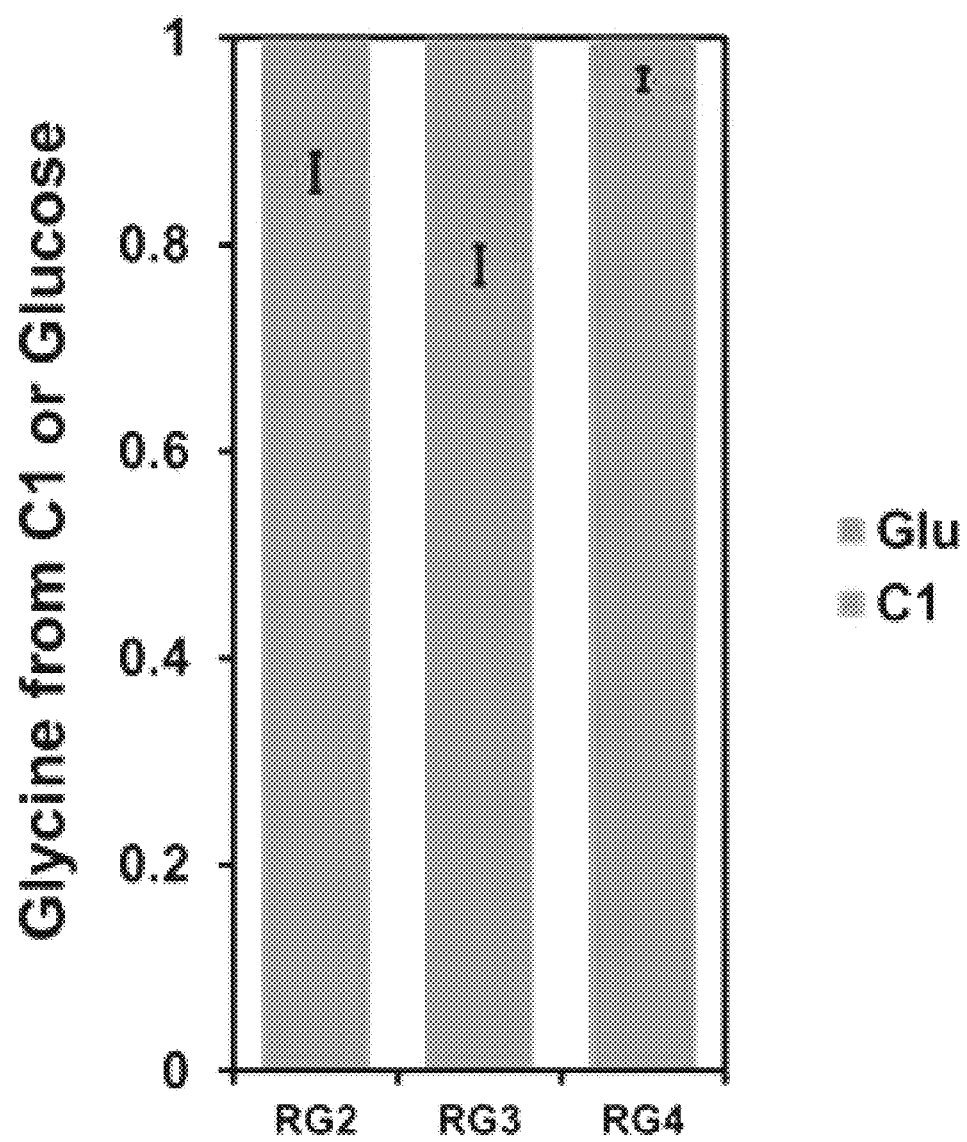
FIG. 10 shows the proportion of glycine (C1, orange) synthesized from formic acid and carbon dioxide and the proportion of glycine (Glu, light blue) synthesized from glucose in recombinant E. coli introduced with a novel metabolic pathway according to an embodiment of the present invention.
Figure 11:
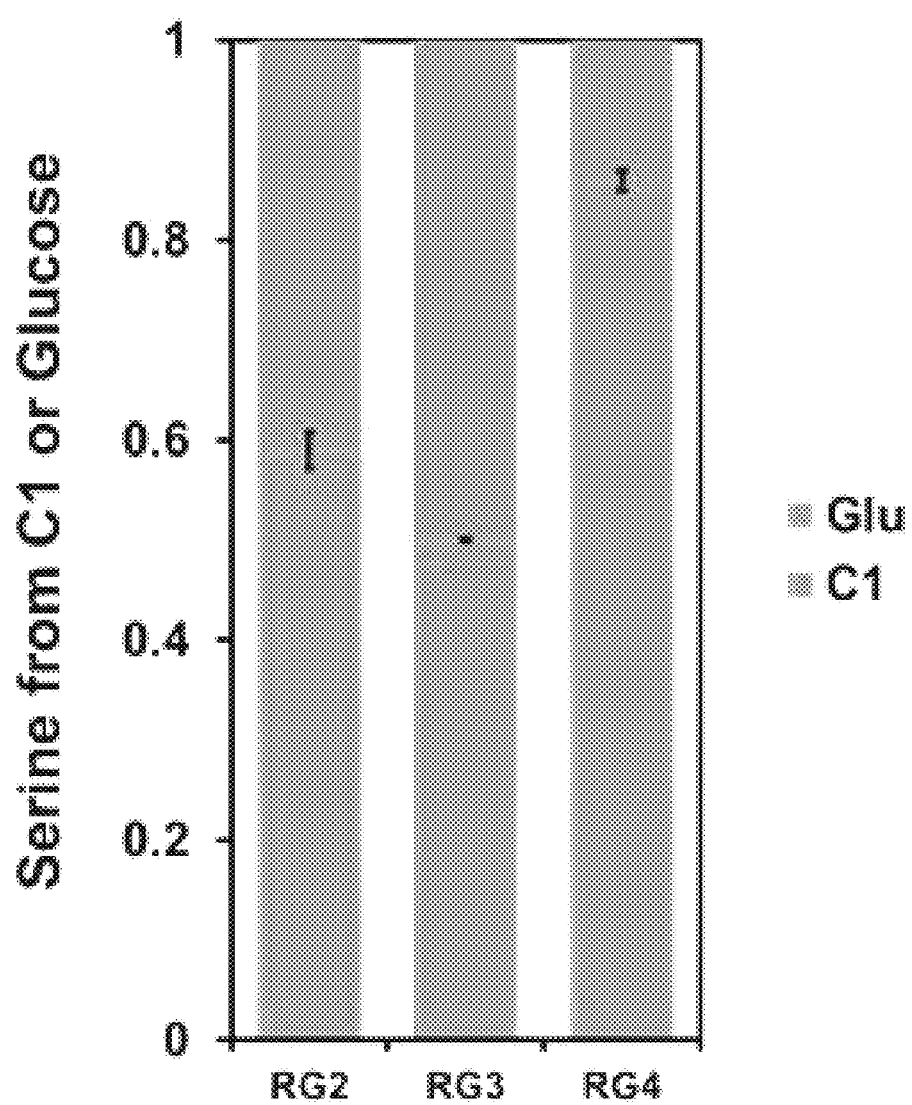
FIG. 11 shows the proportion of serine (C1, orange) synthesized from formic acid and carbon dioxide and the proportion of serine (Glu, light blue) synthesized from glucose in recombinant E. coli introduced with a novel metabolic pathway according to an embodiment of the present invention.

That is, the present invention verified that serine and glycine can be synthesized from formic acid and carbon dioxide via the formic acid and carbon dioxide assimilation pathways, and it was confirmed that assimilation efficiency is improved through the change of the gene expression intensity and the deletion of a specific gene in the host microorganism (FIGS. 10 and 11).

Figure 12:
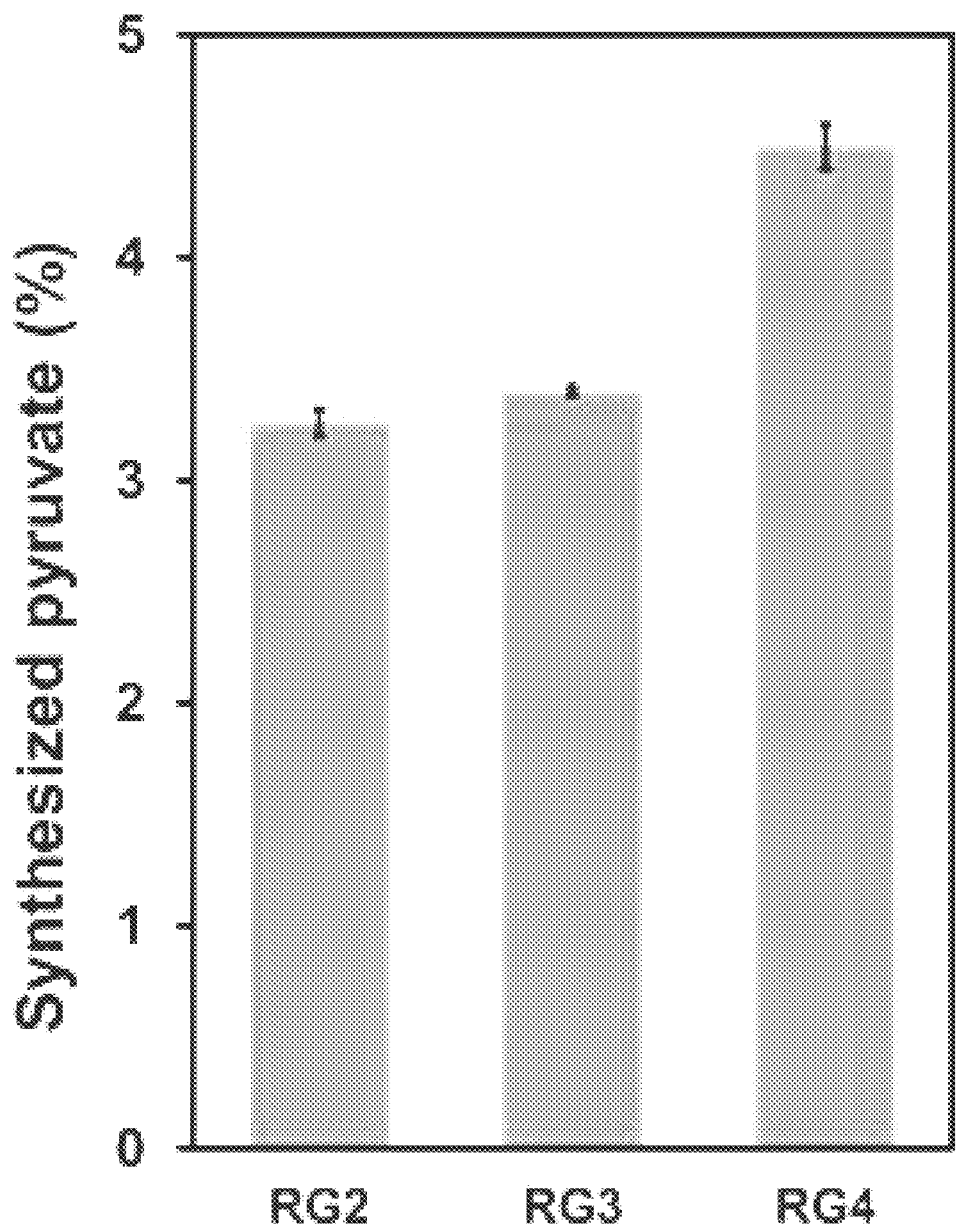
FIG. 12 shows the proportion of pyruvate synthesized from formic acid and carbon dioxide in recombinant E. coli introduced with a novel metabolic pathway according to an embodiment of the present invention.
Figure 13A:
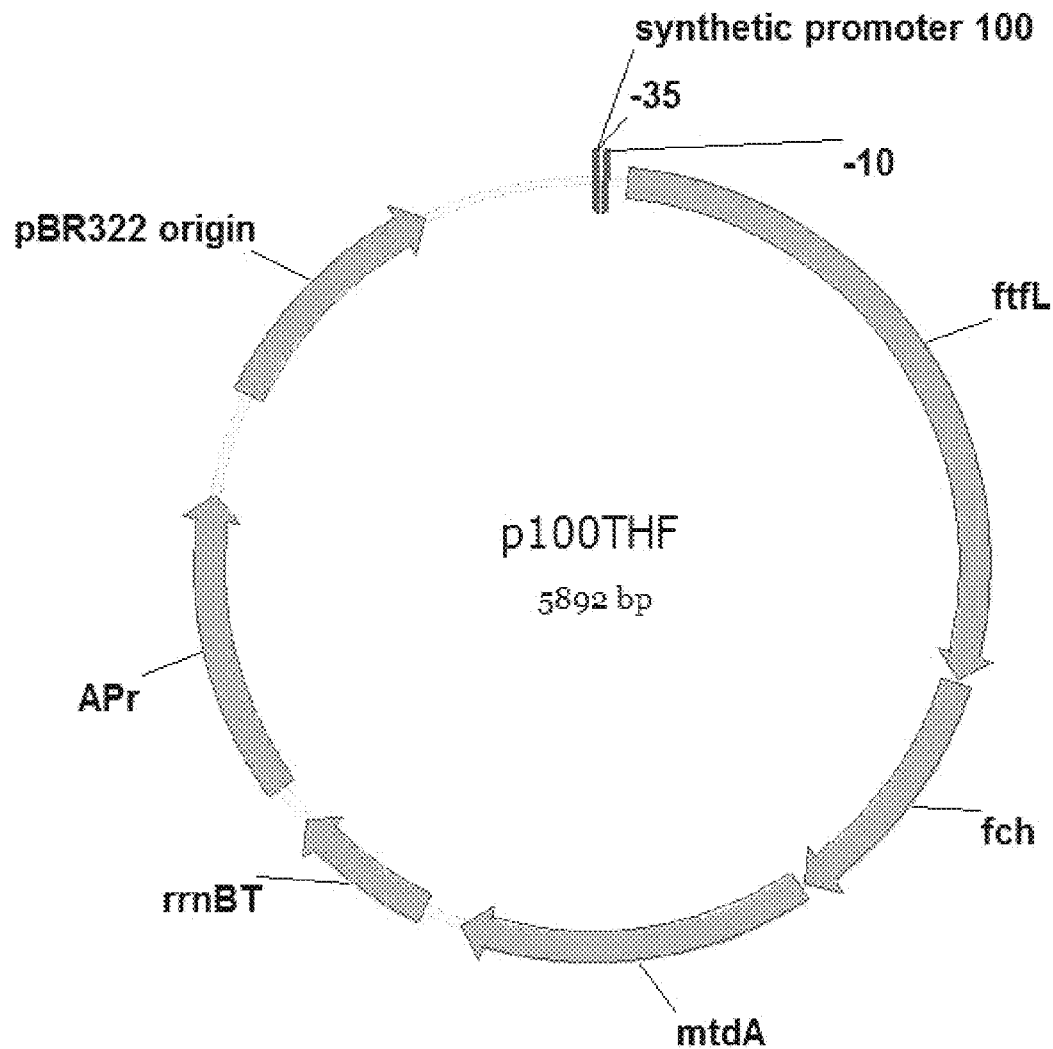
FIGS. 13A-13E shows five types of plasmid maps produced according to an embodiment of the present invention.
Figure 13B:
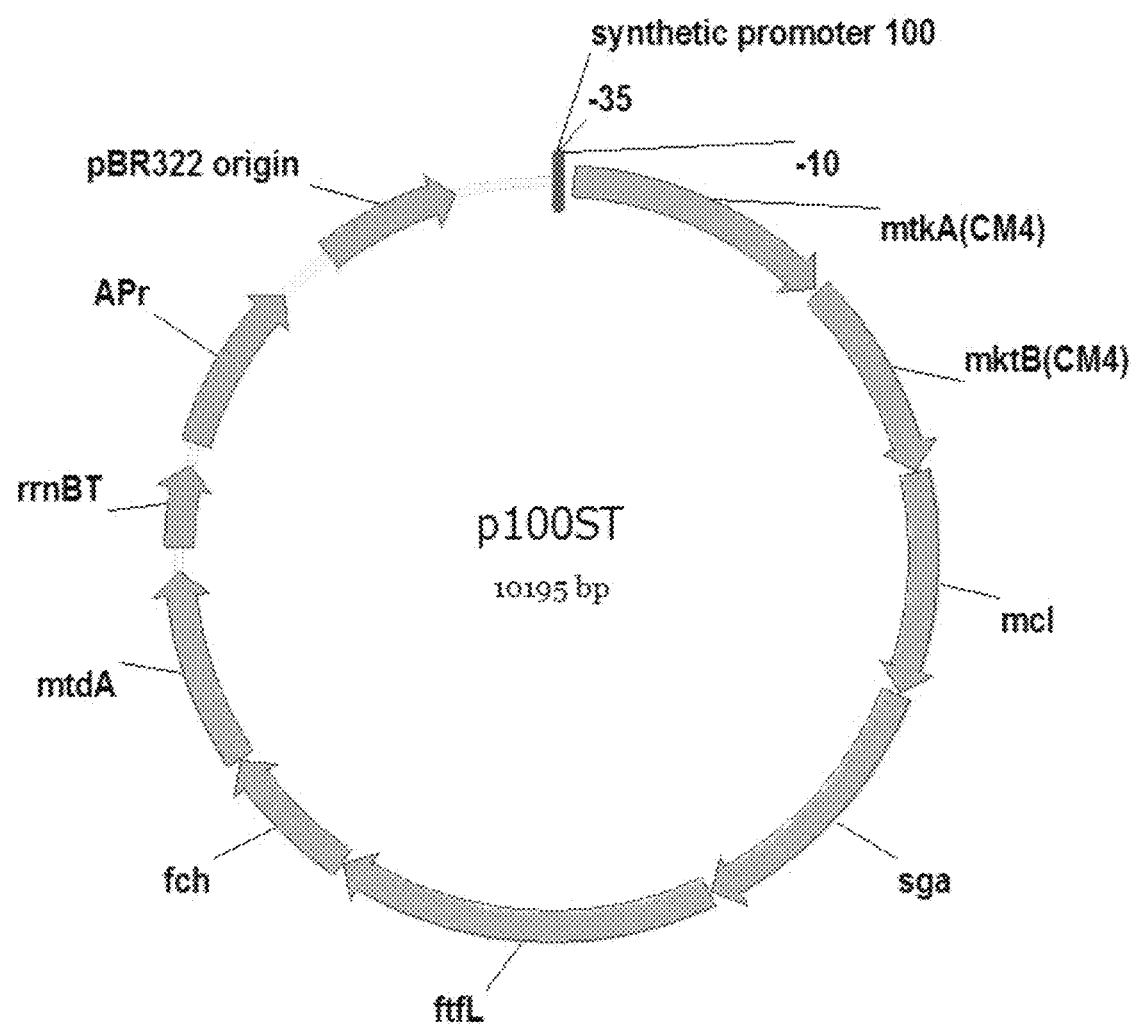
Figure 13C:
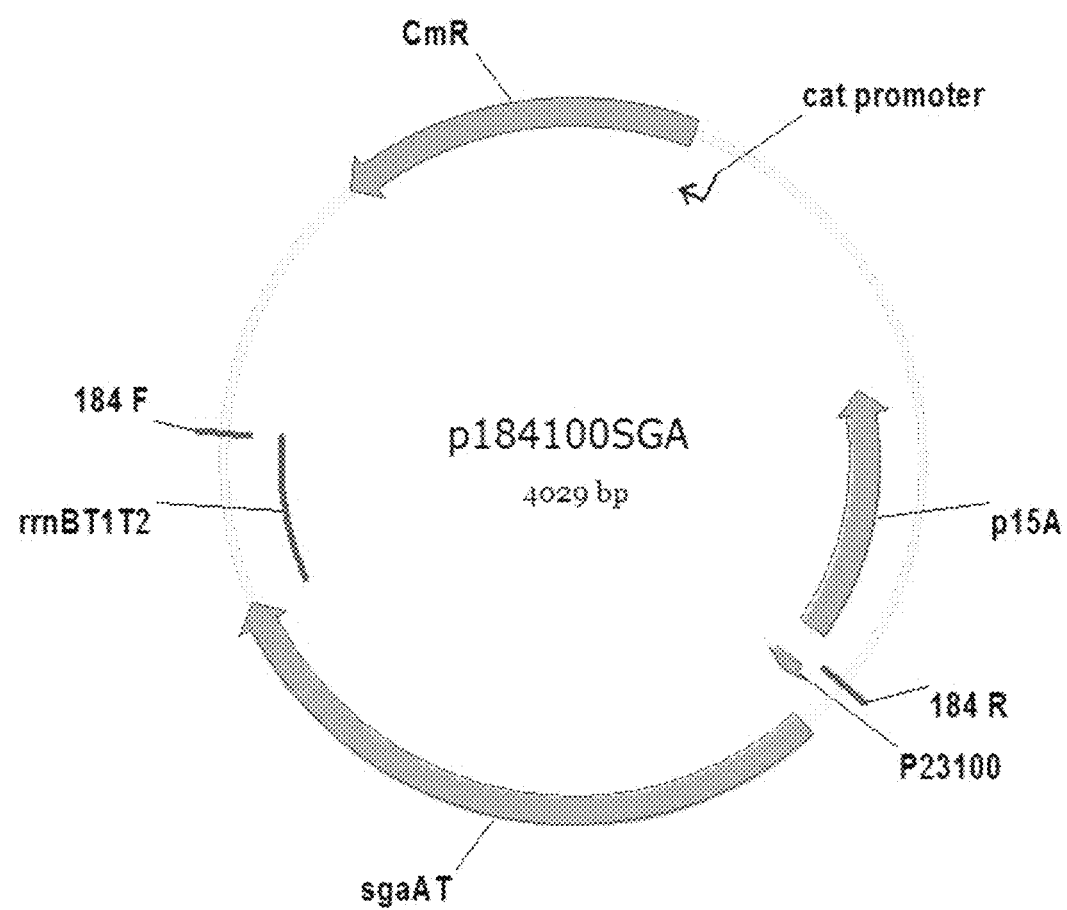
Figure 13D:
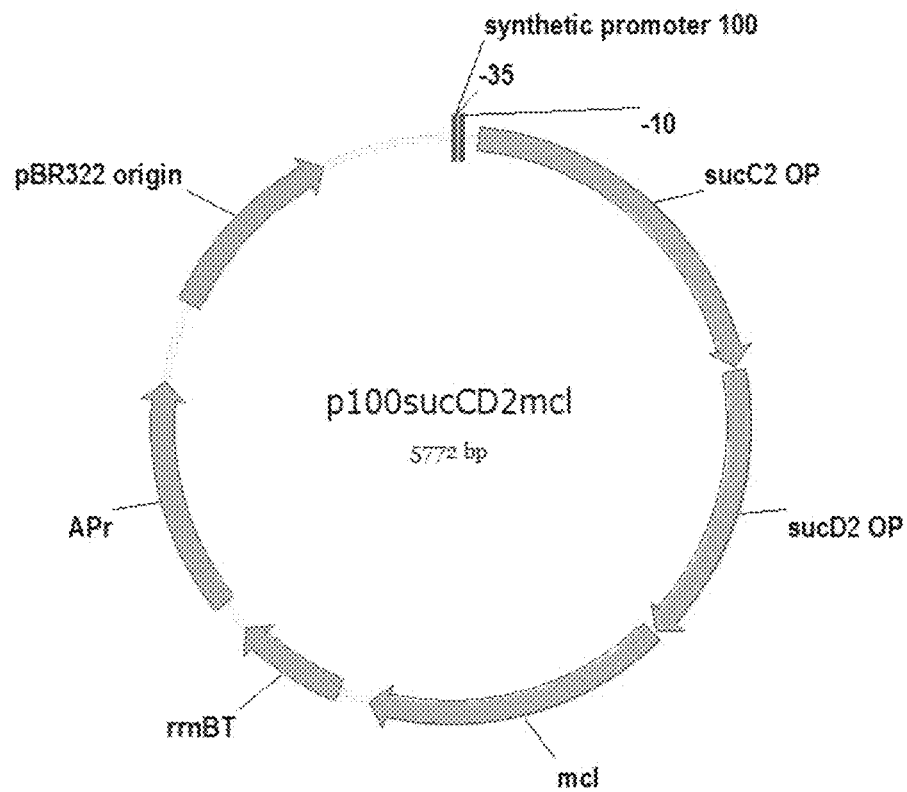
Figure 13E:
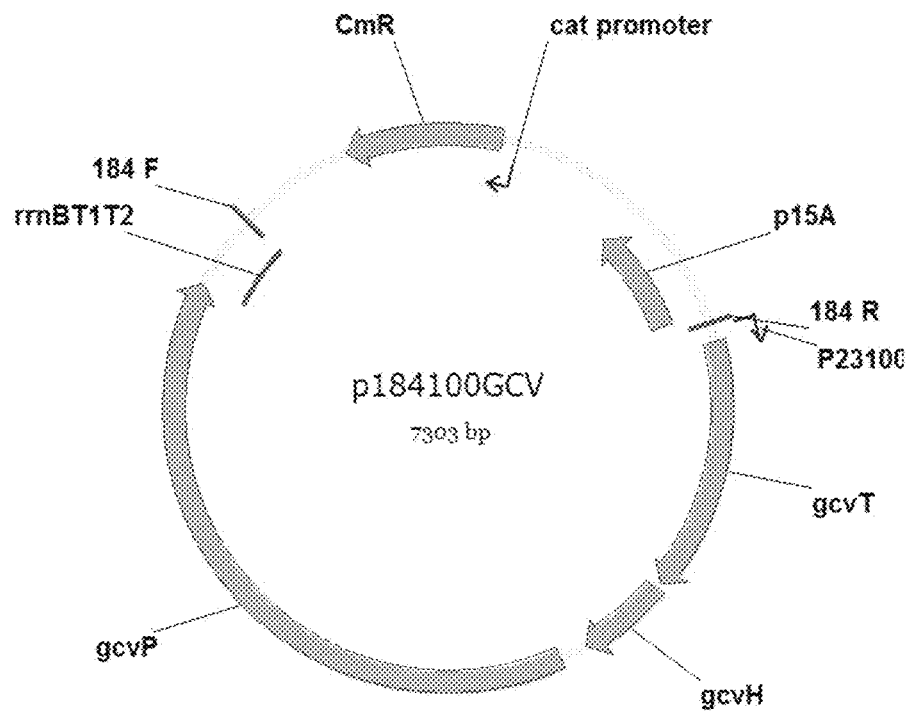

In addition, the present invention verified that pyruvate can be synthesized from formic acid and carbon dioxide via the formic acid and carbon dioxide assimilation pathways, and it was confirmed that assimilation efficiency is improved through the change of the gene expression intensity and the deletion of a specific gene in the host microorganism (FIG. 12).

Figure 9:
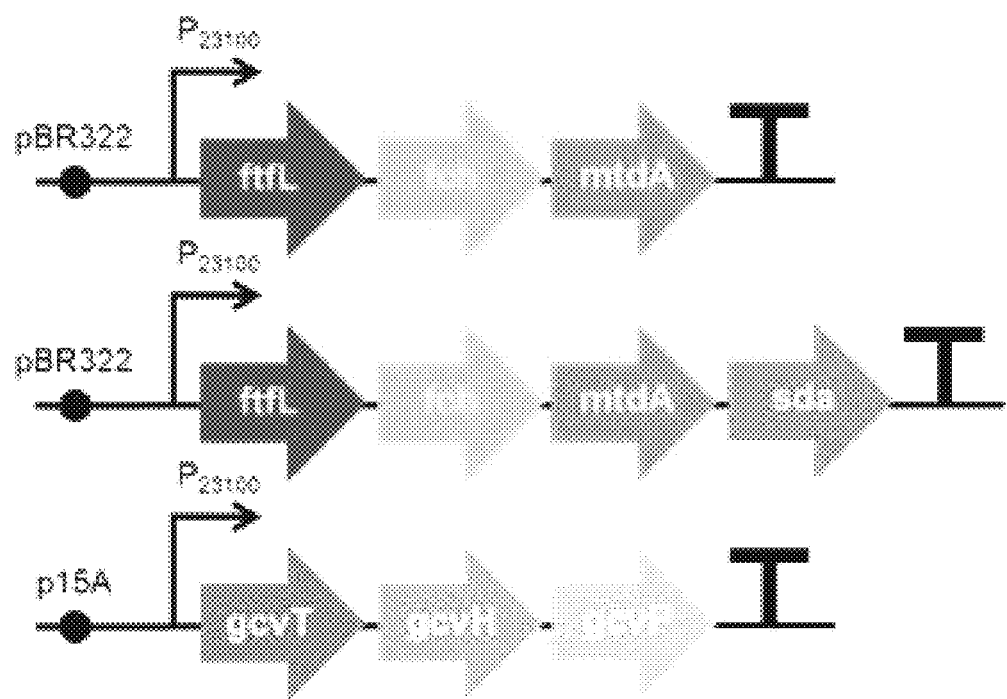
FIG. 9 shows a synthetic operon produced in order to construct, in E. coli as a model microorganism, a novel metabolic pathway for synthesizing glycine, serine and pyruvate using formic acid and carbon dioxide according to an embodiment of the present invention.

In the present invention, the genes could be transformed into a host microorganism in the form of a plasmid containing a synthetic operon (FIG. 9), and the synthetic operon could be produced so as to include at least one selected from the group consisting of: formate-tetrahydrofolate ligase, methenyl tetrahydrofolate cyclohydrolase, and methylene-tetrahydrofolate dehydrogenase of the *Methylobacterium* genus microorganism; methenyl tetrahydrofolate cyclohydrolase of the *Acetobacterium* genus microorganism; and a glycine cleavage complex and serine deaminase of the *Escherichia* genus microorganism.

The results of transformation of the plasmid containing the synthetic operon into the host microorganism showed that the recombinant microorganism into which such a novel metabolic pathway was introduced exhibited considerably improved capability to synthesize glycine, serine and pyruvate from formic acid and carbon dioxide.

Accordingly, in another aspect, the present invention is directed to a recombinant microorganism having a metabolic pathway for synthesizing a C3 compound wherein glycine, serine and pyruvate are synthesized from formic acid and carbon dioxide through the introduction of a novel metabolic pathway.

The present invention relates to a recombinant microorganism having improved assimilation from formic acid and carbon dioxide through introduction of a gene encoding an enzyme involved in a formic acid assimilation pathway or a recombinant vector containing the gene into a host microorganism having a central carbon assimilation pathway. The enzyme is at least one selected from the group consisting of formate-tetrahydrofolate ligase, methenyl tetrahydrofolate cyclohydrolase, and methylene-tetrahydrofolate dehydrogenase.

In the present invention, the gene encoding formate-tetrahydrofolate ligase is a nucleic acid molecule represented by SEQ. ID. NO: 7, the gene encoding methenyl tetrahydrofolate cyclohydrolase is a nucleic acid molecule represented by SEQ ID NO: 8, and the gene encoding methylene-tetrahydrofolate dehydrogenase is a nucleic acid molecule represented by SEQ ID NO: 9 or SEQ ID NO: 19, but the present invention is not limited thereto.

In the present invention, a glycine cleavage complex may be enhanced, amplified or further introduced into the recombinant microorganism, and expression of the gene constituting the glycine cleavage complex may be reinforced by substituting an intrinsic promoter with any one strong promoter selected from the group consisting of a trc promoter, a tac promoter, a T7 promoter, a lac promoter and a trp promoter, or is overexpressed through a plasmid overexpression system. The glycine cleavage complex may be a nucleic acid molecule represented by SEQ ID NO: 63, but is not limited thereto.

In one embodiment of the present invention, a recombinant microorganism that glycine cleavage complex is enhanced, amplified in or further introduced into is produced by overexpressing the glycine cleavage complex represented by SEQ ID NO: 63 through a plasmid overexpression system or substituting the intrinsic promoter located upstream of the gcvT gene of the glycine cleavage complex with a strong promoter {SEQ ID NO: 67 (NCBI information: NC_000913.3 Region 3049125-3050667 was substituted with SEQ ID NO: 68, and the changed sequence corresponds to the promoter}.

In the present invention, the recombinant microorganism may be characterized in that the gcvR gene is deleted, and the gcvR gene may be a nucleic acid molecule represented by SEQ ID NO: 66, but the present invention is not limited thereto.

In the present invention, serine diaminase may be enhanced, amplified or further introduced into the recombinant microorganism, and the serine deaminase may be a nucleic acid molecule represented by SEQ ID NO: 69, but the present invention is not limited thereto.

In the present invention, the host microorganism may inherently possess a central carbon assimilation pathway i); or may have a central carbon assimilation pathway introduced externally ii).

In the present invention, the genes may be derived from any one selected from the group consisting of the genera *Methylobacterium, Roseobacter, Rhodobacter, Chloroflexus, Acetobacterium, Mannheimia, Escherichia* and *Arabidopsis*, but the present invention is not limited thereto.

In the present invention, the recombinant microorganism is capable of biosynthesizing pyruvate, glycine or serine assimilated from formic acid and carbon dioxide, but the present invention is not limited thereto.

In the present invention, the recombinant microorganism may be selected from the group consisting of the genera *Escherichia, Mannheimia, Rhodobacter* and *Methylobacterium*, but the present invention is not limited thereto.

The gene of the present invention may undergo variations in many ways in the coding region so long as the amino acid sequence of the protein expressed from the coding region is not changed, and may undergo variations or modifications so long as the expression of genes is not affected in a region excluding the coding region, and such varied or modified genes also fall within the scope of the present invention.

Therefore, the present invention also includes a polynucleotide having a base sequence substantially identical to the gene as well as a fragment of the gene. The term "substantially identical polynucleotide" means a gene encoding an enzyme having the same function as that used in the present invention, regardless of the homology of the sequence. The term "fragment of the gene" also means a gene encoding an enzyme having the same function as that used in the present invention, regardless of the length of the fragment.

In addition, the amino acid sequence of the protein, which is an expression product of the gene of the present invention, can be obtained from biological resources such as various microorganisms, so long as the titer and activity of the corresponding enzyme are not affected, and these biological resources also fall within the scope of the present invention.

Thus, the present invention also includes polypeptides having amino acid sequences substantially identical to the protein, as well as fragments of the polypeptides. The term "substantially identical polypeptide" means a protein having the same function as that used in the present invention regardless of the homology of the amino acid sequence. The term "fragment of the polypeptide" also means a protein having the same function as that used in the present invention, regardless of the length of the fragment.

As used herein, the term "vector" means a DNA product containing a DNA sequence operably linked to a regulation sequence capable of expressing DNA in a suitable host, and may be a plasmid, phage particle or a simple potential genome insert. Once the vector is transformed with an appropriate host, it may replicate and function independently of the genome of the host, or may often be integrated with the genome itself. Since the plasmid is the most commonly used type of vector, the terms "plasmid" and "vector" are sometimes used interchangeably throughout the specification of the present invention. For the purpose of the present invention, a plasmid vector is preferably used. A typical plasmid vector that can be used for this purpose includes (a) a replication origin to efficiently conduct replication so as to include several to several hundred plasmid vectors per host cell, (b) an antibiotic resistance gene to screen a host cell transformed with the plasmid vector and (C) a restriction enzyme cleavage site into which a foreign DNA fragment is inserted. Even if an appropriate restriction enzyme cleavage site is not present, the vector and foreign DNA can be easily ligated using a synthetic oligonucleotide adapter or a linker according to a conventional method. After ligation, the vector should be transformed into an appropriate host cell. Transformation can be easily carried out using a calcium chloride method or electroporation (Neumann, et al., EMBO J., 1: 841, 1982).

Expression vectors well-known in the art can be used as vectors for enhancing or overexpressing genes according to the present invention.

When a nucleotide sequence is aligned with another nucleotide sequence based on functional relation, it is "operably linked" thereto. This may be gene(s) and regulatory sequence(s) linked in such a way so as to enable gene expression when a suitable molecule (e.g., a transcriptional activator protein) is linked to the regulatory sequence(s). For example, DNA for a pre-sequence or secretory leader is operably linked to DNA for a polypeptide, when expressed as a pre-protein involved in the secretion of the polypeptide; and a promoter or enhancer is operably linked to a coding sequence when it affects the transcription of the sequence; or a ribosome-binding site is operably linked to a coding sequence when it affects the transcription of the sequence; or the ribosome-binding site is operably linked to a coding sequence when positioned to facilitate translation. Generally, "operably linked" means that the linked DNA sequence is in contact therewith, or a secretory leader is in contact therewith and is present in the reading frame. However, the enhancer need not be in contact. The linkage of these sequences is carried out by ligation (linkage) at convenient restriction enzyme sites. When no such site exists, a synthetic oligonucleotide adapter or a linker according to a conventional method is used. As is well known in the art, in order to increase the expression level of a transgene in a host cell, the gene should be operably linked to a transcriptional/translational expression regulation sequence that functions in a selected expression host. Preferably, the expression regulation sequence and the corresponding gene are included in one recombinant vector containing both a bacterial selection marker and a replication origin. When the host cell is a eukaryotic cell, the recombinant vector should further include a useful expression marker in the eukaryotic expression host.

The host cell transformed with the recombinant vector described above constitutes another aspect of the present invention. As used herein, the term "transformation" means introducing DNA into a host and allowing the DNA to be replicable by an extrachromosomal factor or chromosomal integration.

It should be understood that not all vectors function identically in expressing the DNA sequences of the present invention. Likewise, not all hosts function identically for the same expression system. However, those skilled in the art will be able to make appropriate selections from among a variety of vectors, expression regulation sequences and hosts without excessive burden of experimentation and without departing from the scope of the present invention. For example, selection of a vector should be carried out in consideration of a host because the vector should be replicated therein. The number of replications of the vector, the ability to control the number of replications, and the expression of other proteins encoded by the corresponding vector, such as the expression of antibiotic markers, should be also considered.

In addition, the gene introduced in the present invention may be introduced into the genome of a host cell and exist as a chromosomal factor. It will be apparent to those skilled in the art that even insertion of the gene into the genome of the host cell has the same effect as introducing the recombinant vector into the host cell.

Any host microorganism can be used as the host microorganism of the present invention without limitation and the host microorganism is preferably an *Escherichia* genus, *Mannheimia* genus, *Rhodobacter* genus or *Methylobacterium* genus microorganism.

The present inventors have also developed a metabolic pathway for synthesizing a C3 compound by combining the above-mentioned cyclic metabolic pathway with the reverse reaction of pyruvate formate lyase, and identified that the metabolic pathway enables formic acid and carbon dioxide to be effectively fixed into a C3 compound.

Therefore, in another aspect, the present invention is directed to a recombinant microorganism capable of producing a C3 compound, wherein a gene encoding pyruvate formate lyase or a recombinant vector containing the gene is further introduced into the recombinant microorganism.

In the present invention, the pyruvate formate lyase has a forward reaction activity of decomposing pyruvate into formate and acetyl-CoA as well as a reverse reaction activity thereof, and has excellent reverse reaction activity, with the conversion number of reverse reaction of 280 per sec, and previous research has demonstrated that pyruvate can be synthesized through the reverse reaction of the enzyme (Zelcbuch et al., *Biochemistry*, 55:17, 2423-2426, 2016). The pyruvate formate lyase is inherently found in *E. coli* as a host microorganism, but, when depending on inherent expression, it is difficult to maintain the expression amount above a predetermined level, since the expression of the enzyme is regulated by culturing conditions. Therefore, in order to synthesize a stable C3 compound, in the present invention, the enzyme is further introduced based on the plasmid, or is controlled to be overexpressed using a strong promoter.

In the present invention, the gene encoding pyruvate formate lyase may be a nucleic acid molecule represented by SEQ ID NO: 22.

In the present invention, the gene may be overexpressed by any one strong promoter selected from the group consisting of a trc promoter, a tac promoter, a T7 promoter, a lac promoter, a BBa23100 synthetic promoter and a trp promoter.

In another aspect, the present invention is directed to a method for producing a useful substance having a C3 compound as an intermediate product using the recombinant microorganism.

The method for producing the useful substance according to the present invention includes: (a) culturing the recombinant microorganism with formic acid and carbon dioxide as a carbon source to produce a useful substance having a C3 compound as an intermediate product; and (b) recovering the resulting useful substance. In the present invention, the C3 compound may be pyruvate. Examples of the useful substance include alcohols, amino acids, organic acids, alkenes and polymeric monomers. More specifically, the C3 compound includes, but is not limited to, straight or branched alcohols having 3 or more carbon atoms, isobutanol, propanol, hexanol, heptanol, octanol, nonanol, decanol, tert-butanol, 1-pentanol, 2-pentanol, 3-pentanol, 2-methyl-1-butanol, 3-methyl-1-butanol, 2-methyl-2-butanol, putrescine, L-ornithine, arginine, polycyclic aromatic hydrocarbons (PAHs), polylactate, polylactate-co-glycolate, poly(2-hydroxyisovalerate-co-lactate), polyhydroxybutyrate (PHB), 4-hydroxybutyrate, biodiesel, gasoline, olefin, 5-aminovaleric acid, gamma-butyric acid, 3-hydroxypropionic acid, 3-aminopropionic acid, acrylic acid, 1,3-diaminopropane, caprolactam, threonine, valine, isoleucine, fumaric acid, malic acid, succinic acid, ceramide, astaxanthin, silybin, lycopene, lutein, retinol and the like. Pyruvate is an intermediate which is formed during the decomposition process of biomass including glycolipid and wood through glycolysis in most microorganism genera including the genus *Escherichia*. Pyruvate is a substance that is in center of carbon rearrangement reactions through native metabolic pathways in microorganisms and thus can be converted into all useful substances reported to be capable of being produced in microorganisms through the native metabolic pathways of microorganisms or additional metabolic pathways introduced from the outside, which will be apparent to those skilled in the art. Accordingly, the present invention includes all substances that can be synthesized using pyruvate produced by the recombinant microorganism according to the present invention.

In another aspect, the present invention is directed to a method for producing a C3 compound using the recombinant microorganism.

The method according to the present invention includes: (a) culturing the recombinant microorganism in formic acid and carbon dioxide as a carbon source to produce a C3 compound; and (b) recovering the produced C3 compound, wherein the C3 compound is pyruvate, serine or glycine, but is not limited thereto.

Hereinafter, the present invention will be described in more detail with reference to the following examples. However, it will be obvious to those skilled in the art that the following examples are provided only for illustration of the present invention and should not be construed as limiting the scope of the present invention.

Example 1: Production of Recombinant Plasmid for Introduction of Foreign Genes and Production of Recombinant *E. coli*

In order to construct a formic acid and carbon dioxide assimilation pathway and to synthesize a C3 compound with high efficiency, necessary genes were introduced into *Escherichia coli*, which is a target microorganism, using a recombinant plasmid. The plasmid used for construction of the assimilation pathway was a p10099A plasmid including an Ampicillin resistance gene, a pBR322 replication origin, and the synthetic promoter BBa 23100. PCR was conducted using the plasmid as a template and the primers of SEQ ID NO: 1 and SEQ ID NO: 2, and the amplified gene fragment was then recovered and purified to prepare a gene fragment used as a plasmid backbone for the production of the recombinant plasmid.

[SEQ ID NO: 1]:
5'-ACTGATAAGCCTTTCGGTAAGGTACCCGGGGATCCTCTAG-3'

[SEQ ID NO: 2]:
5'-TCGTGTAAGTGTCTCAACAAGAGCTCGAATTCGCTAGCAC-3

The foreign gene fragments required for plasmid production were prepared by conducting PCR using the genomic DNA of microorganisms having the corresponding gene as a template and using a primer designed for amplification of the gene, and then collecting and purifying the amplified gene fragment, and the corresponding genes and primer sequences are shown in Tables 1 and 2 below.

TABLE 1

NCBI information of foreign genes to be amplified and derived microorganisms

| Target gene | NCBI information | Derived microorganism |
| --- | --- | --- |
| mtkA | Malate-CoA ligase β-subunit<br>CP001298 REGION: 2233122-2234294<br>[SEQ ID NO: 3] | *Methylobacterium extorquens* CM4 |
| mtkB | Malate-CoA ligase α-subunit<br>CP001298 REGION: 2234317-2235207<br>[SEQ ID NO: 4] | *Methylobacterium extorquens* CM4 |
| mcl | Malyl-CoA lyase<br>CP001298 REGION: 2238448-2239422<br>[SEQ ID NO: 5] | *Methylobacterium extorquens* CM4 |
| sga | Serine-glyoxylate aminotransferase<br>CP001298 REGION: 2228409-2229617<br>[SEQ ID NO: 6] | *Methylobacterium extorquens* CM4 |
| ftfL | Formate-tetrahydrofolate ligase<br>CP001298 REGION: 434499-436172<br>[SEQ ID NO: 7] | *Methylobacterium extorquens* CM4 |
| fch | Methenyl tetrahydrofolate cyclohydrolase<br>CP001298 REGION: 2231946-2232572<br>[SEQ ID NO: 8] | *Methylobacterium extorquens* CM4 |

TABLE 1-continued

NCBI information of foreign genes to be amplified and derived microorganisms

| Target gene | NCBI information | Derived microorganism |
|---|---|---|
| mtdA | Methylene-tetrahydrofolate dehydrogenase CP001298 REGION: 2230986-2231852 [SEQ ID NO: 9] | *Methylobacterium extorquens* CM4 |
| hprA | Hydroxypyruvate reductase CP001298 REGION: 2229898-2230842 [SEQ ID NO: 10] | *Methylobacterium extorquens* CM4 |
| mtkAB1 | Malate-CoA ligase1 CP000362 REGION: 1122758-1124841 [SEQ ID NO: 11] | *Roseobacter denitrificans* OCh 114 |
| mtkAB2 | Malate-Co A ligase2 CP000362 REGION: 4121281-4123370 [SEQ ID NO: 12] | *Roseobacter denitrificans* OCh 114 |
| sga | Serine-glyoxylate aminotransferase CP000362 REGION: 1677707-1678939 [SEQ ID NO: 13] | *Roseobacter denitrificans* OCh 114 |
| mcl1 | Malyl-CoA lyase1 CP000577 REGION: 2779302-2780159 [SEQ ID NO: 14] | *Rhodobacter sphaeroides* ATCC 17029 |
| mcl2 | Malyl-CoA lyase2 CP000577 REGION: 432306-433262 [SEQ ID NO: 15] | *Rhodobacter sphaeroides* ATCC 17029 |
| sga | Serine-glyoxylate aminotransferase CP000577 REGION: 2000551-2001753 [SEQ ID NO: 16] | *Rhodobacter sphaeroides* ATCC 17029 |
| smtA | Succinyl-CoA: (S)-malate CoA-transferase CP000909 REGION: 224515-225801 [SEQ ID NO: 17] | *Chloroflexus aurantiacus* J-10-fl |
| smtB | Succinyl-CoA: (S)-malate CoA-transferase CP000909 REGION: 223035-224252 [SEQ ID NO: 18] | *Chloroflexus aurantiacus* J-10-fl |
| folD | Methenylene-tetrahydrofolate dehydrogenase CP002987 REGION: 1083442-1084347 [SEQ ID NO: 19] | *Acetobacterium woodii* KCTC 1655 |
| pckA | Phosphoenolpyruvate carboxykinase AE016827 REGION: 2222647-2224263 [SEQ ID NO: 20] | *Mannheimia succiniciproducens* MBEL55E |
| sga | Serine-glyoxylate aminotransferase AB048945 REGION: 60-1265 [SEQ ID NO: 21] | *Arabidopsis thaliana* |
| pfl | Pyruvate formate lyase NCBI GeneID: 945514 [SEQ ID NO: 22] | *Escherichia. Coli.* |

TABLE 2

Primer sequences used for amplification of foreign gene fragments

| Target gene | Primer sequence |
|---|---|
| mtkA [SEQ ID NO: 3] | [SEQ ID NO: 23]: 5'-TTGTTGAGACACTTACACGA AGGAGGAATTCATGGACGTTCACGAGTACCAAG-3' [SEQ ID NO: 24]: 5'-TCAGTGCTTGGCGCCGTGGC-3' |
| mtkB [SEQ ID NO: 4] | [SEQ ID NO: 25]: 5'-TGCCACGGCGCCAAGCACTGA AGGAGGAATTCATGAGCATTCTCATCGACG-3' [SEQ ID NO: 26]: 5'-TCACGCCGCGCGGGCGAG-3' |
| mcl [SEQ ID NO: 5] | [SEQ ID NO: 27]: 5'-CTCGCCCGCGCGGCGTGA AGGAGGAATTCATGAGCTTCACCCTGATCCA G-3' [SEQ ID NO: 28]: 5'-TTACTTTCCGCCCATCGCG-3' |
| sga [SEQ ID NO: 6] | [SEQ ID NO: 29]: 5'-CGCGATGGGCGGAAAGTAA AGGAGGAATTCATGGCGGCAACGAGACGTCC-3' [SEQ ID NO: 30]: 5'-TCAAGCCTTGGCGAGCGGG-3' |
| ftfL [SEQ ID NO: 7] | [SEQ ID NO: 31]: 5'-CCCGCTCGCCAAGGCTTGA AGGAGGAATTCATGCCCTCAGATATCGAGATC-3' [SEQ ID NO: 32]: 5'-CTAGAACAGCCCGTCGATC-3' |
| fch [SEQ ID NO: 8] | [SEQ ID NO: 33]: 5'-GATCGACGGGCTGTTCTAG AGGAGGAATTCATGGCCGGCAACGAGACGATC-3' [SEQ ID NO: 34]: 5'-TCAGTTTACCTTGGACTTCAC-3' |
| mtdA [SEQ ID NO: 9] | [SEQ ID NO: 35]: 5'-GTGAAGTCCAAGGTAAACTGA AGGAGGAATTCATGTCCAAGAAGCTGCTCTTC-3' [SEQ ID NO: 36]: 5'-TCATCCGCCAAAACAGCCAAG TCAGGCCATTTCCTTGGCC-3' |
| hprA [SEQ ID NO: 10] | [SEQ ID NO: 37]: 5'-TTGTTGAGACACTTACACGA AGGAGGAATTCATGACAAAGAAAGTCGTCTTC-3' [SEQ ID NO: 38]: 5'-TCATCCGCCAAAACAGCCAA GTTACGCCTCGACGACGTTCTG-3' |
| mtkAB1 [SEQ ID NO: 11] | [SEQ ID NO: 39]: 5'-TTGTTGAGACACTTACACGA AGGAGGAATTCATGGATATCCACGAATACCAAG-3' [SEQ ID NO: 40]: 5'-TCATGCGGCCTCCTTCCTCA G-3' |

TABLE 2-continued

Primer sequences used for amplification of foreign gene fragments

| Target gene | Primer sequence |
|---|---|
| mtkAB2 [SEQ ID NO: 12] | [SEQ ID NO: 41]: 5'-TTGTTGAGACACTTACACGA AGGAGGAATTCATGGATATCCATGAATACCAAG-3' <br> [SEQ ID NO: 42]: 5'-TCACGCGGCCTCCATCACTT TG-3' |
| sga [SEQ ID NO. 13] | [SEQ ID NO: 43]: 5'-TTGTTGAGACACTTACACGA AGGAGGAATTCATGACCCAAAAAAGCAACCTG-3' <br> [SEQ ID NO: 44]: 5'-TCATCCGCCAAAACAGCCAA GCTACTCCGACGCCCCCGCCG-3' |
| mcl1 [SEQ ID NO: 14] | [SEQ ID NO: 45]: 5'-TTGTTGAGACACTTACACGA AGGAGGAATTCATGGCGCATCAGGCTCATCC-3' <br> [SEQ ID NO: 46]: 5'-TCAGCTTGCCCTGAACGCGG-3' |
| mcl2 [SEQ ID NO: 15] | [SEQ ID NO: 47]: 5'-CCGCGTTCAGGGCAAGCTGA AGGAGGAATTCATGAGCTTCCGCCTTCAGCC-3' <br> [SEQ ID NO: 48]: 5'-TCAGGCCGAGATCATTTCTG-3' |
| sga [SEQ ID NO: 16] | [SEQ ID NO: 49]: 5'-TTGTTGAGACACTTACACGA AGGAGGAATTCATGTCGCTTGCGCACGGCCG-3' <br> [SEQ ID NO: 50]: 5'-TCATCCGCCAAAACAGCCAA GTCAGGCCGCCGCGCCGAGGC-3' |
| smtA [SEQ ID NO: 17] | [SEQ ID NO: 51]: 5'-TTGTTGAGACACTTACACGA-3' <br> [SEQ ID NO: 52]: 5'-CTAGATAATCTTACGGCTGC-3' |
| smtB [SEQ ID NO: 18] | [SEQ ID NO: 53]: 5'-GCAGCCGTAAGATTATCTAG-3' <br> [SEQ ID NO: 54]: 5'-CTAAATGACACGTTTGGAAC-3' |
| folD [SEQ ID NO: 19] | [SEQ ID NO: 55]: 5'-GTGAAGTCCAAGGTAAACTGAAGGAGGAATTCATGGCAGCAA AATTATTAAG-3' <br> [SEQ ID NO: 56]: 5'-TCATCCGCCAAAACAGCCAAGC TATAATAAGCCGTTTTGC-3' |
| pckA [SEQ ID NO: 20] | [SEQ ID NO: 57]: 5'-TTGTTGAGACACTTACACGA AGGAGGAATTCATGACAGATCTTAATCAATTAAC-3' <br> [SEQ ID NO: 58]: 5'-TTATGCTTTAGGACCGGCAG-3' |
| sga [SEQ ID NO: 21] | [SEQ ID NO: 59]: 5'-TTGTTGAGACACTTACACGA AGGAGGAATTCATGGACTATATGTATGGACC-3' <br> [SEQ ID NO: 60]: 5'-TCATCCGCCAAAACAGCCAA GTTAGATTCTAGAGGGAATGAG-3' |
| Pfl [SEQ ID NO: 22] | [SEQ ID NO: 61]: 5'-AGAACGTCGTCGAGGCGTAAAGGAGGAATTCATGACGAATCGT ATCTCTCG-3' <br> [SEQ ID NO: 62]: 5'-TTACAGCTGATGCGCTGTCC-3' |

Another plasmid used for constructing the assimilation pathway was a plasmid including a chloramphenicol resistance gene and a replication origin p15A and a synthetic promoter BBa_23100. PCR was conducted using the plasmid as a template and the primers of SEQ ID NO: 1 and SEQ ID NO: 2, and then the amplified gene fragment was recovered and purified to prepare a gene fragment used as a plasmid backbone for the production of the recombinant plasmid.

The foreign gene fragments required for plasmid production were prepared by conducting PCR using the genomic DNA of microorganisms having the corresponding gene as a template and using a primer designed for amplification of the gene, and then collecting and purifying the amplified gene fragment, and the corresponding genes and primer sequences are shown in Tables 3 and 4 below.

TABLE 3

NCBI information of foreign genes to be amplified and derived microorganisms

| Target gene | NCBI information | Derived microorganism |
|---|---|---|
| GCV | Glycine cleavage complex AP009048.1 REGION: 3044824-3049323 [SEQ ID NO: 63] | *Escherichia coli.* |
| SDA | Serine deaminase CP017979.1 REGION: 1802037-1803401 [SEQ ID NO: 69] | *Escherichia coli.* |

TABLE 4

Primer sequences used for amplification of foreign gene fragments

| Target gene | Primer sequence |
|---|---|
| GCV [SEQ ID NO: 63] | [SEQ ID NO: 64]: 5'-TTGTTGAGACACTTACACGAAGGAGGAATTCATGGCACAACA GACTCCTTTG-3' <br> [SEQ ID NO: 65]: 5'-TCATCCGCCAAAACAGCCAAGTTACTGGTATTCGCTAATCGG-3' |

The plasmid backbone gene fragments and amplified gene fragments were amplified using the Gibson assembly method (Gibson et al., *Nat. Methods*, 6:5, 343-345, 2009), which is commonly used for the assembly of gene fragments, and each plasmid was constructed to contain one or more of the foreign genes set forth in Table 1 or Table 3 above. In addition, a recombinant strain wherein the gcvR gene (SEQ ID NO: 66, NCBI information: NC_000913.3, Region 2599906-2600478) is deleted and the promoter of the gene constituting the glycine cleavage complex is changed {SEQ ID NO: 67 (NCBI Information: NC_000913.3 Region 3049125-3050667) is substituted as shown in SEQ ID NO: 68}. The recombinant strain having a gene deletion and substitution was produced using a homologous recombination method commonly used in the art (Datsenko et al., *PNAS*, 97: 12, 6640-6645, 2000). Representative plasmids prepared in the present invention are shown in Table 5 and FIGS. 13A-13E.

TABLE 5

| Plasmid | Characteristics |
|---|---|
| p100THF | Including pBR322 replication origin, Ampicillin resistance gene, BBa_23100 synthetic promoter, SEQ ID NO: 7 formate-tetrahydrofolate ligase, SEQ ID NO: 8 methenyl tetrahydrofolate cyclohydrolase, and SEQ ID NO: 9 methylene-tetrahydrofolate dehydrogenase |
| p100ST | Including pBR322 replication origin, Ampicillin resistance gene, BBa_23100 synthetic promoter, SEQ ID NO: 7 formate-tetrahydrofolate ligase, SEQ ID NO: 8 methenyl tetrahydrofolate cyclohydrolase, SEQ ID |

TABLE 5-continued

| Plasmid | Characteristics |
|---|---|
| | NO: 9 methylene-tetrahydrofolate dehydrogenase, SEQ ID NO: 6 serine-glyoxylate transaminase, SEQ ID NO: 5 malyl-CoA lyase and SEQ ID NOS: 3 and 4 malate-CoA ligase |
| p184100SGA | Including p15A replication origin, chloramphenicol resistance gene, BBa_23100 synthetic promoter, SEQ ID NO: 21 serine-glyoxylate transaminase |
| p100sucCD2mcl | Including pBR322 replication origin, Ampicillin resistance gene, BBa_23100 synthetic promoter, SEQ ID NO: 5 malyl-CoA lyase and SEQ ID NOS: 17 and 18 malate-CoA ligase |
| p184100GCV | Including p15A replication origin, chloramphenicol resistance gene, BBa_23100 synthetic promoter, SEQ ID NO: 63 glycine cleavage complex |
| pTrcTHF | Including pBR322 replication origin, Ampicillin resistance gene, Trc promoter, SEQ ID NO: 7 formate-tetrahydrofolate ligase, SEQ ID NO: 8 methenyl tetrahydrofolate cyclohydrolase, and SEQ ID NO: 9 methylene-tetrahydrofolate dehydrogenase |

The recombinant plasmid produced by the method described above was transformed into *E. coli* to prepare recombinant *E. coli*. The *E. coli* used in the present invention was *E. coli* DH5α (Invitrogen, USA), and transformation into *E. coli* was carried out using a chemical transformation method commonly used in the art. Representative recombinant *E. coli* produced in the present invention are shown in Table 6 below.

TABLE 6

| Strain name | Gene type |
|---|---|
| DH5α THF | DH5α harboring plasmid p100THF |
| DH5α ST1 | DH5α harboring plasmid p100ST |
| DH5α ST2 | DH5α harboring plasmid p100ST and p184100SGA |
| DH5α ST3 | DH5α harboring plasmid p100sucCD2mcl |
| DH5α RG2 | DH5α harboring plasmids p100THF and p184100GCV |
| DH5α RG3 | DH5α harboring plasmids pTrcTHF and p184100GCV |
| DH5α RG4 | DH5α ΔgcvR Ptrc: gcvTHP harboring plasmid p100THF |

Example 2: Identification of Assimilation of Formic Acid and Carbon Dioxide Using Carbon Isotope Analysis Carbon isotope analysis was performed to verify whether or not the recombinant *E. coli* produced in Example 1 could effectively assimilate formic acid and carbon dioxide. In order to verify the assimilation of formic acid, experiments were performed using wild-type *Escherichia coli* (DH5α WT) as a control group and recombinant *Escherichia coli* (DH5α THF) introduced with formate-tetrahydrofolate ligase encoded by a nucleic acid molecule represented by SEQ ID NO: 7, methenyl tetrahydrofolate cyclohydrolase encoded by a nucleic acid molecule represented by SEQ ID NO: 8, and methylene-tetrahydrofolate dehydrogenase encoded by a nucleic acid molecule represented by SEQ ID NO: 9 among the recombinant *Escherichia coli* produced in Example 1.

In order to verify whether or not the assimilated formic acid is linked to the central carbon assimilation pathway, experiments were performed using a recombinant *Escherichia coli* further introduced with serine-glyoxylate transaminase encoded by a nucleic acid molecule represented by SEQ ID NO: 6, 3, 16 or 21. Further, in order to verify whether or not the assimilated formic acid is linked to the central carbon assimilation pathway and effectively synthesizes acetyl-CoA together with carbon dioxide, experiments were performed using a recombinant microorganism introduced with malyl-CoA lyase encoded by a nucleic acid molecule of SEQ ID NO: 5 or 15, and further introduced with a malate-CoA ligase encoded by a nucleic acid molecule represented by SEQ ID NO: 3, 4, 11 or 12.

For the carbon isotope analysis, the control and experimental *E. coli* were cultured in M9 medium containing formate and bicarbonate ion labeled with a $^{13}C$ carbon isotope (see the composition shown in Table 7 below), and then the *E. coli* cell samples and acetic acid samples contained in the culture solution were analyzed. Analysis of the mass number of amino acid constituting *E. coli* using *Escherichia coli* cell samples was carried out using gas-chromatography/mass spectroscopy after hydrolysis of all the proteins constituting *Escherichia coli* under strongly acidic and high-temperature conditions (Zamboni et al., *Nat. protocols*, 4:6, 878-892, 2009). Analysis of the acetic acid sample contained in the culture solution was carried out by lyophilizing the culture solution, separating the acetic acid contained in the culture solution into acetate, and conducting analysis using the gas-chromatography/mass-spectroscopy analysis method.

TABLE 7

| Composition of M9 medium | |
|---|---|
| Ingredient | Content (g/l) |
| $Na_2HPO_4$ | 3.6 |
| $KH_2PO_4$ | 3 |
| NaCl | 0.5 |
| $NH_4Cl$ | 1 |
| $MgSO_4$ | 0.24 |
| $CaCl_2$ | 0.011 |
| Glucose | 5 |
| Sodium formate $^{13}C$ | 2.76 |
| Folate | 0.01 |
| Sodium bicarbonate $^{13}C$ | 3.4 |
| $FeSO_4$ | 0.00455 |
| $NiSO_4$ | 0.00464 |
| Sodium molybdate | 0.00618 |
| Thiamine | 0.01 |

Example 2-1: Identification of Formic Acid Assimilation Through Formic Acid Assimilation Pathway The assimilation of formic acid in the cyclic formic acid and carbon dioxide assimilation pathway developed in the present invention is carried out though the bonding between tetrahydrofolate and formic acid among the two cyclic metabolic pathways, as shown in FIG. 1. Tetrahydrofolate is regenerated through three metabolic pathways proceeding after the bond between formic acid and tetrahydrofolate, and the formic-acid-derived carbon is assimilated into serine. Also, methylene-tetrahydrofolate, which is one of intermediates of the pathway, is also used as an intermediate of the methionine synthesis metabolic pathway, so that methionine is also labeled with the formic-acid-derived carbon along the methionine synthesis metabolic pathway.

As shown in FIG. 2B, the results of analysis of formic acid assimilation showed that the recombinant *Escherichia coli* (DH5α THF) strain produced in Example 1 contained isotopes in 90% of the total methionine contained in *E. coli*, while the wild-type control group (DH5α WT) contained isotopes in 31% of total methionine. The results of measurement of the isotope containment proportion of serine present in the recombinant *E. coli* (DH5α THF) showed that 100% of total serine was observed to contain isotopes. The results of measurement of isotope containment proportion of serine present in the wild-type control group (DH5α WT) showed that 35% of total serine was observed to contain isotopes.

Figure 3:
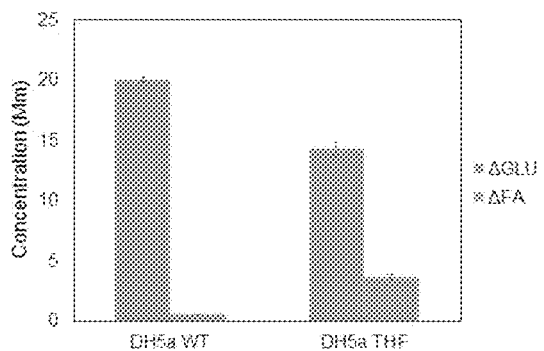
FIG. 3 shows results of quantitative analysis of the assimilation amount of formic acid of the wild-type control group (DH5α WT) and the recombinant microorganism (DH5α THF) (A) and the assimilation efficiency thereof (B)
Figure 3:
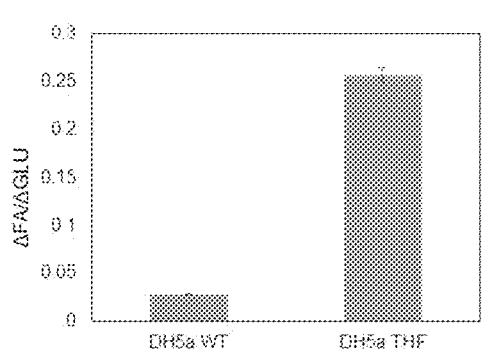

Meanwhile, the results of quantitative analysis of formic acid assimilation of the wild-type control (DH5α WT) and recombinant *E. coli* (DH5α THF) and comparison of assimilation efficiency showed that recombinant *E. coli* (DH5α THF) used formic acid as a main carbon source, while the wild-type control (DH5α WT) used almost no formic acid (FIG. 3). As a result, it can be seen that the recombinant *E. coli* (DH5α THF) exhibited formic acid assimilation efficiency (ΔFA/ΔGlu) about 10 times higher than the wild-type control group (DH5α WT).

From the above results, it could be seen that the recombinant *E. coli* according to the present invention exhibited significantly improved assimilation efficiency compared to that of the wild-type control.

Example 2-2 Identification of Assimilation with Central Carbon Metabolism (CCM) of Formic Acid Whether or not the formic acid assimilated through the cyclic formic acid and carbon dioxide assimilation metabolic pathway developed in the present invention was assimilated into the central carbon metabolism (CCM) of *E. coli*. was verified. The formic-acid-derived carbon assimilated through the metabolic pathway of Example 2-1 was migrated to 3-hydroxypyruvate through serine-glyoxylate transaminase and corresponded to the carbon at position 3 of pyruvate by a series of reactions. At this time, the proportion of carbon isotopes present in pyruvate could be determined by analysis of alanine and valine (Zelcbuch et al., *Biochemistry*, vol. 55:17, 2423-2426, 2016). Based on this principle, the carbon isotopes contained in pyruvate were analyzed. As a result, as shown in FIG. 4, in the case of recombinant *E. coli* (DH5α ST2) having the cyclic formic acid and carbon dioxide assimilation pathway, isotopes were detected in amounts of 29% and 28.2% of total alanine and valine, respectively. In the case of wild-type *E. coli*, isotopes were detected in amounts of 23.7% and 26.2% of total alanine and valine, respectively. Therefore, the isotope analysis showed that the recombinant microorganism of the present invention effectively induces the process of assimilating the formic acid, which is assimilated through the cyclic formic acid and carbon dioxide assimilation pathway, into central carbon metabolism (CCM) of *E. coli*.

Example 2-3 Identification of Production of Acetyl-CoA Through Carbon Dioxide Assimilation and Regeneration of Glyoxylate The identification of the production of acetyl-CoA and regeneration of glyoxylate through the carbon dioxide assimilation process, which is the last part of the cyclic process of the cyclic formic acid and carbon dioxide assimilation pathway developed in the present invention, was carried out by measuring the contents of carbon isotopes in acetic acid produced by the recombinant *E. coli* of Example 1 and the wild-type *E. coli*. That is, the carbon-dioxide-derived carbon corresponds to the carbon at position 1 of the acetyl-CoA synthesized by the cyclic formic acid and the carbon dioxide assimilation pathway developed in the present invention. Generally, acetyl-CoA is converted at a certain proportion into acetic acid in *Escherichia coli*. Therefore, analysis of acetic acid provides analysis of the content of isotopes in acetyl-CoA.

The results of analysis of the carbon isotope content in acetyl-CoA based on this principle showed that the recombinant *Escherichia coli* (DH5α ST3) having the metabolic pathway had an increased isotope content in acetic acid compared to wild-type *Escherichia coli*. Therefore, it could be seen that the recombinant *E. coli* according to the present invention was effective for carbon dioxide assimilation and glyoxylate regeneration.

Example 3: Identification of Production of Pyruvate Through Cyclic Metabolic Pathway Using Carbon Isotope Analysis The pyruvate formate lyase was further introduced into the cyclic metabolic pathway to identify whether or not pyruvate was synthesized from acetyl-CoA and formic acid through the reverse reaction of the enzyme, which can be identified through carbon isotope analysis. That is, when formic acid and carbon dioxide labeled with a carbon isotope having a mass number of 13 are supplied, pyruvate synthesized through the corresponding cyclic metabolic pathway and the reverse reaction of pyruvate formate lyase has formic-acid-derived carbon at positions 1 and 3 and carbon-dioxide-derived carbon at position 2.

Based on this principle, pyruvate was analyzed by the same method as the carbon isotope analysis used in Example 2-2. As a result, it could be seen that, in the case of recombinant *E. coli* (DH5α ST2) having a cyclic metabolic pathway produced in the present invention, the proportion of amino acids increased by 3 or more above the original mass number of corresponding amino acids in valine and alanine, was significantly increased compared to wild-type *E. coli*.

Example 4: Identification of Production of Glycine, Serine and Pyruvate from Formic Acid and Carbon Dioxide Using Carbon Isotope Analysis Carbon isotope analysis was performed to verify whether or not the recombinant *E. coli* produced in Example 1 could assimilate formic acid and carbon dioxide to produce glycine, serine and pyruvate. For the verification of formic acid assimilation, the experiments were carried out using the wild-type *Escherichia coli* (DH5α WT), as a control group, and recombinant *E. coli* (DH5α RG2) introduced with formate-tetrahydrofolate ligase encoded by a nucleic acid molecule represented by SEQ ID NO: 7, methenyl tetrahydrofolate cyclohydrolase encoded by the nucleic acid molecule represented by SEQ ID NO: 8, methylene-tetrahydrofolate dehydrogenase encoded by the nucleic acid molecule represented by SEQ ID NO: 9, and a glycine cleavage complex encoded by the nucleic acid molecule represented by SEQ ID NO: 63 among the recombinant *Escherichia coli* produced in Example 1.

In order to verify the improvement in assimilation efficiency of formic acid and carbon dioxide, experiments were performed using recombinant *Escherichia coli* (DH5α RG4) obtained by deleting a gcvR gene (SEQ ID NO: 66, NCBI information: NC_000913.3, Region 2599906-2600478) and changing a promoter of a gene constituting the glycine cleavage complex {substituting SEQ ID NO: 67 (NCBI information: NC_000913.3 Region 3049125-3050667) with SEQ ID NO: 68) in the recombinant *E. coli* (DH5α RG2).

For the carbon isotope analysis, the control and experimental *E. coli* were cultured in M9 medium containing formate and bicarbonate ion labeled with $^{13}C$ carbon isotope (see the composition shown in Table 7 above), and then the *E. coli* cell samples were analyzed. Analysis of the mass number of amino acid constituting *E. coli* using *E. coli* cell samples was carried out using gas-chromatography/mass spectroscopy after hydrolysis of all of the proteins constituting *Escherichia coli* under strongly acidic and high-temperature conditions (Zamboni et al., *Nat. protocols*, 4:6, 878-892, 2009).

Example 4-1: Identification of Synthesis of Glycine, Serine and Pyruvate from Formic Acid and Carbon Dioxide The recombinant *E. coli* (DH5α RG2) synthesized glycine from one molecule of formic acid and one molecule of carbon dioxide through the metabolic pathway shown in FIG. 8. After culturing the recombinant *E. coli* using the M9 medium described in Table 7 above, *E. coli* cell samples were analyzed. As a result, it could be confirmed that 86% of the total glycine was synthesized from formic acid and carbon dioxide. In addition, 56% of total serine was synthesized from formic acid and carbon dioxide, and 3.5% of total pyruvate was synthesized from formic acid and carbon dioxide. A recombinant *Escherichia coli* (DH5α RG3) with improved expression of a formic acid assimilation pathway was produced using a strong promoter in order to improve the assimilation efficiency of formic acid and carbon dioxide, and the proportions of glycine, serine and pyruvate synthesized from formic acid were measured. However, an improvement of the effect thereof compared to that of the recombinant *Escherichia coli* (DH5α RG2) produced above was not observed.

Example 4-2: Improvement of Assimilation Efficiency of Formic Acid and Carbon Dioxide Through Gene Deletion and Promoter Modification in Recombinant *E. coli*

In order to improve the synthesis of glycine, serine and pyruvate from formic acid, a recombinant strain (DH5α RG4) was prepared by changing a regulatory gene (gcvR) controlling the expression of the glycine cleavage complex and the promoter of the glycine cleavage complex in the recombinant *E. coli* (DH5α RG2). The synthesis of glycine, serine and pyruvate from formic acid and carbon dioxide was analyzed. As a result, it could be seen that 96%, 86% and 7.3% of glycine, serine and pyruvate, respectively, were synthesized from formic acid and carbon dioxide.

In conclusion, based on the examples described above, the recombinant *E. coli* according to the present invention effectively acts on assimilation of formic acid and carbon dioxide through the cyclic metabolic pathway identified in the present invention, and further introduction of pyruvate formate lyase offers a significant increase in pyruvate synthesis efficiency. In addition, it can be seen that glycine, serine and pyruvate can be synthesized with high efficiency from formic acid and carbon dioxide through formic acid and carbon dioxide assimilation metabolic pathway.

Although specific configurations of the present invention have been described in detail, those skilled in the art will appreciate that this detailed description is provided as preferred embodiments for illustrative purposes and should not be construed as limiting the scope of the present invention. Therefore, the substantial scope of the present invention is defined by the accompanying claims filed and equivalents thereto.

DESCRIPTION OF SYMBOLS

Synthetic promoter 100: BBa23100 synthetic promoter
ftfL: SEQ ID NO: 7, formate-tetrahydrofolate ligase
fch: SEQ ID NO: 8, methenyl tetrahydrofolate cyclohydrolase
mtdA: SEQ ID NO: 9, methylene-tetrahydrofolate dehydrogenase
rrnBT: rrnB terminator
APr: Ampicillin resistance gene
pBR322 origin: pBR322 replication origin
mtkA(CM4): SEQ ID NO: 3, malate-CoA ligase β-subunit
mtkB(CM4): SEQ ID NO: 4, malate-CoA ligase α-subunit
mcl: SEQ ID NO: 5, malyl-CoA lyase
sga: SEQ ID NO: 6, serine-glyoxylate aminotransferase
CmR: chloramphenicol resistance gene
p15A: p15A replication origin
P23100: BBa23100 synthetic promoter
sgaAT: SEQ ID NO: 21, serine-glyoxylate aminotransferase
rrnBT1T2: rrnB terminator
sucC2 OP: SEQ ID NO: 17, succinyl-CoA:(S)-malate CoA-transferase
sucD2 OP: SEQ ID NO: 18, succinyl-CoA:(S)-malate CoA-transferase
gcvT: SEQ ID NO: 63, T subunit among glycine cleavage complex
gcvH: SEQ ID NO: 63, H subunit among glycine cleavage complex
gcvP: SEQ ID NO: 63, P subunit among glycine cleavage complex
trc-pro: Trc promoter
LacIq: mutant lacI repressor

INDUSTRIAL APPLICABILITY

The present invention provides a novel microorganism introduced with a novel cyclic metabolic pathway through which C3 or higher organic carbon compounds can be synthesized from formic acid and carbon dioxide, thereby effectively synthesizing pyruvate as a C3 organic compound using carbon dioxide, which is abundant in nature, and formic acid, which is of low toxicity and suitable for assimilation (anabolic) reactions in view of reaction kinetics and which can be easily and rapidly synthesized from carbon dioxide. As a result, the present invention is effective in economically producing organic carbon compounds, reducing carbon dioxide, which is the main cause of global warming, and synthesizing various high-value-added compounds from pyruvate as an intermediate product.

The invention claimed is:

1. A recombinant microorganism having improved assimilation from formic acid and carbon dioxide, obtained by introducing a gene encoding an enzyme involved in a formic acid assimilation pathway,
wherein the microorganism is *Escherichia coli* capable of synthesizing a C3 or larger carbon compound under the formic acid assimilation pathway combined with a cyclic pathway for fixing carbon dioxide,
wherein the gene encoding an enzyme involved in a formic acid assimilation pathway comprises:
the gene encoding formate-tetrahydrofolate ligase comprising the nucleic acid molecule of SEQ ID NO: 7;
the gene encoding methenyl tetrahydrofolate cyclohydrolase comprising the nucleic acid molecule of SEQ ID NO: 8; and
the gene encoding methylene-tetrahydrofolate dehydrogenase comprising the nucleic acid of SEQ ID NO: 9 or SEQ ID NO: 19; and
wherein the gene encoding an enzyme involved in the cyclic pathway for fixing carbon dioxide comprises one or more genes selected from:
the gene encoding a serine-glyoxylate transaminase comprising the nucleic acid of SEQ ID NO: 6, SEQ ID NO: 13, SEQ ID NO: 16, or SEQ ID NO: 21;
the gene encoding a malyl-CoA lyase comprising the nucleic acid of SEQ ID NO: 5, SEQ ID NO: 14, or SEQ ID NO: 15; and
the gene encoding a malate-CoA ligase comprising the nucleic acid of SEQ ID NO: 3, SEQ ID NO: 4, SEQ ID NO: 11, or SEQ ID NO: 12.

2. The recombinant microorganism according to claim 1, wherein the gene encoding an enzyme involved in a cyclic pathway for fixing carbon dioxide further comprises:
the gene encoding a succinyl-CoA:(S)-malate CoA-transferase comprising the nucleic acid of SEQ ID NO: 17 or SEQ ID NO: 18;
the gene encoding a phosphoenolpyruvate carboxykinase comprising the nucleic acid of SEQ ID NO: 20; and/or
the gene encoding hydroxypyruvate reductase comprising the nucleic acid of SEQ ID NO: 10.

3. The recombinant microorganism according to claim 1, wherein a gene encoding pyruvate formate lyase or a recombinant vector containing the gene is further introduced into or overexpressed in the recombinant microorganism.

4. The recombinant microorganism according to claim 3, wherein the gene encoding pyruvate formate lyase is the nucleic acid molecule of SEQ ID NO: 22.

5. The recombinant microorganism according to claim 3, wherein the gene is overexpressed by any one strong promoter selected from the group consisting of a trc promoter, a tac promoter, a T7 promoter, a lac promoter and a trp promoter.

6. The recombinant microorganism according to claim 1, wherein a glycine cleavage complex is enhanced, amplified or further introduced into the recombinant microorganism.

7. The recombinant microorganism according to claim 6, wherein the glycine cleavage complex is the nucleic acid molecule of SEQ ID NO: 63.

8. The recombinant microorganism according to claim 6, wherein the expression of the genes constituting the glycine cleavage complex is enhanced by introducing a plasmid containing the genes constituting the glycine cleavage complex, or substituting an intrinsic promoter of the gene with any one strong promoter selected from the group consisting of a trc promoter, a tac promoter, a T7 promoter, a lac promoter and a trp promoter.

9. The recombinant microorganism according to claim 6, wherein a gcvR gene is further deleted from the recombinant microorganism.

10. The recombinant microorganism according to claim 9, wherein the gcvR gene is the nucleic acid molecule of SEQ ID NO: 66.

11. The recombinant microorganism according to claim 1, wherein serine deaminase is enhanced, amplified or further introduced into the recombinant microorganism.

12. The recombinant microorganism according to claim 11, wherein the serine deaminase is the nucleic acid molecule of SEQ ID NO: 69.

13. The recombinant microorganism according to claim 1, wherein the recombinant microorganism is capable of biosynthesizing pyruvate, glycine and serine assimilated from formic acid and carbon dioxide.

14. A method for producing a useful compound having a C3 compound as an intermediate product comprising:
(a) culturing the recombinant microorganism according to claim 1 with formic acid and carbon dioxide as a carbon source to produce a useful substance having a C3 compound as an intermediate product; and (b) recovering the resulting useful substance.

15. The method according to claim 14, wherein the C3 compound is pyruvate and the useful substance is selected from the group consisting of butanol, isobutanol, hexanol, heptanol, octanol, nonanol, decanol, tert-butanol, 1-pentanol, 2-pentanol, 3-pentanol, 2-methyl-1-butanol, 3-methyl-1-butanol, 2-methyl-2-butanol, putrescine, L-ornithine, arginine, polycyclic aromatic hydrocarbons (PAHs), polylactate, polylactate-co-glycolate, poly(2-hydroxyisovalerate-co-lactate), polyhydroxybutyrate (PHB), 4-hydroxybutyrate, biodiesel, gasoline, olefin, 5-aminovaleric acid, gamma-butyric acid, 3-hydroxypropionic acid, 3-aminopropionic acid, acrylic acid, 1,3-aminopropane, caprolactam, threonine, valine, isoleucine, fumaric acid, malic acid, succinic acid, ceramide, astaxanthin, silybin, lycopene, lutein, and retinol.

16. A method for producing a C3 compound comprising:

(a) culturing the recombinant microorganism according to claim 1 with formic acid and carbon dioxide as a carbon source to produce a C3 compound; and (b) recovering the produced C3 compound.

* * * * *

UNITED STATES PATENT AND TRADEMARK OFFICE
CERTIFICATE OF CORRECTION

| | | |
|---|---|---|
| PATENT NO. | : 11,214,816 B2 | Page 1 of 1 |
| APPLICATION NO. | : 16/472876 | |
| DATED | : January 4, 2022 | |
| INVENTOR(S) | : Lee et al. | |

It is certified that error appears in the above-identified patent and that said Letters Patent is hereby corrected as shown below:

In the Specification

Column 22, Line 50, "mutant lad repressor" should be -- mutant lacI repressor --.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*